US008383819B2

(12) United States Patent
Matsuda et al.

(10) Patent No.: US 8,383,819 B2
(45) Date of Patent: Feb. 26, 2013

(54) METHOD FOR PRODUCING 4-OXOQUINOLINE COMPOUND

(75) Inventors: Koji Matsuda, Osaka (JP); Koji Ando, Osaka (JP); Shigeji Ohki, Osaka (JP); Jun-ichi Hoshi, Osaka (JP); Takahiro Yamasaki, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 1087 days.

(21) Appl. No.: 12/281,889

(22) PCT Filed: Mar. 6, 2007

(86) PCT No.: PCT/JP2007/054348

§ 371 (c)(1), (2), (4) Date: Sep. 5, 2008

(87) PCT Pub. No.: WO2007/102512

PCT Pub. Date: Sep. 13, 2007

(65) Prior Publication Data

US 2009/0036684 A1 Feb. 5, 2009

(30) Foreign Application Priority Data

Mar. 6, 2006 (JP) ................................ 2006-060277
Mar. 6, 2006 (JP) ................................ 2006-060298

(51) Int. Cl.
*C07D 215/00* (2006.01)

(52) U.S. Cl. ...................................................... 546/156

(58) Field of Classification Search ........................ None
See application file for complete search history.

(56) References Cited

U.S. PATENT DOCUMENTS

| | | | | |
|---|---|---|---|---|
| 3,472,859 | A | 10/1969 | Lesher et al. | |
| 4,695,646 | A | 9/1987 | Maurer et al. | |
| 5,182,401 | A | 1/1993 | Grohe | |
| 5,217,972 | A | 6/1993 | Grohe et al. | |
| 5,519,016 | A | 5/1996 | Kimura et al. | |
| 5,686,482 | A | 11/1997 | Ohmori et al. | |
| 5,688,791 | A | 11/1997 | Kimura et al. | |
| 5,985,894 | A | 11/1999 | Clemence et al. | |
| 5,989,451 | A | 11/1999 | Lemieux et al. | |
| 6,034,086 | A | 3/2000 | Kimura et al. | |
| 6,248,736 | B1 | 6/2001 | Turner et al. | |
| 6,248,738 | B1 | 6/2001 | Dickinson et al. | |
| 6,287,550 | B1 | 9/2001 | Trinh et al. | |
| 6,294,186 | B1 | 9/2001 | Beerse et al. | |
| 6,303,611 | B1 | 10/2001 | Zhang et al. | |
| 6,387,926 | B1 | 5/2002 | Bhide et al. | |
| 6,559,145 | B2 | 5/2003 | Ciske et al. | |
| 6,602,883 | B1 | 8/2003 | Bhide et al. | |
| 6,730,682 | B2 | 5/2004 | Schnute et al. | |
| 7,176,220 | B2 | 2/2007 | Satoh et al. | |
| 7,531,554 | B2 * | 5/2009 | Satoh et al. | 514/313 |
| 7,635,704 | B2 | 12/2009 | Satoh et al. | |
| 2002/0019397 | A1 | 2/2002 | Schnute et al. | |
| 2004/0127708 | A1 | 7/2004 | Fuji et al. | |
| 2004/0180910 | A1 | 9/2004 | Schnute et al. | |
| 2004/0198716 | A1 | 10/2004 | Arad et al. | |
| 2006/0019906 | A1 | 1/2006 | Satoh et al. | |
| 2006/0030710 | A1 | 2/2006 | Satoh et al. | |
| 2006/0217413 | A1 | 9/2006 | Satoh et al. | |
| 2008/0125594 | A1 * | 5/2008 | Dowdy et al. | 546/156 |
| 2009/0099366 | A1 | 4/2009 | Dowdy et al. | |
| 2009/0318702 | A1 | 12/2009 | Matsuda et al. | |

FOREIGN PATENT DOCUMENTS

| | | |
|---|---|---|
| EP | 0 287 951 | 10/1988 |
| EP | 0 319 906 | 6/1989 |
| EP | 0 326 891 | 8/1989 |
| EP | 0 457 090 | 11/1991 |
| EP | 0 498 721 | 8/1992 |
| EP | 0905558 A | 3/1999 |
| EP | 1 140 851 | 10/2001 |
| EP | 1 375 486 | 1/2004 |

(Continued)

OTHER PUBLICATIONS

Bouzard, D. et al., "Fluoronaphthyridines and Quinolones as Anti-bacterial Agents. 1. Synthesis and Structure-Activity Relationships of New 1-Substituted Derivatives," Journal of Medicinal Chemistry, American Chemical Society, Washington, US, vol. 32, No. 3, pp. 537-542 (Jan. 1, 1989).

Domagala, J.M. et al., "1-Substituted 7-[3-[(Ethylamino)methyl]-1-pyrrolidinyl]-6,8-difluoro-1,4-dihydro-4-oxo-3-quinolinecarboxylic Acids. New Quantitative Structure-Activity Relationships at $N_1$ for the Quinolone Antibacterials," Journal of Medicinal Chemistry, vol. 31, pp. 991-1001 (1988).

(Continued)

*Primary Examiner* — Kamal Saeed

(74) *Attorney, Agent, or Firm* — Finnegan, Henderson, Farabow, Garrett & Dunner, LLP

(57) ABSTRACT

The present invention provides a compound useful as a synthetic intermediate for an anti-HIV agent having an integrase inhibitory activity, and a production method thereof, and a production method of an anti-HIV agent using the synthetic intermediate. Specifically, for example, a compound represented by the formula (2'):

(2')

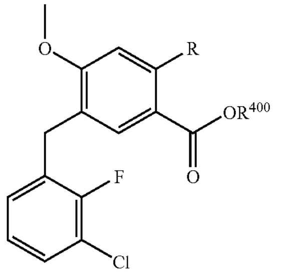

wherein R is a fluorine atom or a methoxy group, and $R^{400}$ is a hydrogen atom or a $C_1$-$C_4$ alkyl group, or a salt thereof, and a production method thereof, and a production method of an anti-HIV agent using the synthetic intermediate.

18 Claims, No Drawings

FOREIGN PATENT DOCUMENTS

| | | | |
|---|---|---|---|
| JP | 48-26772 | | 4/1973 |
| JP | 4-360872 | | 12/1992 |
| JP | 6-116241 | | 4/1994 |
| JP | 6-199835 | | 7/1994 |
| JP | 6-271568 | | 9/1994 |
| JP | 8-183775 | | 7/1996 |
| JP | 10-316570 | | 12/1998 |
| JP | 11-084556 | | 3/1999 |
| JP | 2002-293745 | | 10/2002 |
| JP | 2002-534416 | | 10/2002 |
| JP | 2002-534417 | | 10/2002 |
| JP | 2006-001927 | | 1/2006 |
| WO | WO 95/29891 | A1 | 11/1995 |
| WO | WO 97/38999 | | 10/1997 |
| WO | WO 98/34995 | A1 | 8/1998 |
| WO | WO 98/45269 | | 10/1998 |
| WO | WO 99/01434 | | 1/1999 |
| WO | WO 99/52857 | | 10/1999 |
| WO | WO 00/01714 | | 1/2000 |
| WO | WO 00/40561 | | 7/2000 |
| WO | WO 00/40563 | | 7/2000 |
| WO | WO 01/02385 | | 1/2001 |
| WO | WO 01/98275 | | 12/2001 |
| WO | WO 02/04422 | | 1/2002 |
| WO | WO 02/04444 | | 1/2002 |
| WO | WO 02/36734 | | 5/2002 |
| WO | WO 02/48113 | | 6/2002 |
| WO | WO 02/055079 | | 7/2002 |
| WO | WO 02/070486 | | 9/2002 |
| WO | WO 02/076939 | | 10/2002 |
| WO | WO 03/043992 | A1 | 5/2003 |
| WO | WO 2004/046115 | A1 | 6/2004 |
| WO | WO 2005/113508 | A1 | 12/2005 |
| WO | WO 2005/113509 | A1 | 12/2005 |
| WO | WO 2007/102499 | A1 | 9/2007 |
| WO | WO 2007/102512 | | 9/2007 |
| WO | WO 2008/033836 | A2 | 3/2008 |
| WO | WO 2009/036161 | A1 | 3/2009 |
| WO | WO 2009/089263 | | 7/2009 |

OTHER PUBLICATIONS

Extended European Search Report for European Patent Application No. 10011216.8, dated Feb. 15, 2011.

Gualtieri, F. et al., A Direct Metalation Approach to 2-Alkylthio-2,2-Diaryl Substituted Acetic Acids, SYNLETT, vol. 5, pp. 447-448 (1996).

Malamas, M.S. et al., "Design and synthesis of aryl diphenclic azoles as potent and selective estrogen receptor-βligands," J. Med. Chem. 2004, vol. 47, No. 21, pp. 5021-5040.

Perry, R.J., "Synthesis of Polyimides via the Palladium-Catalyzed Carbonylation of Bis(o-iodo Esters) and Diamines," Macromolecules, vol. 28, pp. 3509-3515 (1995).

Šulcová, V., "Effect of Derivatives of 3-Quinolinecarboxylic Acid on DNA Synthesis, Growth and Division in *Escherichia coli* 15 TAU," Folia Microbiologica, vol. 19, No. 4, pp. 281-291 (1974).

Zhurnal Organicheskoi Khimi 6,1, pp. 68-71 (1970).

Co-pending U.S. Appl. No. 12/281,921, filed Sep. 5, 2008.

International Search Report for Application No. PCT/JP2007/054348 dated Jun. 5, 2007.

International Search Report for Application No. PCT/JP2007/054311 dated Jun. 5, 2007.

Dinescu, L. et al., "Design of Photonic Liquid Crystal Materials: Synthesis and Evaluation of New Chiral Thioindigo Dopants Designed to Photomodulate the Spontaneous Polarization of Ferroelectric Liquid Crystals," J. Mater. Chem., vol. 9, No. 8, pp. 1679-1686 (1999).

Abdul-Ahad, P. et al., "Trends in Dehydrogenase Inhibitory Potencies of Some Quinolines, Using Quantum Chemical Indices," European Journal of Medicinal Chemistry, vol. 17, No. 4, pp. 301-306 (1982).

Baker, B. et al., "Irreversible Enzyme Inhibitors. 191. Hydrophobic Bonding to Some Dehydrogenases by 6-, 7-, or 8-Substituted-4-hydroxyquinoline-3-carboxylic acids," Journal of Medicinal Chemistry, vol. 15, No. 3, pp. 235-237 (1972).

Deprez, E. et al., "Mechanism of HIV-1 Integrase Inhibition by Styrylquinoline Derivatives In Vitro," Molecular Pharmacology, vol. 65, pp. 85-98 (2004).

Guidelines for the Use of Antiretroviral Agents in HIV-Infected Adults and Adolescent, pp. i-iii and 1-111 (Aug. 13, 2001).

Hirao, I. et al., "Studies on the Synthesis of Quinoline Compounds," Memoirs Kyushu Inst. Tech. (Eng.), vol. 14, pp. 13-16 (1984).

Hirao, I. et al., "Antibacterial Activities of Oxodihydroquinoline Carboxylic Acid Derivatives," Memoirs Dept. of Engineering, vol. 14, pp. 21-32 (1990).

International Search Report for Application No. PCT/JP03/14773 dated Feb. 10, 2004, 4 pages.

Search Report from Austrian Patent Office for Application No. 200404137-2 dated Apr. 3, 2006, 6 pages.

Stefancich, G. et al., "Antibacterial and Antifungal Agents. VII. Synthesis of (1-pyrryl) methylquinolonecarboxylic Acids," Edizionie Scientifica, vol. 42, No. 1, pp. 3-16 (1987).

Vincent, K. et al., "Characterization of Human Immunodeficiency Virus Type I Integrase Expressed in *Eschericia coli* and Analysis of Variants with Amino-Terminal Mutations," Journal of Virology, vol. 67, pp. 425-437 (1993).

Walton, L. et al., "In Vitro Cleavable-Complex Assay to Monitor Antimicrobial Potency of Quinolones," Antimicrobial Agents and Chemotherapy, vol. 32, No. 7, pp. 1086-1089 (1988).

West, A., Solid State Chemistry and Its Applications, pp. 358 and 365, John Wiley & Sons, New York (1988).

Yoshimoto, M. et al., "Correlation Analysis of Baker's studies on Enzyme Inhibition. 2. Chymotrypsin, Trypsin, Thymidine Phosphorylase. Uridine Phosphorylase, Thymidilate Synthetase, Cytosine Nucleoside Deaminase, Dihydrofolate Reductase,Malate, Glutamate, Lactate, and Glyceraldehyde-Phosphate Dehydrogenase," Journal of Medicinal Chemistry, vol. 19, No. 1, pp. 71-98 (1976).

Non-Final Rejection mailed Nov. 22, 2005, in U.S. Appl. No. 10/492,833, 11 pages.

Notice of Allowance mailed Apr. 27, 2006, in U.S. Appl. No. 10/492,833, 4 pages.

Notice of Allowance mailed Jul. 17,2006, in U.S. Appl. No. 10/492,833, 4 pages.

Notice of Allowance mailed Jul. 24, 2006, in U.S. Appl. No. 10/492,833, 2 pages.

Requirement for Restriction/Election mailed Sep. 11, 2009, in U.S. Appl. No. 11/446,128, 8 pages.

Non-Final Rejection mailed Jan. 28, 2010, in U.S. Appl. No. 11/446,128, 11 pages.

Non-Final Rejection mailed May 19, 2010, in U.S. Appl. No. 11/446,128, 11 pages.

Final Rejection mailed Sep. 8, 2010, in U.S. Appl. No. 11/446,128, 14 pages.

Advisory Action mailed Jan. 11, 2011, in U.S. Appl. No. 11/446,128, 3 pages.

Pre-Appeal Conference Decision mailed Apr. 11, 2011, in U.S. Appl. No. 11/446,128, 2 pages.

Non-Final Rejection mailed May 23, 2011, in U.S. Appl. No. 11/446,128, 11 pages.

Final Rejection mailed Oct. 26, 2011, in U.S. Appl. No. 11/446,128, 14 pages.

Ex Parte Quayle Action mailed Mar. 14, 2012, in U.S. Appl. No, 11/446,128, 4 pages.

Notice of Allowance and Applicant Initiated Interview Summary mailed Mar. 20, 2012, in U.S. Appl. No. 11/446,128, 9 pages.

Requirement for Restriction/Election mailed May 10, 2011, in U.S. Appl. No. 12/281,921, 8 pages.

Requirement for Restriction/Election mailed Jul. 21, 2011, in U.S. Appl. No. 12/281,921, 8 pages.

Ex Parte Quayle Action mailed Mar. 22, 2012, in U.S. Appl. No. 12/281.921, 7 pages.

* cited by examiner

METHOD FOR PRODUCING 4-OXOQUINOLINE COMPOUND

TECHNICAL FIELD OF THE INVENTION

The present invention relates to a compound useful as a synthetic intermediate for an anti-HIV agent having an integrase inhibitory activity and a production method thereof. Moreover, the present invention relates to a production method of an anti-HIV agent, which uses the synthetic intermediate, and the like.

BACKGROUND OF THE INVENTION

Patent reference 1 discloses a production method of a 4-oxoquinoline compound represented by the formula [III]:

[III]

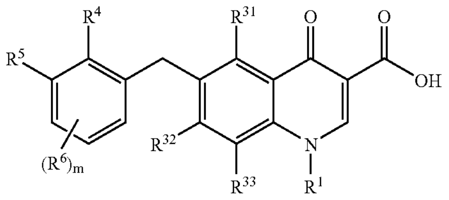

wherein each symbol is as described in the patent reference 1 (hereinafter sometimes to be abbreviated as compound [III]), and specifically, the following production methods are known.

Production Method 1-1 (See Patent Reference 1: Page 67)

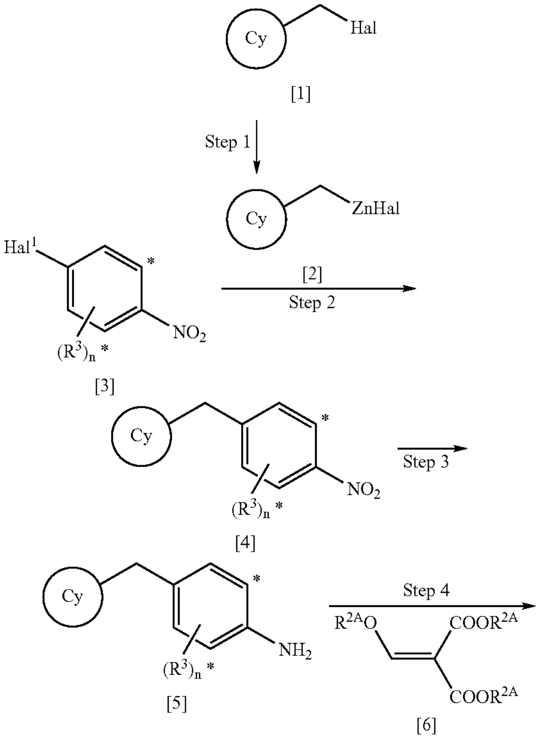

-continued

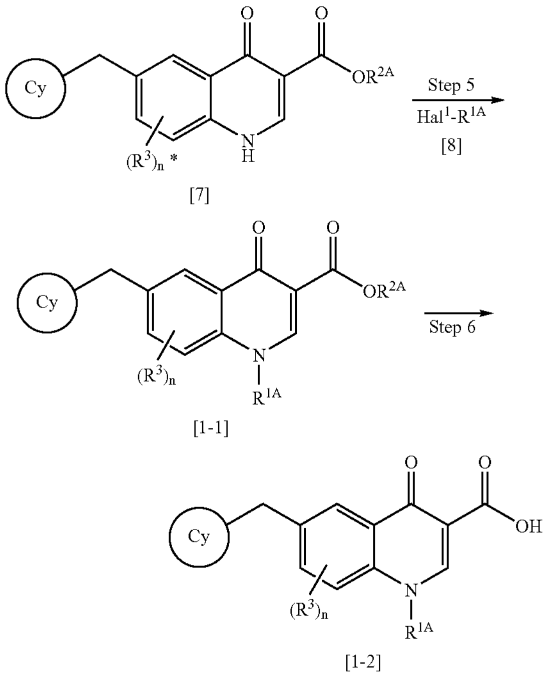

Each symbol in the scheme is as described in the patent reference 1.

This production method is also described in patent reference 2, page 64 (each symbol in the scheme is also described in patent reference 2).

Production Method 1-2 Example of Production Method Using Compound [9] Having a Hydroxyl-Protecting Group (See Patent Reference 1: Page 71)

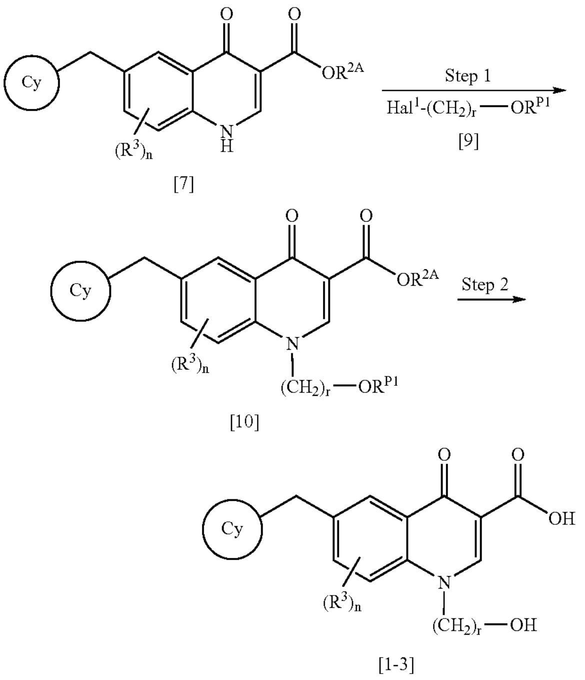

Each symbol in the scheme is as described in patent reference 1.

This production method is also described in patent reference 2, page 68 (each symbol in the scheme is also described in patent reference 2).

Production Method 2-1 (See Patent Reference 1: Page 72)

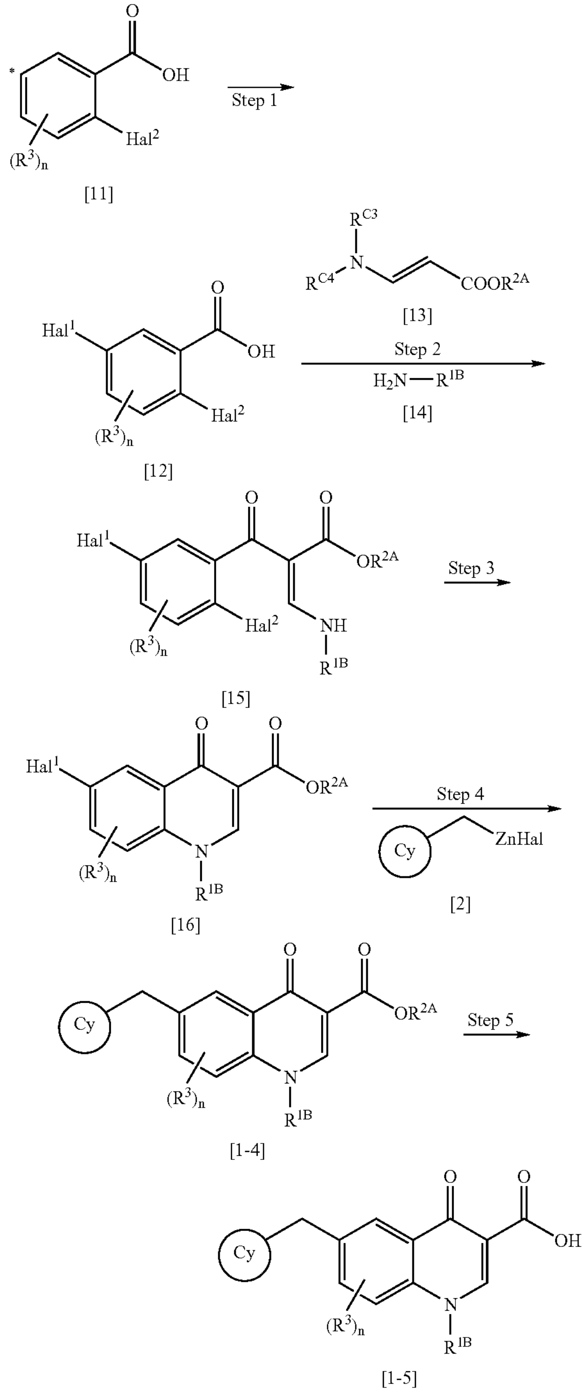

Each symbol in the scheme is as described in patent reference 1.

This production method is also described in patent reference 2, page 69 (each symbol in the scheme is also described in patent reference 2).

Production Method 2-2 Example of Production Method Including Introduction-Removal Step of Hydroxyl-Protecting Group (See Patent Reference 1: page 74)

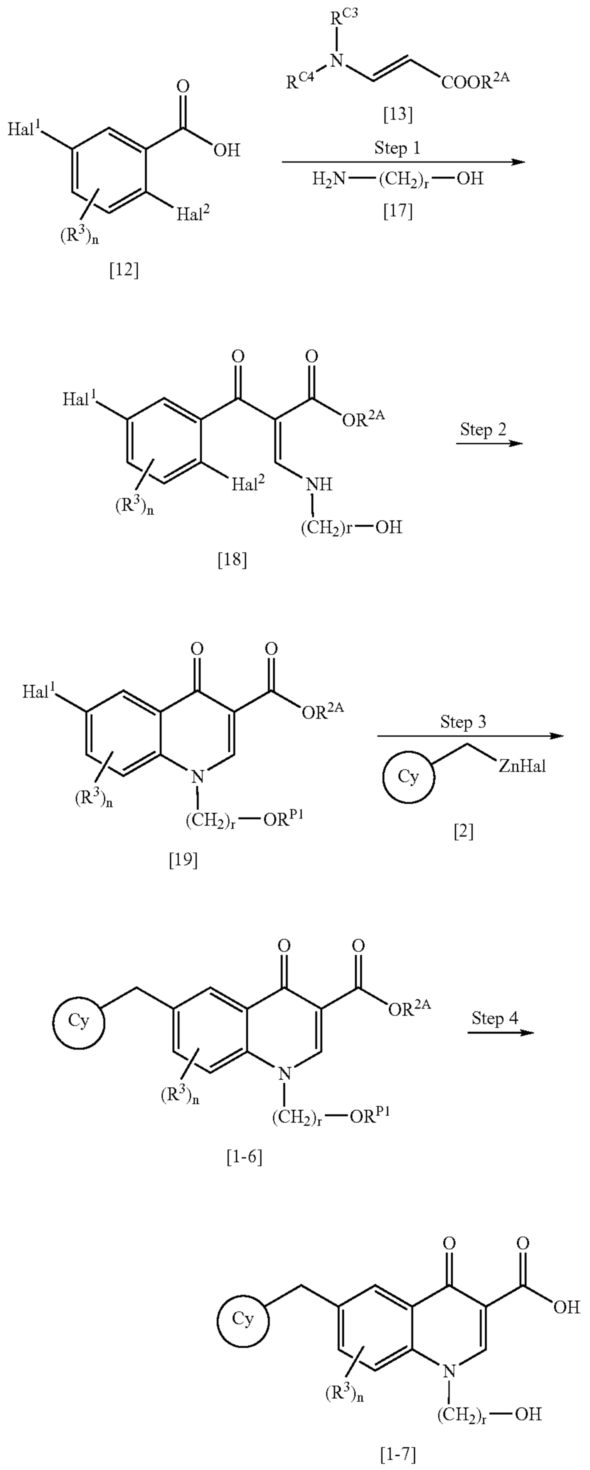

Each symbol in the scheme is as described in patent reference 1.

This production method is also described in patent reference 2, page 72 (each symbol in the scheme is also described in patent reference 2).

Production Method 3 (See Patent Reference 1: Page 76)

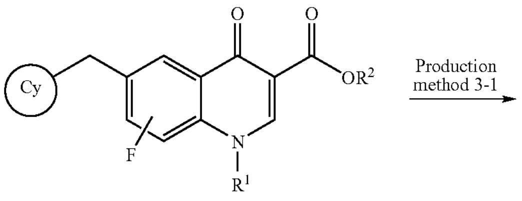

[21]

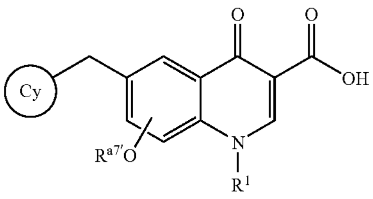

[1-8]

Each symbol in the scheme is as described in patent reference 1.

This production method is also described in patent reference 2, page 74 (each symbol in the scheme is also described in patent reference 2).

Production Method 4 (See Patent Reference 1: Page 77)

Examples of production methods of the above-mentioned compound [12] are more concretely given below.

Each symbol in the scheme is as described in patent reference 1.

Production Method 5 (See Pate Reference 1: Page 79)

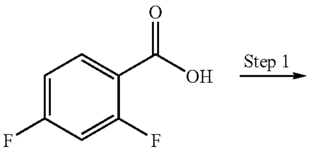

[29]

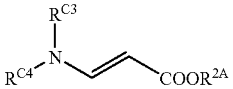

[13]

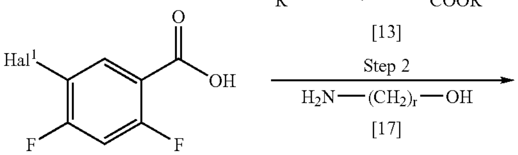

[17]

[30]

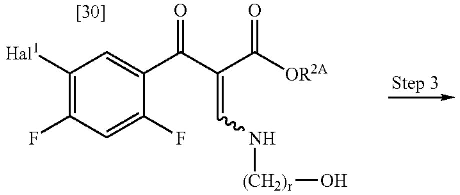

[31]

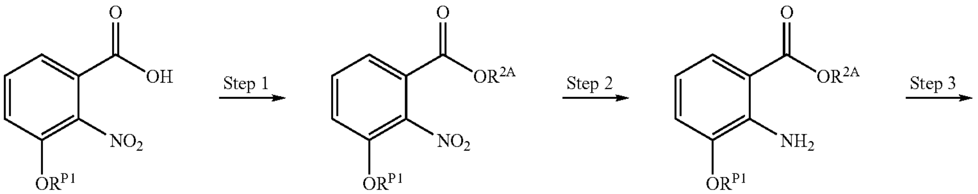

[22] [23] [24]

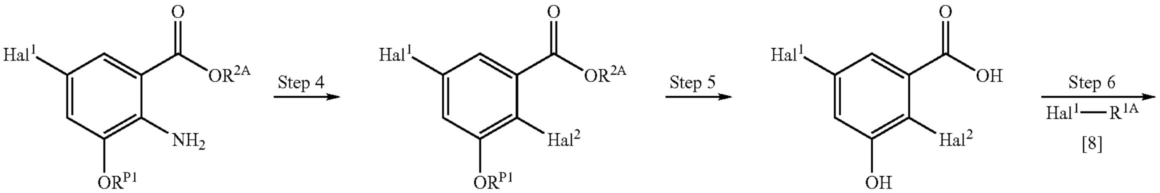

[8]

[25] [26] [27]

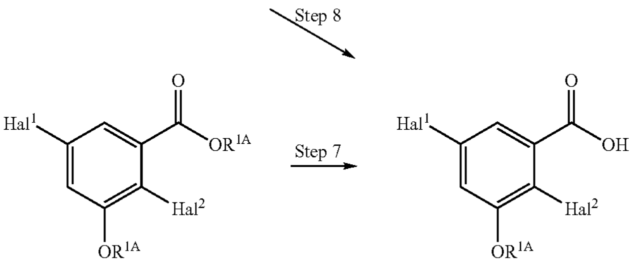

[28] [12']

-continued

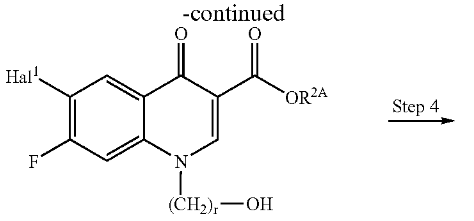

[32]

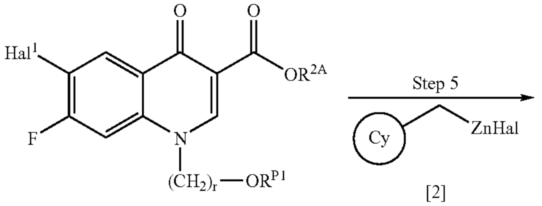

[33]

[2]

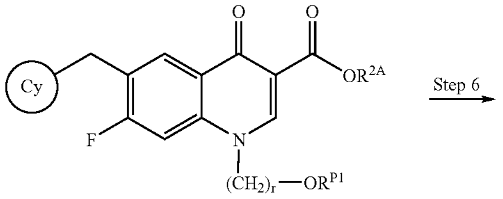

[1-10]

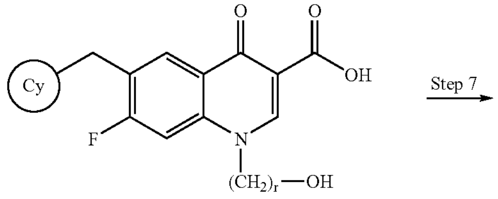

[1-11]

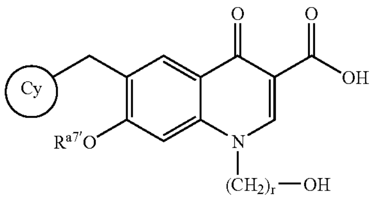

[1-12]

Each symbol in the scheme is as described in patent reference 1.

The production method is also described in patent reference 2, page 78 (each symbol in the scheme is also described in patent reference 2).

The above-mentioned production method 1-1 and production method 2-1 respectively relate to a production method of compound [1-2] and compound [1-5] corresponding to the above-mentioned compound [III].

The production method 1-2, production method 2-2 and production method 5 show production examples including introduction-removal of hydroxyl-protecting group.

In addition, production method 3 discloses a method for introducing a substituent after formation of a 4-oxoquinoline ring, and production method 4 describes examples of production method of compound [12] more specifically.

Moreover, patent reference 1 discloses, as one of the compounds particularly useful as anti-HIV agents from among compounds [III], 6-(3-chloro-2-fluorobenzyl)-1-((S)-1-hydroxymethyl-2-methylpropyl)-7-methoxy-4-oxo-1,4-dihydroquinoline)-3-carboxylic acid (hereinafter sometimes to be abbreviated as compound (10)) and a production method thereof.

Specifically, Example 4-32 in patent reference 1 describes the following production example.

In addition, production of 2,4-difluoro-5-iodobenzoic acid (starting material) is disclosed in patent reference 1, Example 4-33, step 1.

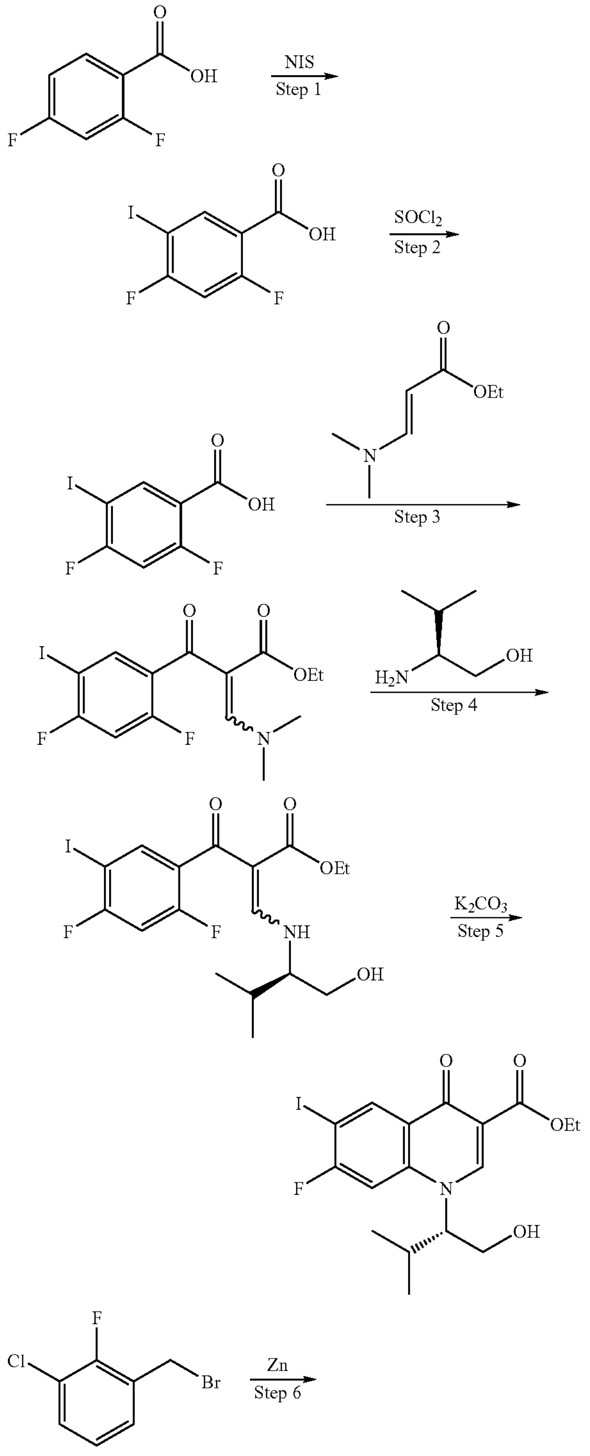

-continued

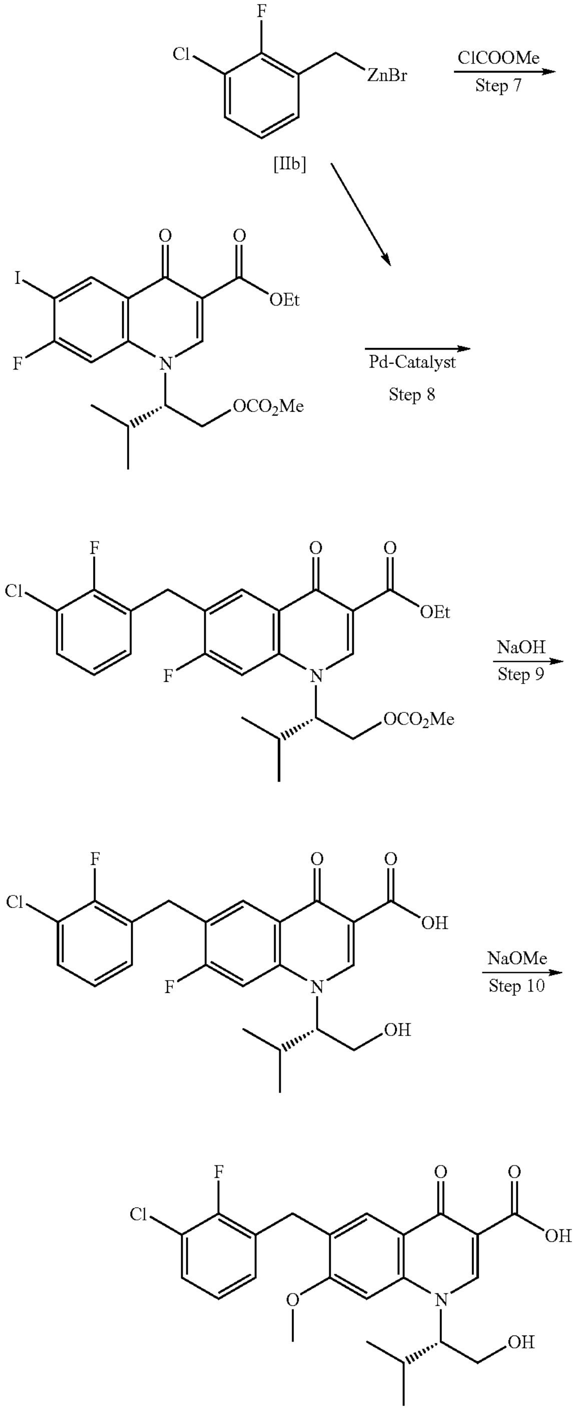

(10)

wherein NIS is N-iodosuccinimide, Catalyst is a catalyst, and the other symbols are as defined in patent reference 1.

This production method is also described in patent reference 2, page 112, Reference Example 9.

As a production method similar to this production method, patent reference 3 describes, at page 23, Example 2-1, a production method wherein the hydroxyl-protecting group is a tert-butyldimethylsilyl group. Further, patent reference 3, page 12, Reference Example 1; page 17, Example 1 and page 39, Example 2-4 describe a method of directly producing compound (10) from a compound wherein a hydroxyl-protecting group is tert-butyldimethylsilyl group, as shown below.

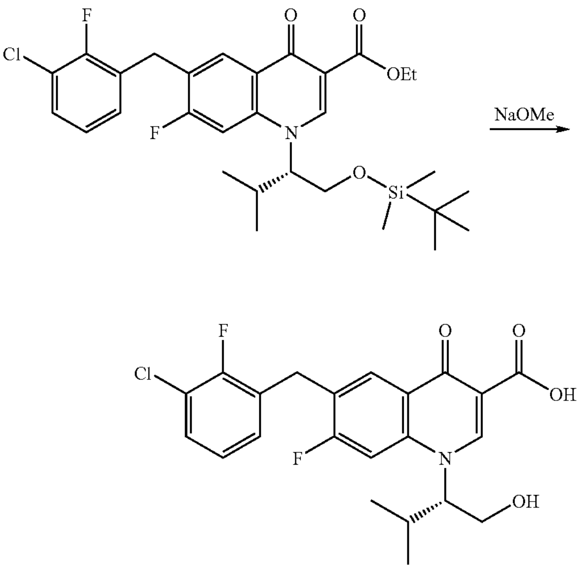

(10)

Moreover, patent reference 1, page 81, Reference Example 1, or patent reference 2, page 80, Reference Example 1 disclose that 2,3-dichlorobenzylzinc chloride which is an analog of 3-chloro-2-fluorobenzylzinc bromide produced in the above-mentioned step 6, can be produced in the same manner from 2,3-dichlorobenzyl chloride.

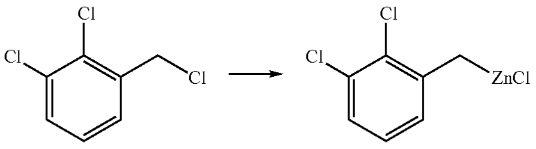

Patent reference 3 discloses a production method of compound (10).

Specifically, patent reference 3 describes the following production example in Example 2-2, page 28.

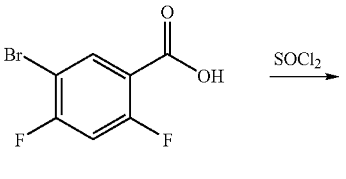

-continued
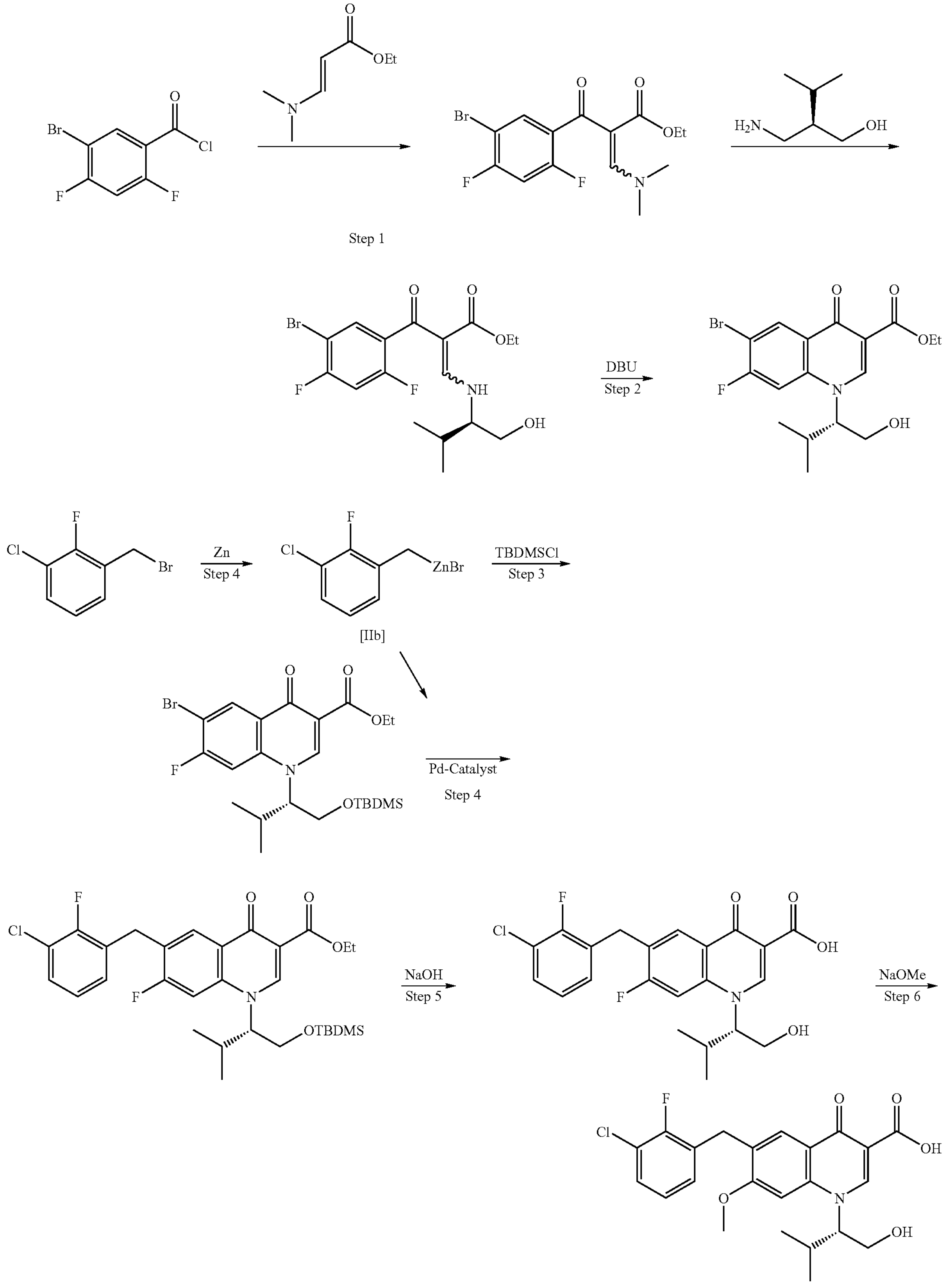
(10)

wherein DBU is 1,8-diazabicyclo[5.4.0]undecene, Catalyst is a catalyst, and the other symbols are as defined in patent reference 3.

While patent reference 1, patent reference 2 and patent reference 3 disclose production methods of compound (10), the production methods embrace the following aspects.

In the final step (alkoxylation, particularly methoxylation), a dimer is by-produced depending on the base to be used. In this event, a removal step of the by-produced dimer is further necessary, which decreases the yield greatly.

When sodium fluoride by-produced in the final step (alkoxylation, particularly methoxylation) is acidified in the treatment step, hydrofluoric acid is produced and corrodes the production facility. Thus, a removal operation of sodium fluoride is essential and the operation is complicated.

There is a concern about an unfavorable influence of hydrofluoric acid produced in the ring-closing step on the production facility, and therefore, the method is not of a level satisfactory as an industrial production method.

Removal of the product by-produced in a reaction to insert compound [IIb] is complicated (since alkylzinc derivative is used together with a palladium catalyst, an operation to remove zinc salt and palladium salt as impurities is necessary and the operation is complicated).

Plural operations are necessary to protect hydroxyl group with methyl chloroformate in a preliminary step of the reaction to insert compound [IIb], and to deprotect the group in a later step, and the operation is complicated.

A step using 3-chloro-2-fluorobenzyl bromide for the production of compound [IIb] is not beneficial for industrial production, since the compound shows high tearing property.

The above-mentioned production method including these steps is associated with many aspects to be improved for industrial production, and the development of a more superior production method of compound (10) is desired.

In addition, while non-patent reference 1 describes the following benzoic acid compound and the like, it provides no description of the compound (2') of the present invention to be explained in detail in the following.

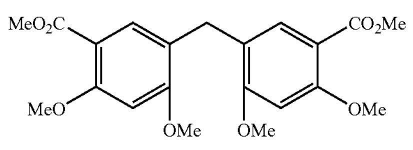 [SMILES: COC(=O)c1cc(Cc2cc(C(=O)OC)c(OC)cc2OC)c(OC)cc1OC]

Moreover, patent reference 4 describes, in the ring-closing reaction for forming a 4-oxoquinoline skeleton, a production example of a 4-oxoquinoline skeleton from the following acrylic acid ester and the like. However, it provides no description of the production method of compound (9) from compound (7), or compound (8) from compound (6-B) of the present invention to be explained in detail in the following.

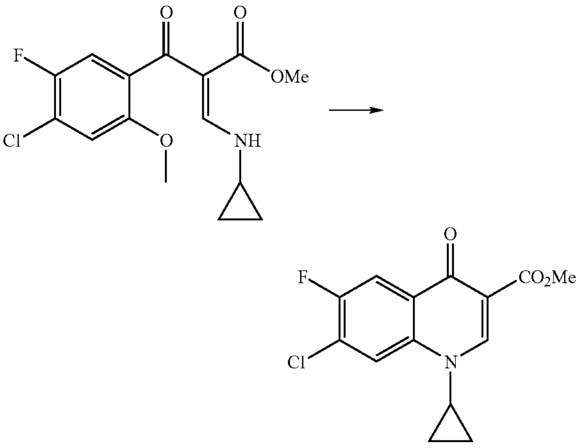

Patent reference 5 (see page 11, compound 2-12) describes the following benzoic acid compound [A] and the like as photosensitive materials. However, it provides no description of the compound (2') of the present invention to be explained in detail in the following.

[A]

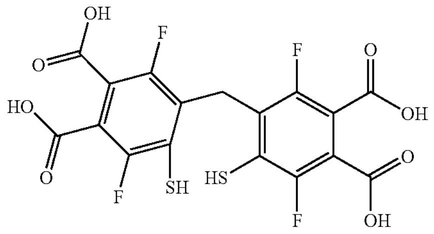

Moreover, non-patent reference 2 describes the following benzoic acid compound [B] and the like (see scheme 2). However, it provides no description of the compound (2') of the present invention to be explained in detail in the following.

[B]

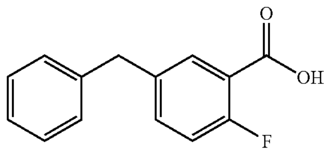

In addition, non-patent reference 3 describes the following benzoic acid compounds [C] and [D] and the like (see page 3512, compounds 10 and 12). However, it provides no description of the compound (2') of the present invention to be explained in detail in the following.

[C]

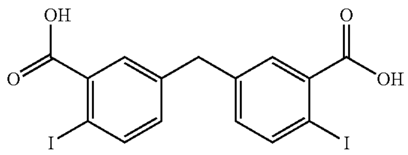

-continued

[D]

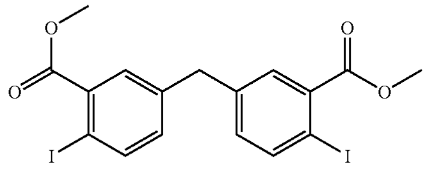

[Patent reference 1] WO 04/046115

[Patent reference 2] WO 05/113509

[Patent reference 3] WO 05/113508

[Patent reference 4] U.S. Pat. No. 4,695,646 (column 15, line 40)

[Patent reference 5] JP-A-11-84556

[Non-patent reference 1] Zhurnal Organicheskoi Khimii, vol. 6, number 1, pages 68-71, 1970 (page 70, 3)

[Non-patent reference 2] Synlett, vol. 5, p. 447-448, 1996

[Non-patent reference 3] Macromolecules, vol. 28, p. 3509-3515, 1995

DISCLOSURE OF THE INVENTION

Problems to be Solved by the Invention

An object of the present invention is to provide a compound useful as a synthetic intermediate for an anti-HIV agent having an integrase inhibitory activity and a production method thereof, and a production method of an anti-HIV agent using the synthetic intermediate.

Means of Solving the Problems

In view of the above-mentioned object, the present inventors have conducted intensive studies in an attempt to find an improved production method of the above-mentioned compound [III], particularly compound (10), and found that a compound represented by the formula (2') (hereinafter sometimes to be abbreviated as compound (2')) or a salt thereof is useful as a synthetic intermediate therefor, which resulted in the completion of the present invention.

The formula (2'):

(2')

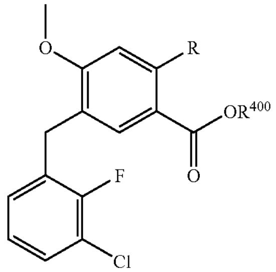

wherein R is a fluorine atom or a methoxy group, and $R^{400}$ is a hydrogen atom or a $C_1$-$C_4$ alkyl group.

More specifically, the present invention is as shown in the following [1]-[45].

[1] A compound represented by the formula (2'):

(2')

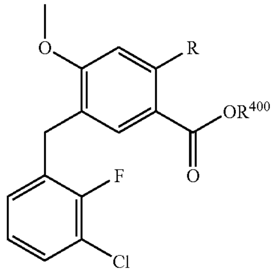

wherein R is a fluorine atom or a methoxy group, and $R^{400}$ is a hydrogen atom or a $C_1$-$C_4$ alkyl group (hereinafter sometimes to be abbreviated as compound (2')), or a salt thereof.

[2] The compound of the above-mentioned [1], wherein R is a methoxy group, or a salt thereof.

[3] Use of a compound represented by the formula (8-1):

(8-1)

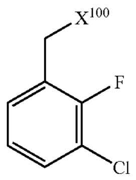

wherein $X^{100}$ is a halogen atom (hereinafter sometimes to be abbreviated as compound (8-1)) for the production of a compound represented by the formula (2'):

(2')

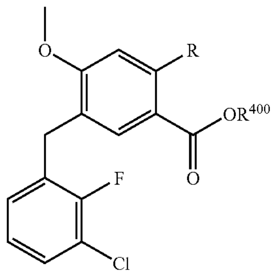

wherein R is a fluorine atom or a methoxy group, and $R^{400}$ is a hydrogen atom or a $C_1$-$C_4$ alkyl group, or a salt thereof.

[4] Use of a compound represented by the formula (8-1):

(8-1)

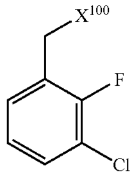

wherein $X^{100}$ is a halogen atom, and a compound represented by the formula (2-1):

(2-1)

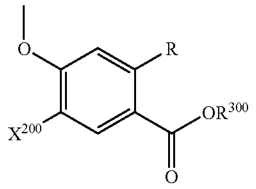

wherein R is a fluorine atom or a methoxy group, $R^{300}$ is a $C_1$-$C_4$ alkyl group, and $X^{200}$ is a halogen atom (hereinafter sometimes to be abbreviated as compound (2-1)) in the presence of a metal atom $M^1$, for the production of a compound represented by the formula (2'):

(2')

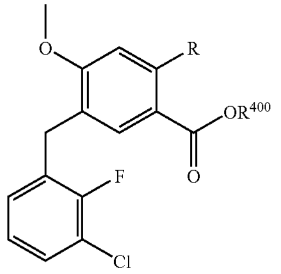

wherein R is a fluorine atom or a methoxy group, and $R^{400}$ is a hydrogen atom or a $C_1$-$C_4$ alkyl group,
or a salt thereof.

[5] Use of a compound represented by the formula (2'):

(2')

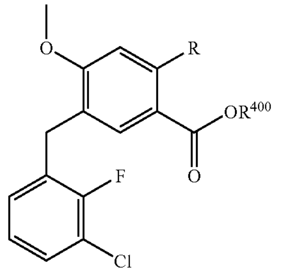

wherein R is a fluorine atom or a methoxy group, and $R^{400}$ is a hydrogen atom or a $C_1$-$C_4$ alkyl group,
or a salt thereof, for the production of compound (10):

(10)

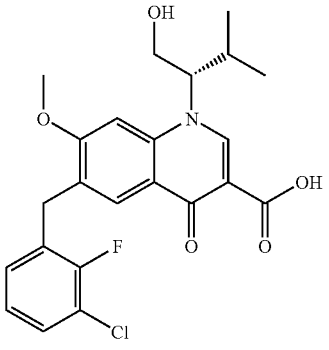

or a salt thereof.

[6] Use of a compound represented by the formula (8-1):

(8-1)

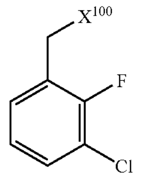

wherein $X^{100}$ is a halogen atom, a compound represented by the formula (2-1):

(2-1)

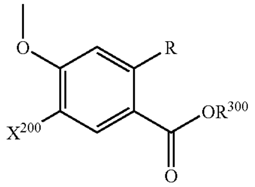

wherein R is a fluorine atom or a methoxy group, $R^{300}$ is a $C_1$-$C_4$ alkyl group, and $X^{200}$ is a halogen atom, and a compound represented by the formula (2'):

(2')

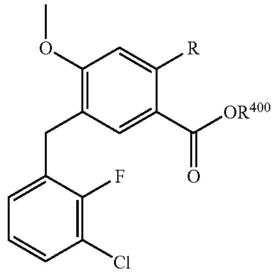

wherein R is a fluorine atom or a methoxy group, and $R^{400}$ is a hydrogen atom or a $C_1$-$C_4$ alkyl group, or a salt thereof, for the production of compound (10):

(10)

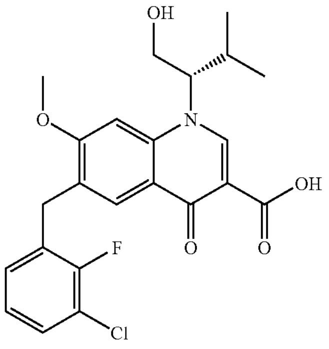

or a salt thereof.

[7] Use of a compound represented by the formula (2-2):

(2-2)

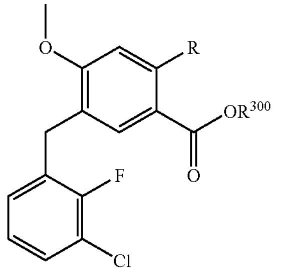

wherein R is a fluorine atom or a methoxy group, and $R^{300}$ is a $C_1$-$C_4$ alkyl group (hereinafter sometimes to be abbreviated as compound (2-2)), a compound represented by the formula (2-3):

(2-3)

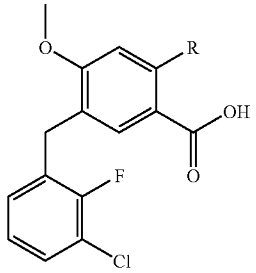

wherein R is a fluorine atom or a methoxy group (hereinafter sometimes to be abbreviated as compound (2-3)), or a salt thereof, a compound represented by the formula (3):

(3)

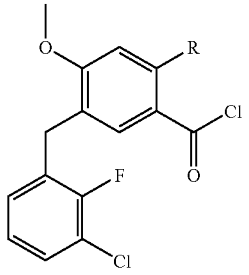

wherein R is a fluorine atom or a methoxy group (hereinafter sometimes to be abbreviated as compound (3)), a compound represented by the formula (4):

(4)

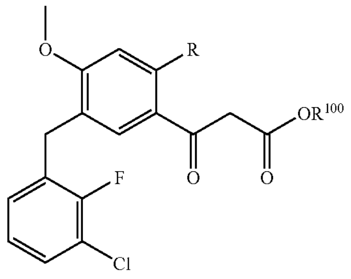

wherein R is a fluorine atom or a methoxy group, and $R^{100}$ is a $C_1$-$C_4$ alkyl group (hereinafter sometimes to be abbreviated as compound (4)), or a salt thereof, a compound represented by the formula (5):

(5)

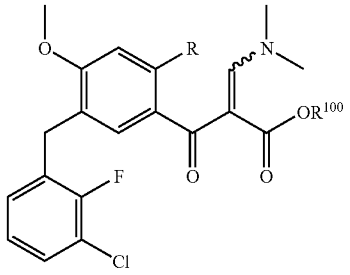

wherein R is a fluorine atom or a methoxy group, and $R^{100}$ is a $C_1$-$C_4$ alkyl group (hereinafter sometimes to be abbreviated as compound (5)), and a compound represented by the formula (6):

(6)

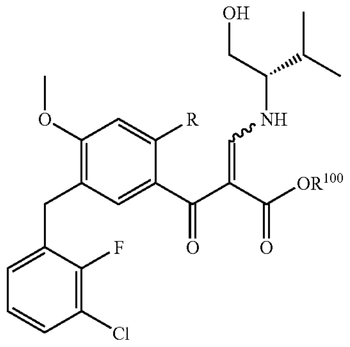

wherein R is a fluorine atom or a methoxy group, and $R^{100}$ is a $C_1$-$C_4$ alkyl group (hereinafter sometimes to be abbreviated as compound (6)), for the production of compound (10):

(10)

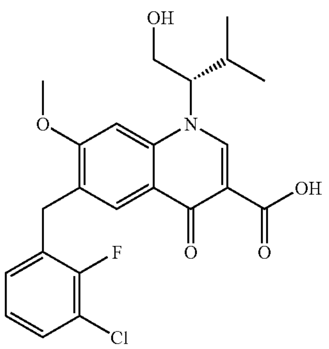

or a salt thereof.

[8] Use of a compound represented by the formula (2-2-A):

(2-2-A)

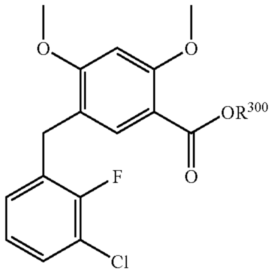

wherein $R^{300}$ is a $C_1$-$C_4$ alkyl group (hereinafter sometimes to be abbreviated as compound (2-2-A)), compound (2-3-A):

(2-3-A)

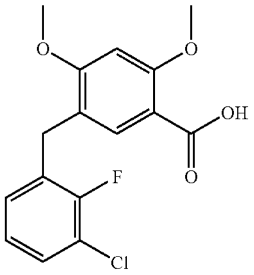

or a salt thereof, compound (3-A):

(3-A)

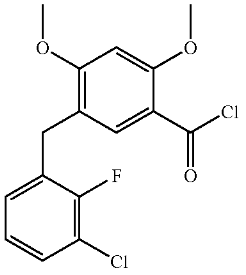

a compound represented by the formula (4-A):

(4-A)

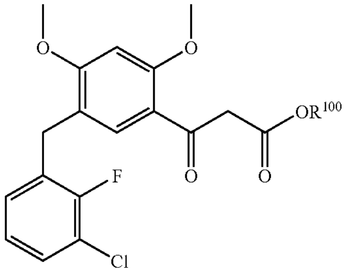

wherein $R^{100}$ is a $C_1$-$C_4$ alkyl group (hereinafter sometimes to be abbreviated as compound (4-A)), or a salt thereof, a compound represented by the formula (5-A):

(5-A)

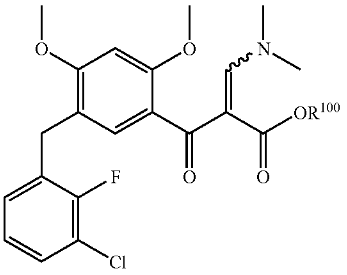

wherein $R^{100}$ is a $C_1$-$C_4$ alkyl group (hereinafter sometimes to be abbreviated as compound (5-A)), a compound represented by the formula (6-A):

(6-A)

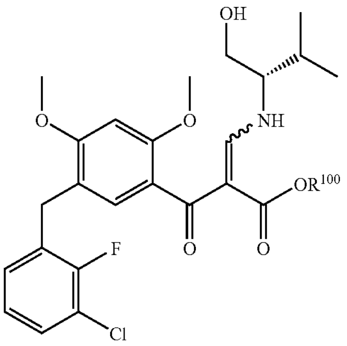

wherein $R^{100}$ is a $C_1$-$C_4$ alkyl group (hereinafter sometimes to be abbreviated as compound (6-A)), a compound represented by the formula (7):

(7)

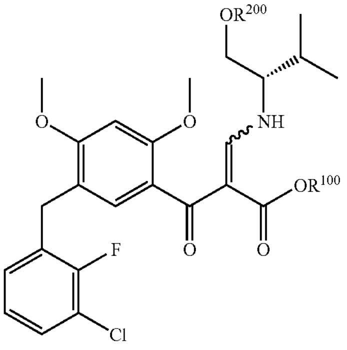

wherein $R^{100}$ is a $C_1$-$C_4$ alkyl group, and $R^{200}$ is a hydroxyl-protecting group (hereinafter sometimes to be abbreviated as compound (7)), and a compound represented by the formula (9):

(9)

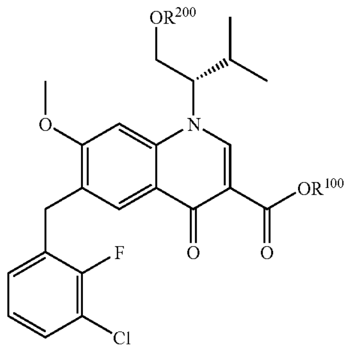

wherein $R^{100}$ is a $C_1$-$C_4$ alkyl group, and $R^{200}$ is a hydroxyl-protecting group (hereinafter sometimes to be abbreviated as compound (9)), for the production of compound (10):

(10)

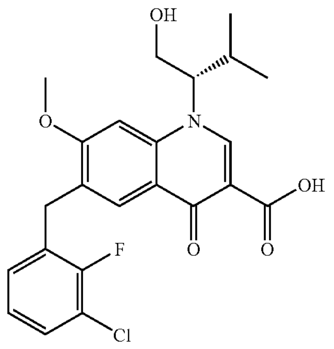

or a salt thereof.

[9] Use of a compound represented by the formula (2-2-B):

(2-2-B)

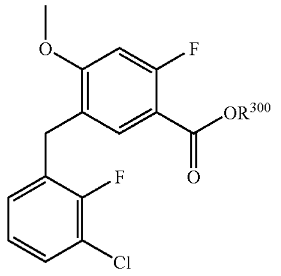

wherein $R^{300}$ is a $C_1$-$C_4$ alkyl group (hereinafter sometimes to be abbreviated as compound (2-2-B)), compound (2-3-B):

(2-3-B)

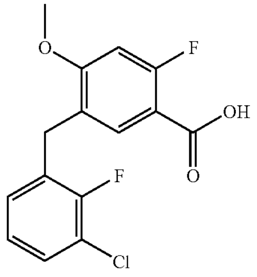

or a salt thereof, compound (3-B):

(3-B)

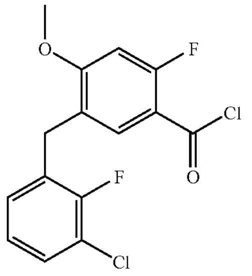

a compound represented by the formula (4-B):

(4-B)

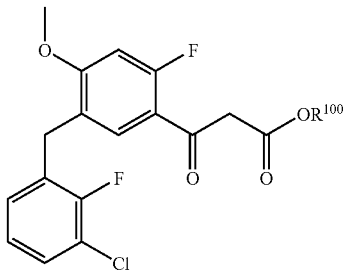

wherein $R^{100}$ is a $C_1$-$C_4$ alkyl group (hereinafter sometimes to be abbreviated as compound (4-B)), or a salt thereof, a compound represented by the formula (5-B):

(5-B)

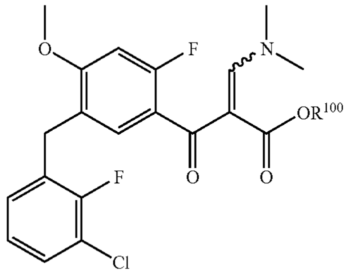

wherein $R^{100}$ is a $C_1$-$C_4$ alkyl group (hereinafter sometimes to be abbreviated as compound (5-B)), a compound represented by the formula (6-B):

(6-B)

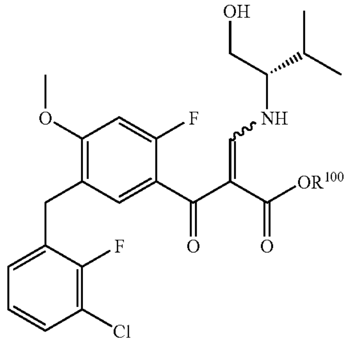

wherein $R^{100}$ is a $C_1$-$C_4$ alkyl group (hereinafter sometimes to be abbreviated as compound (6-B)), and a compound represented by the formula (8):

(8)

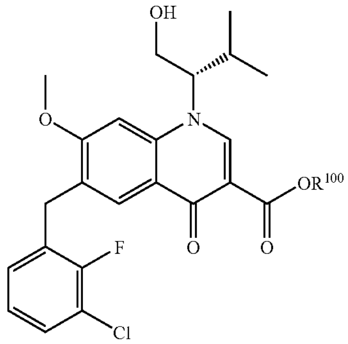

wherein $R^{100}$ is a $C_1$-$C_4$ alkyl group (hereinafter sometimes to be abbreviated as compound (8)), for the production of compound (10):

(10)

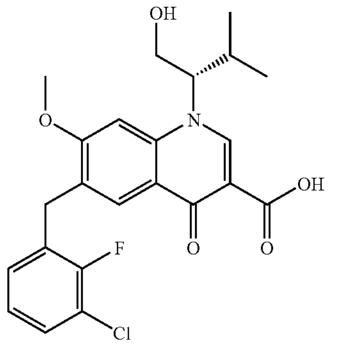

or a salt thereof.

[10] Use of a compound represented by the formula (1):

(1)

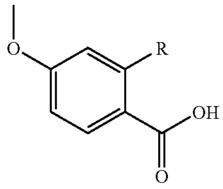

wherein R is a fluorine atom or a methoxy group (hereinafter sometimes to be abbreviated as compound (1)), or a salt thereof, a compound represented by the formula (2):

(2)

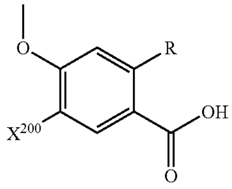

wherein R is a fluorine atom or a methoxy group, and $X^{200}$ is a halogen atom (hereinafter sometimes to be abbreviated as compound (2)), or a salt thereof, a compound represented by the formula (2-1):

(2-1)

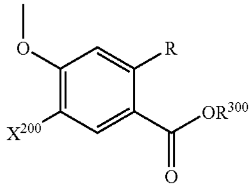

wherein R is a fluorine atom or a methoxy group, $R^{300}$ is a $C_1$-$C_4$ alkyl group, and $X^{200}$ is a halogen atom, a compound represented by the formula (2-2):

(2-2)

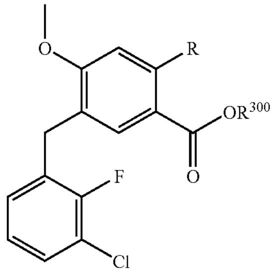

wherein R is a fluorine atom or a methoxy group, and $R^{300}$ is a $C_1$-$C_4$ alkyl group, a compound represented by the formula (2-3):

(2-3)

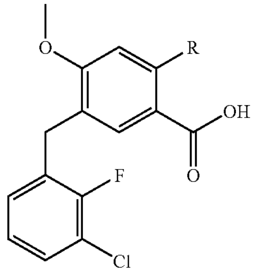

wherein R is a fluorine atom or a methoxy group, or a salt thereof, a compound represented by the formula (3):

(3)

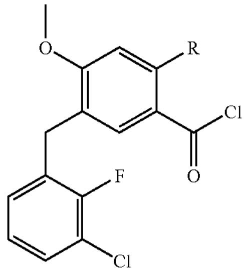

wherein R is a fluorine atom or a methoxy group, a compound represented by the formula (4):

(4)

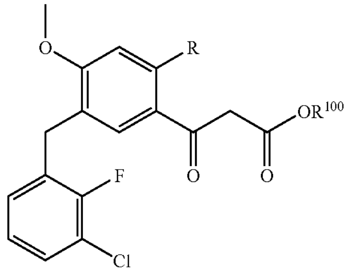

wherein R is a fluorine atom or a methoxy group, and $R^{100}$ is a $C_1$-$C_4$ alkyl group, or a salt thereof, a compound represented by the formula (5):

(5)

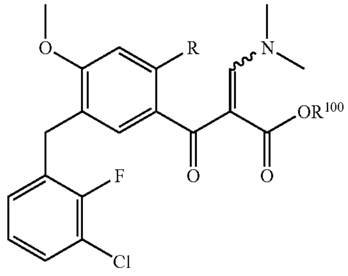

wherein R is a fluorine atom or a methoxy group, and $R^{100}$ is a $C_1$-$C_4$ alkyl group, and a compound represented by the formula (6):

(6)

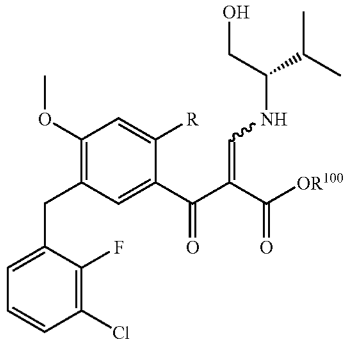

wherein R is a fluorine atom and a methoxy group, and $R^{100}$ is a $C_1$-$C_4$ alkyl group, for the production of compound (10):

(10)

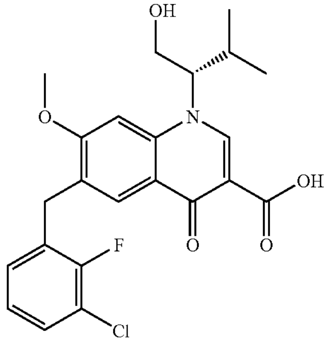

or a salt thereof.

[11] Use of compound (1-A):

(1-A)

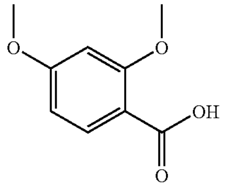

or a salt thereof, a compound represented by the formula (2-A):

(2-A)

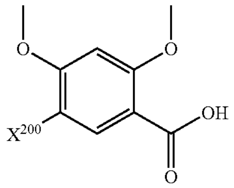

wherein $X^{200}$ is a halogen atom (hereinafter sometimes to be abbreviated as compound (2-A)), or a salt thereof, a compound represented by the formula (2-1-A):

(2-1-A)

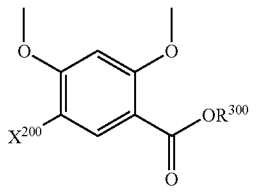

wherein $R^{300}$ is a $C_1$-$C_4$ alkyl group, and $X^{200}$ is a halogen atom (hereinafter sometimes to be abbreviated as compound (2-1-A)), a compound represented by the formula (2-2-A):

(2-2-A)

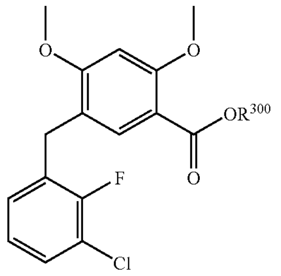

wherein $R^{300}$ is a $C_1$-$C_4$ alkyl group, compound (2-3-A):

(2-3-A)

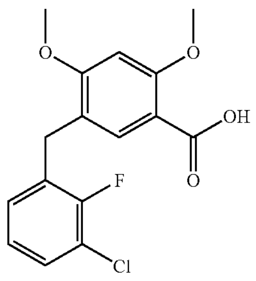

or a salt thereof, compound (3-A):

(3-A)

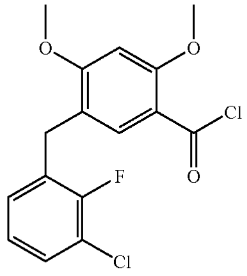

a compound represented by the formula (4-A):

(4-A)

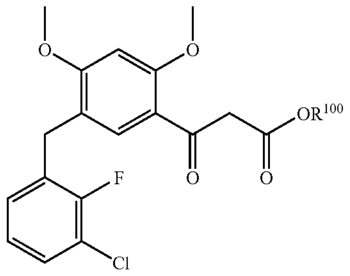

wherein $R^{100}$ is a $C_1$-$C_4$ alkyl group, or a salt thereof, a compound represented by the formula (5-A):

(5-A)

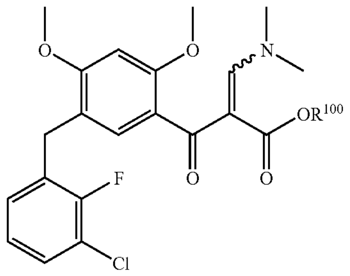

wherein $R^{100}$ is a $C_1$-$C_4$ alkyl group, a compound represented by the formula (6-A):

(6-A)

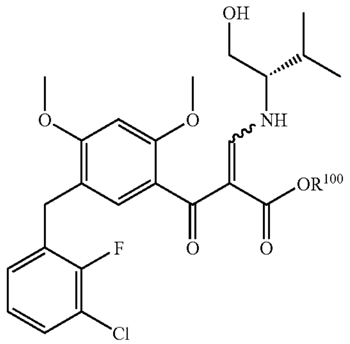

wherein $R^{100}$ is a $C_1$-$C_4$ alkyl group, a compound represented by the formula (7):

(7)

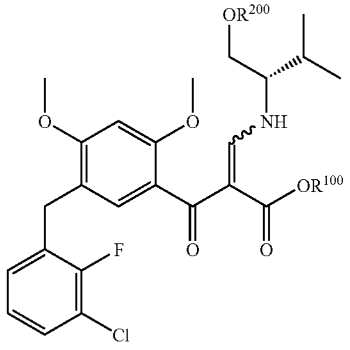

wherein $R^{100}$ is a $C_1$-$C_4$ alkyl group, and $R^{200}$ is a hydroxyl-protecting group, and a compound represented by the formula (9):

(9)

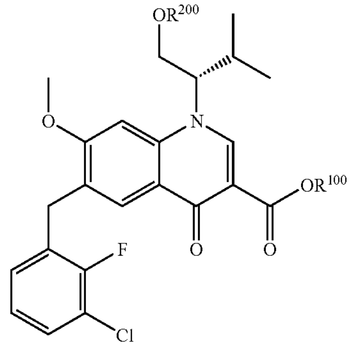

wherein $R^{100}$ is a $C_1$-$C_4$ alkyl group, and $R^{200}$ is a hydroxyl-protecting group, for the production of compound (10):

(10)

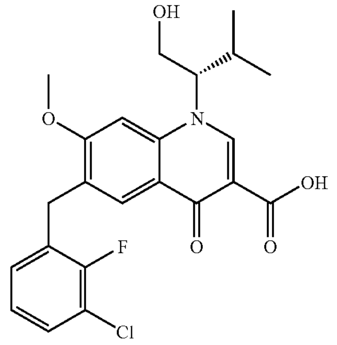

or a salt thereof.

[12] Use of compound (1-B):

(1-B)

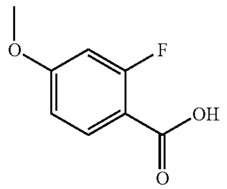

or a salt thereof, a compound represented by the formula (2-B):

(2-B)

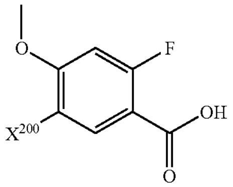

wherein $X^{200}$ is a halogen atom (hereinafter sometimes to be abbreviated as compound (2-B)), or a salt thereof, a compound represented by the formula (2-1-B):

(2-1-B)

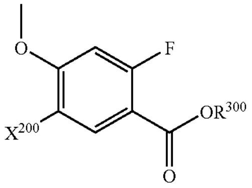

wherein $R^{300}$ is a $C_1$-$C_4$ alkyl group, and $X^{200}$ is a halogen atom (hereinafter sometimes to be abbreviated as compound (2-1-B)), a compound represented by the formula (2-2-B):

(2-2-B)

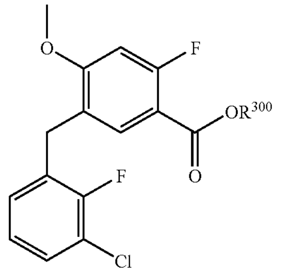

wherein $R^{300}$ is a $C_1$-$C_4$ alkyl group, compound (2-3-B):

(2-3-B)

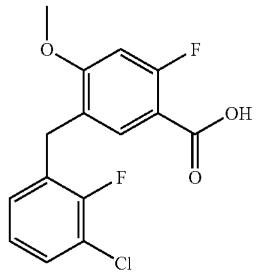

or a salt thereof, compound (3-B):

(3-B)

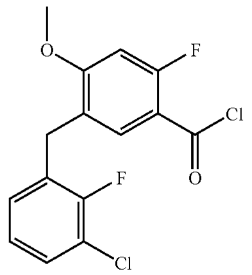

a compound represented by the formula (4-B):

(4-B)

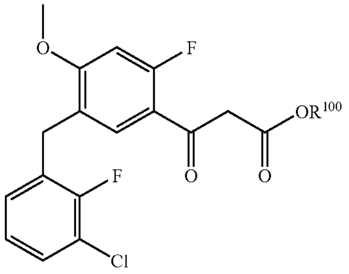

wherein $R^{100}$ is a $C_1$-$C_4$ alkyl group, or a salt thereof, a compound represented by the formula (5-B):

(5-B)

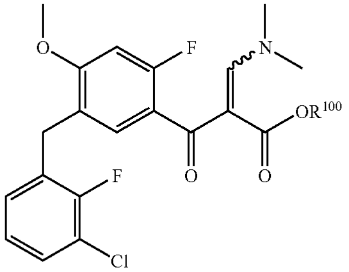

wherein $R^{100}$ is a $C_1$-$C_4$ alkyl group, a compound represented by the formula (6-B):

(6-B)

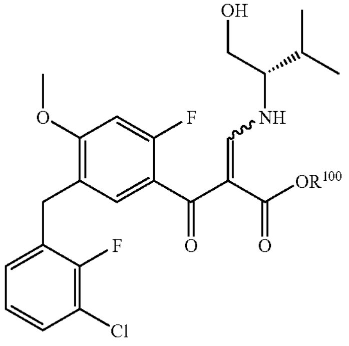

wherein $R^{100}$ is a $C_1$-$C_4$ alkyl group, and a compound represented by the formula (8):

(8)

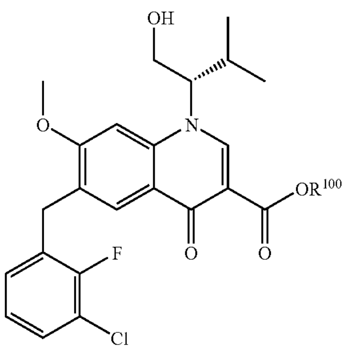

wherein $R^{100}$ is a $C_1$-$C_4$ alkyl group, for the production of compound (10):

(10)

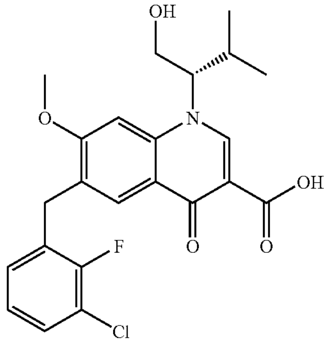

or a salt thereof.

[13] A method of producing a compound represented by the formula (2'):

(2')

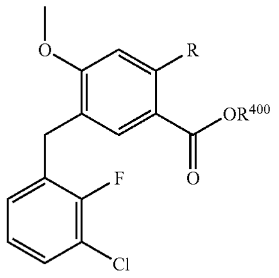

wherein R is a fluorine atom or a methoxy group, and $R^{400}$ is a hydrogen atom or a $C_1$-$C_4$ alkyl group, or a salt thereof, which comprises reacting a compound represented by the formula (8-1):

(8-1)

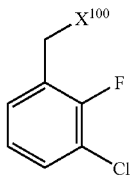

wherein $X^{100}$ is a halogen atom, with a compound represented by the formula (2-1):

(2-1)

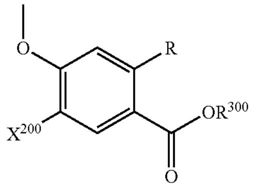

wherein R is a fluorine atom or a methoxy group, $R^{300}$ is a $C_1$-$C_4$ alkyl group, and $X^{200}$ is a halogen atom, in the presence of a metal atom $M^1$.

[14] A method of producing the following compound (10), or a salt thereof, comprising producing compound (10):

(10)

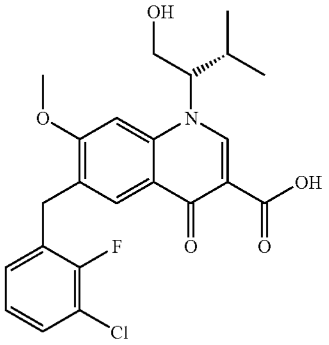

or a salt thereof from a compound represented by the formula (2'):

(2')

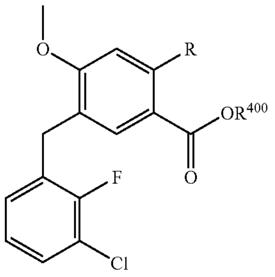

wherein R is a fluorine atom or a methoxy group, and $R^{400}$ is a hydrogen atom or a $C_1$-$C_4$ alkyl group, or a salt thereof.

[15] A method of producing compound (10):

(10)

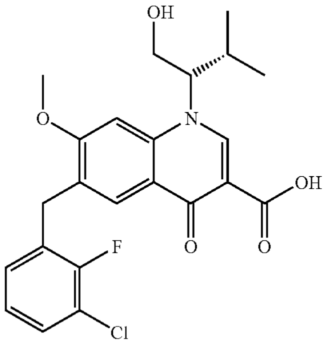

or a salt thereof, which comprises a step of producing compound (2-3-A):

(2-3-A)

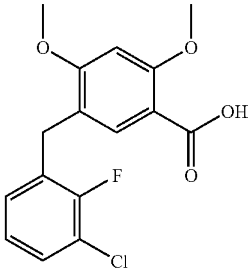

or a salt thereof, from a compound represented by the formula (2-2-A):

(2-2-A)

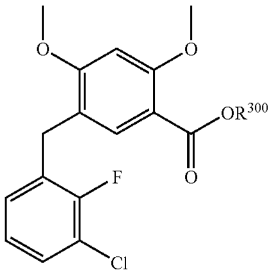

wherein $R^{300}$ is a $C_1$-$C_4$ alkyl group;

a step of producing compound (3-A):

(3-A)

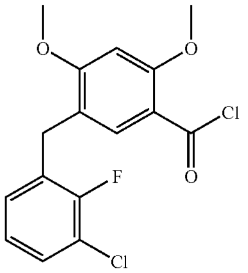

from the above-mentioned compound (2-3-A) or a salt thereof; a step of producing a compound represented by the formula (4-A):

(4-A)

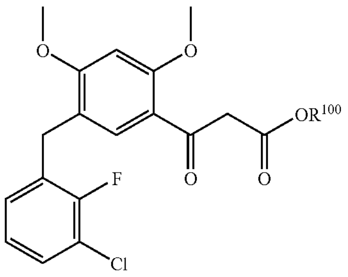

wherein $R^{100}$ is a $C_1$-$C_4$ alkyl group, or a salt thereof, from the above-mentioned compound (3-A);

a step of producing a compound represented by the formula (5-A):

(5-A)

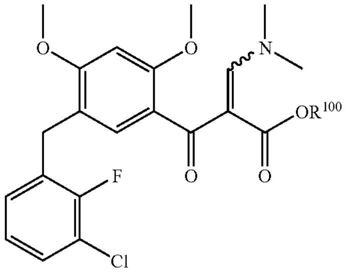

wherein $R^{100}$ is a $C_1$-$C_4$ alkyl group, from the above-mentioned compound (4-A) or a salt thereof;

a step of producing a compound represented by the formula (6-A):

(6-A)

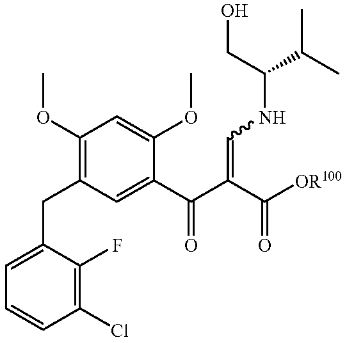

wherein $R^{100}$ is a $C_1$-$C_4$ alkyl group, from the above-mentioned compound (5-A);

a step of producing a compound represented by the formula (7):

(7)

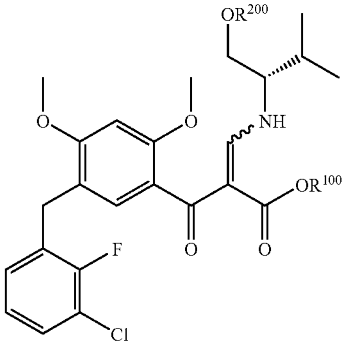

wherein $R^{100}$ is a $C_1$-$C_4$ alkyl group, and $R^{200}$ is a hydroxyl-protecting group, from the above-mentioned compound (6-A);

a step of producing a compound represented by the formula (9):

(9)

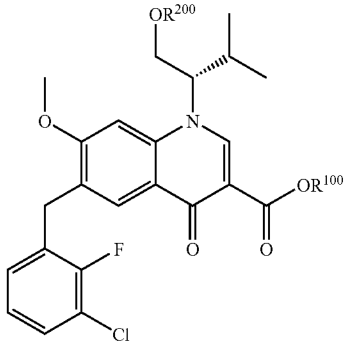

wherein $R^{100}$ is a $C_1$-$C_4$ alkyl group, and $R^{200}$ is a hydroxyl-protecting group, from the above-mentioned compound (7); and a step of producing the above-mentioned compound (10) or a salt thereof from the above-mentioned compound (9).

[16] The production method of the above-mentioned [15], which further comprises a step of producing a compound represented by the formula (2-A):

(2-A)

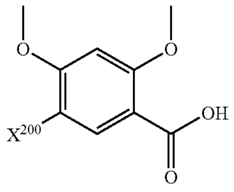

wherein $X^{200}$ is a halogen atom, or a salt thereof, from compound (1-A):

(1-A)

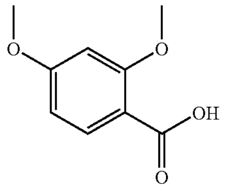

or a salt thereof;

a step of producing a compound represented by the formula (2-1-A):

(2-1-A)

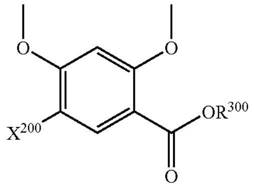

wherein $R^{300}$ is a $C_1$-$C_4$ alkyl group, and $X^{200}$ is a halogen atom, from the above-mentioned compound (2-A) or a salt thereof; and a step of producing a compound represented by the formula (2-2-A):

(2-2-A)

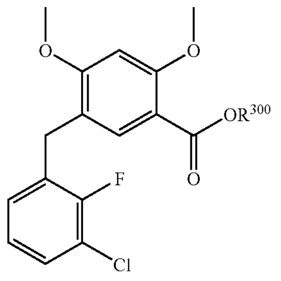

wherein $R^{300}$ is a $C_1$-$C_4$ alkyl group, from the above-mentioned compound (2-1-A).

[17] A method of producing compound (10):

(10)

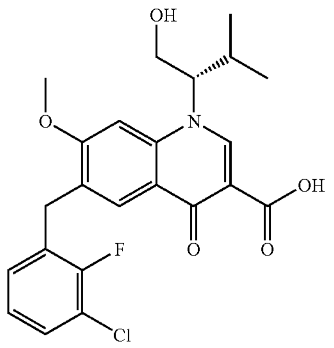

or a salt thereof, which comprises a step of producing compound (2-3-B):

(2-3-B)

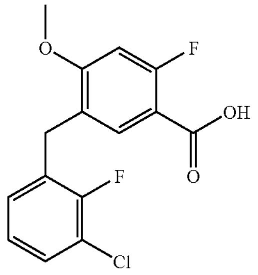

or a salt thereof, from a compound represented by the formula (2-2-B):

(2-2-B)

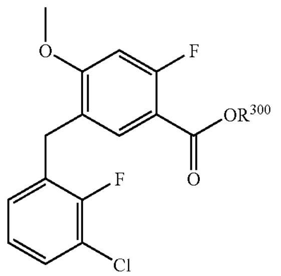

wherein $R^{300}$ is a $C_1$-$C_4$ alkyl group;

a step of producing compound (3-B):

(3-B)

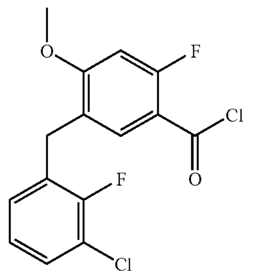

from the above-mentioned compound (2-3-B) or a salt thereof;

a step of producing a compound represented by the formula (4-B):

(4-B)

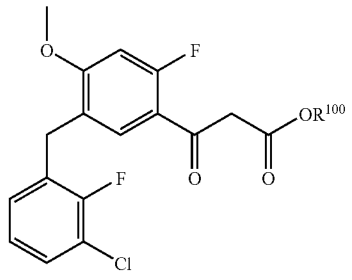

wherein $R^{100}$ is a $C_1$-$C_4$ alkyl group, or a salt thereof, from the above-mentioned compound (3-B);

a step of producing a compound represented by the formula (5-B):

(5-B)

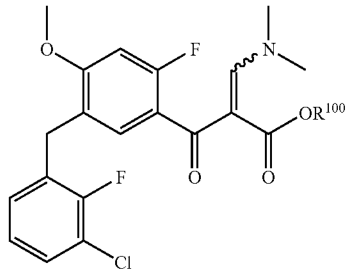

wherein $R^{100}$ is a $C_1$-$C_4$ alkyl group, from the above-mentioned compound (4-B) or a salt thereof;

a step of producing a compound represented by the formula (6-B):

(6-B)

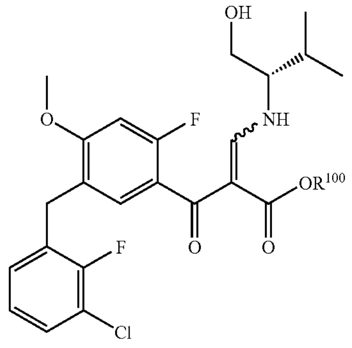

wherein $R^{100}$ is a $C_1$-$C_4$ alkyl group, from the above-mentioned compound (5-B);

a step of producing a compound represented by the formula (8):

(8)

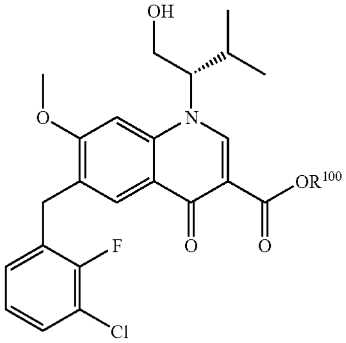

wherein $R^{100}$ is a $C_1$-$C_4$ alkyl group, from the above-mentioned compound (6-B); and a step of producing the above-mentioned compound (10) or a salt thereof from the above-mentioned compound (8).

[18] The production method of the above-mentioned [17], which further comprises a step of producing a compound represented by the formula (2-B):

(2-B)

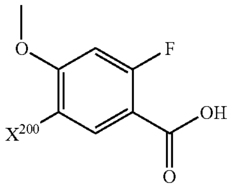

wherein $X^{200}$ is a halogen atom, or a salt thereof, from compound (1-B):

(1-B)

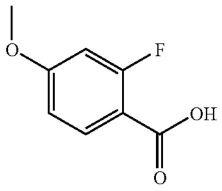

or a salt thereof;

a step of producing a compound represented by the formula (2-1-B):

(2-1-B)

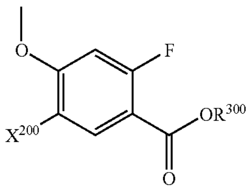

wherein $R^{300}$ is a $C_1$-$C_4$ alkyl group, and $X^{200}$ is a halogen atom, from the above-mentioned compound (2-B) or a salt thereof; and a step of producing a compound represented by the formula (2-2-B):

(2-2-B)

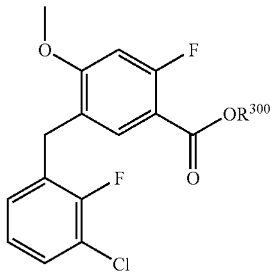

wherein $R^{300}$ is a $C_1$-$C_4$ alkyl group, from the above-mentioned compound (2-1-B).

[19] A compound represented by the formula (2-B):

(2-B)

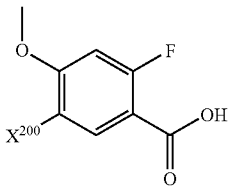

wherein $X^{200}$ is a halogen atom, or a salt thereof.

[20] A compound represented by the formula (2-1):

(2-1)

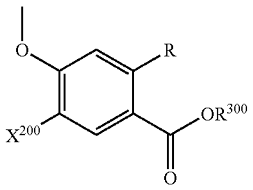

wherein R is a fluorine atom or a methoxy group, $R^{300}$ is a $C_1$-$C_4$ alkyl group, and $X^{200}$ is a halogen atom.

[21] A compound represented by the formula (3):

(3)

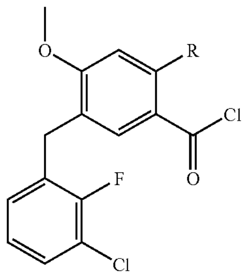

wherein R is a fluorine atom or a methoxy group.

[22] A compound represented by the formula (4):

(4)

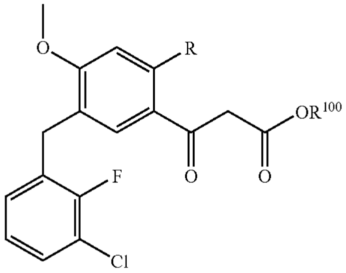

wherein R is a fluorine atom or a methoxy group, and $R^{100}$ is a $C_1$-$C_4$ alkyl group, or a salt thereof.

[23] A compound represented by the formula (4-1)

(4-1)

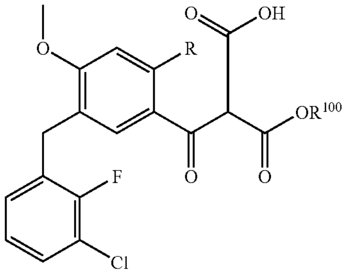

wherein R is a fluorine atom or a methoxy group, and $R^{100}$ is a $C_1$-$C_4$ alkyl group (hereinafter sometimes to be abbreviated as compound (4-1)), or a salt thereof.

A compound represented by the formula (4-2-B):

(4-2-B)

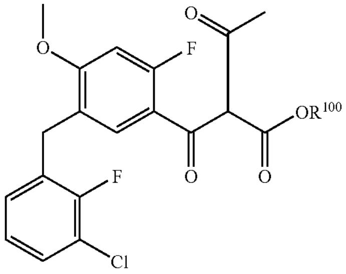

wherein $R^{100}$ is a $C_1$-$C_4$ alkyl group (hereinafter sometimes to be abbreviated as compound (4-2-B)), or a salt thereof.

[25] Use of a compound represented by the formula (4-1):

(4-1)

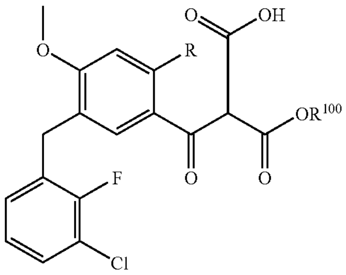

wherein R is a fluorine atom or a methoxy group, and $R^{100}$ is a $C_1$-$C_4$ alkyl group, or a salt thereof, for the production of a compound represented by the formula (4):

(4)

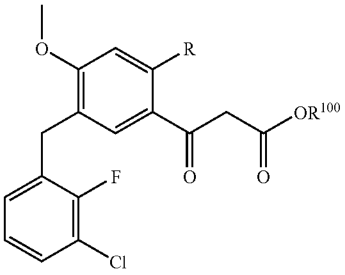

wherein R is a fluorine atom or a methoxy group, and $R^{100}$ is a $C_1$-$C_4$ alkyl group, or a salt thereof.

[26] Use of a compound represented by the formula (4-2-B):

(4-2-B)

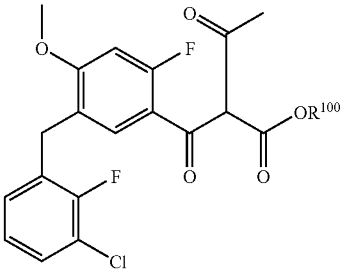

wherein $R^{100}$ is a $C_1$-$C_4$ alkyl group, or a salt thereof, for the production of a compound represented by the formula (4-B):

(4-B)

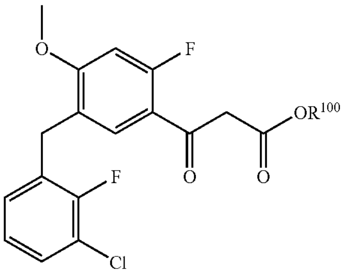

wherein $R^{100}$ is a $C_1$-$C_4$ alkyl group, or a salt thereof.

[27] Use of a compound represented by the formula (3):

(3)

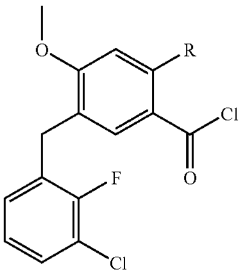

wherein R is a fluorine atom or a methoxy group, and a compound represented by the formula (4-1):

(4-1)

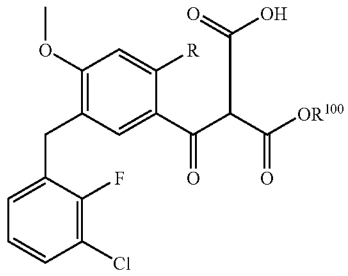

wherein R is a fluorine atom or a methoxy group, and $R^{100}$ is a $C_1$-$C_4$ alkyl group (hereinafter sometimes to be abbreviated as compound (4-1)), or a salt thereof, for the production of a compound represented by the formula (4):

(4)

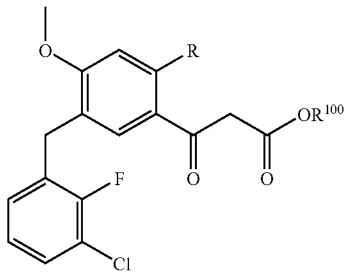

wherein R is a fluorine atom or a methoxy group, and $R^{100}$ is a $C_1$-$C_4$ alkyl group, or a salt thereof.

[28] Use of compound (3-B):

(3-B)

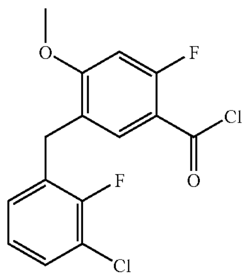

and a compound represented by the formula (4-2-B):

(4-2-B)

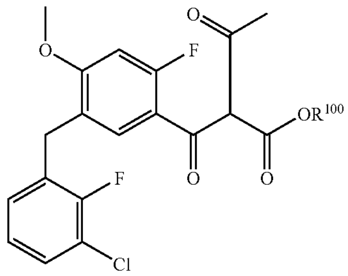

wherein $R^{100}$ is a $C_1$-$C_4$ alkyl group, or a salt thereof, for the production of a compound represented by the formula (4-B):

(4-B)

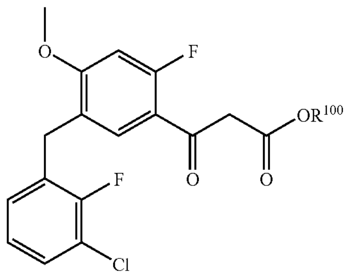

wherein $R^{100}$ is a $C_1$-$C_4$ alkyl group, or a salt thereof.

[29] A compound represented by the formula (5):

(5)

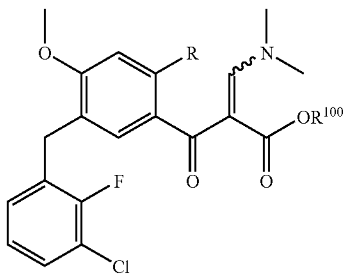

wherein R is a fluorine atom or a methoxy group, and $R^{100}$ is a $C_1$-$C_4$ alkyl group.

[30] A compound represented by the formula (6):

(6)

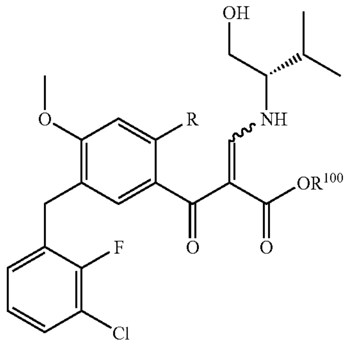

wherein R is a fluorine atom or a methoxy group, and $R^{100}$ is a $C_1$-$C_4$ alkyl group.

[31] A compound represented by the formula (7):

(7)

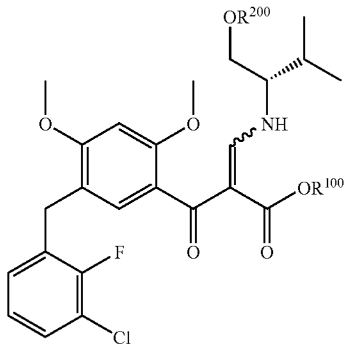

wherein $R^{100}$ is a $C_1$-$C_4$ alkyl group, and $R^{200}$ is a hydroxyl-protecting group.

[32] A compound represented by the formula (9):

(9)

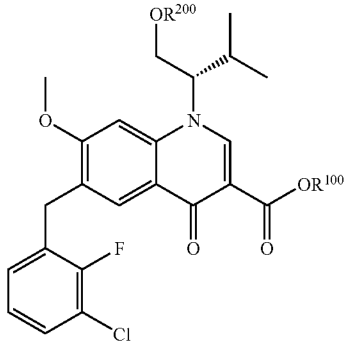

wherein $R^{100}$ is a $C_1$-$C_4$ alkyl group, and $R^{200}$ is a hydroxyl-protecting group.

[33] A compound represented by the formula (8):

(8)

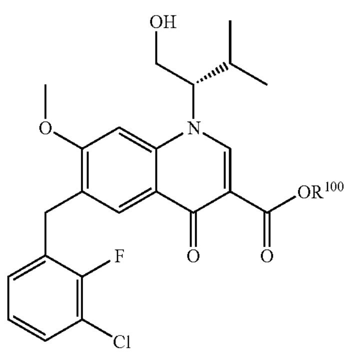

wherein $R^{100}$ is a $C_1$-$C_4$ alkyl group.

[34] A compound represented by the formula [I]:

[I]

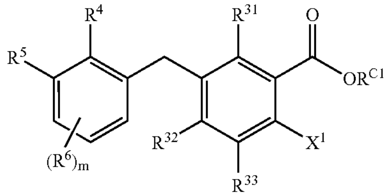

wherein $R^{C1}$ is a hydrogen atom or a carboxyl-protecting group, $X^1$ is a halogen atom, $R^4$ and $R^6$ are the same or different and each is a group selected from group A:

cyano group, phenyl group, nitro group, halogen atom, $C_{1-4}$ alkyl group, halo $C_{1-4}$ alkyl group, halo $C_{1-4}$ alkyloxy group, —$OR^{a1}$, —$SR^{a1}$, —$NR^{a1}R^{a2}$, —$CONR^{a1}R^{a2}$, —$SO_2NR^{a1}R^{a2}$, —$COR^{a3}$, —$NR^{a1}COR^{a3}$, —$SO_2R^{a3}$, —$NR^{a1}SO_2R^{a3}$, —$COOR^{a1}$ and —$NR^{a2}COOR^{a3}$ wherein $R^{a1}$ and $R^{a2}$ are the same or different and each is a hydrogen atom, a $C_{1-4}$ alkyl group or a benzyl group, and $R^{a3}$ is a $C_{1-4}$ alkyl group, $R^5$ is a hydrogen atom or a group selected from the above-mentioned group A, $R^4$ and $R^5$ in combination optionally form a fused ring together with a benzene ring bonded thereto, m is 0, 1, 2 or 3, and when m is 2 or 3, each $R^6$ may be the same or different, $R^{31}$ is a hydrogen atom, a cyano group, a hydroxy group, an amino group, a nitro group, a halogen atom, a $C_{1-4}$ alkyl group, a $C_{1-4}$ alkoxy group, a $C_{1-4}$ alkylsulfanyl group, a halo $C_{1-4}$ alkyl group or a halo $C_{1-4}$ alkyloxy group, $R^{32}$ and $R^{33}$ are the same or different and each is (1) a hydrogen atom, (2) a cyano group, (3) a nitro group, (4) a halogen atom, (5) a $C_{3-10}$ carbon ring group optionally substituted by 1 to 5 substituents selected from the above-mentioned group A, (6) a heterocyclic group optionally substituted by 1 to 5 substituents selected from the above-mentioned group A (wherein the heterocyclic group is a saturated or unsaturated ring containing, besides carbon atom, at least one hetero atom selected from nitrogen atom, oxygen atom and sulfur atom), (7) a $C_{1-10}$ alkyl group optionally substituted by 1 to 3 substituents selected from halogen atom and group B: a $C_{3-10}$ carbon ring group optionally substituted by 1 to 5 substituents selected from the above-mentioned group A, a heterocyclic group (as defined above) optionally substituted by 1 to 5 substituents selected from the above-mentioned group A, $OR^{a4}$, —$SR^{a4}$, —$NR^{a4}R^{a5}$, —$CONR^{a4}R^{a5}$, —$SO_2NR^{a4}R^{a5}$, —$COR^{a6}$, —$NR^{a4}COR^{a6}$, —$SO_2R^{a5}$, —$NR^{a4}SO_2R^{a6}$, —$COOR^{a4}$ and —$NR^{a5}COOR^{a6}$ wherein $R^{a4}$ and $R^{a5}$ are the same or different and each is a hydrogen atom, a $C_{1-4}$ alkyl group, a $C_{3-10}$ carbon ring group optionally substituted by 1 to 5 substituents selected from the above-mentioned group A or a heterocyclic group (as defined above) optionally substituted by 1 to 5 substituents selected from the above-mentioned group A, $R^{a6}$ is a $C_{1-4}$ alkyl group, a $C_{3-10}$ carbon ring group optionally substituted by 1 to 5 substituents selected from the above-mentioned group A or a heterocyclic group (as defined above) optionally substituted by 1 to 5 substituents selected from the above-mentioned group A, (8) —$OR^{a7}$, (9) —$SR^{a7}$, (10) —$NR^{a7}R^{a8}$, (11) —$NR^{a7}COR^{a9}$, (12) —$COOR^{a10}$ or (13) —N═CH—$NR^{a10}R^{a11}$ wherein $R^{a7}$ and $R^{a8}$ are the same or different and each is a hydrogen atom, a group selected from the above-mentioned group B, or a $C_{1-10}$ alkyl group optionally substituted by 1 to 3 substituents selected from a halogen atom and the above-mentioned group B, $R^{a9}$ is a $C_{1-4}$ alkyl group, $R^{a10}$ and $R^{a11}$ are the same or different and each is a hydrogen atom or a $C_{1-4}$ alkyl group, or a salt thereof.

[35] The compound of the above-mentioned [34], wherein the compound represented by the formula [I] is selected from the group consisting of 5-(3-chloro-2-fluorobenzyl)-2-fluoro-4-methoxybenzoic acid, 5-(3-chloro-2-fluorobenzyl)-2-fluoro-4-methoxybenzoic acid methyl ester and 5-(3-chloro-2-fluorobenzyl)-2-fluoro-4-methoxybenzoic acid ethyl ester, or a salt thereof.

[36] A method of producing a compound represented by the formula [I]:

[I]

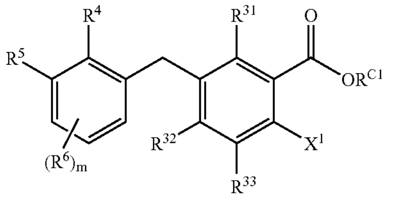

wherein $R^{C1}$ is a hydrogen atom or a carboxyl-protecting group, $X^1$ is a halogen atom, $R^4$ and $R^6$ are the same or different and each is a group selected from group A:

cyano group, phenyl group, nitro group, halogen atom, $C_{1-4}$ alkyl group, halo $C_{1-4}$ alkyl group, halo $C_{1-4}$ alkyloxy group, —$OR^{a1}$, —$SR^{a1}$, —$NR^{a1}R^{a2}$, —$CONR^{a1}R^{a2}$, —$SO_2NR^{a1}R^{a2}$, —$COR^{a3}$, —$NR^{a1}COR^{a3}$, —$SO_2R^{a3}$, —$NR^{a1}SO_2R^{a3}$, —$COOR^{a1}$ and —$NR^{a2}COOR^{a3}$ wherein $R^{a1}$ and $R^{a2}$ are the same or different and each is a hydrogen atom, a $C_{1-4}$ alkyl group or a benzyl group, and $R^{a3}$ is a $C_{1-4}$ alkyl group, $R^5$ is a hydrogen atom or a group selected from the above-mentioned group A, $R^4$ and $R^5$ in combination optionally form a fused ring together with the benzene ring bonded thereto, m is 0, 1, 2 or 3, and when m is 2 or 3, each $R^6$ may be the same or different, $R^{31}$ is a hydrogen atom, a cyano group, a hydroxy group, an amino group, a nitro group, a halogen atom, a $C_{1-4}$ alkyl group, a $C_{1-4}$ alkoxy group, a $C_{1-4}$ alkylsulfanyl group, a halo $C_{1-4}$ alkyl group or a halo $C_{1-4}$ alkyloxy group, $R^{32}$ and $R^{33}$ are the same or different and each is (1) a hydrogen atom, (2) a cyano group, (3) a nitro group, (4) a halogen atom, (5) a $C_{3-10}$ carbon ring group optionally substituted by 1 to 5 substituents selected from the above-mentioned group A, (6) a heterocyclic group optionally substituted by 1 to 5 substituents selected from the above-mentioned group A (wherein the heterocyclic group is a saturated or unsaturated ring containing, besides carbon atom, at least one hetero atom selected from nitrogen atom, oxygen atom and sulfur atom), (7) a $C_{1-10}$ alkyl group optionally substituted by 1 to 3 substituents selected from halogen atom and group B:

a $C_{3-10}$ carbon ring group optionally substituted by 1 to 5 substituents selected from the above-mentioned group A, a heterocyclic group (as defined above) optionally substituted by 1 to 5 substituents selected from the above-mentioned group A, —$OR^{a4}$, —$SR^{a4}$, —$NR^{a4}R^{a5}$, —$CONR^{a4}R^{a5}$, —$SO_2NR^{a4}R^{a5}COR^{a6}$, —$NR^{a4}COR^{a6}$, —$SO_2R^{a6}$, —$NR^{a4}SO_2R^{a6}$, —$COOR^{a4}$ and —$NR^{a5}COOR^{a6}$ wherein $R^{a4}$ and $R^{a5}$ are the same or different and each is a hydrogen atom, a $C_{1-4}$ alkyl group, a $C_{3-10}$ carbon ring group optionally substituted by 1 to 5 substituents selected from the above-mentioned group A or a heterocyclic group (as defined above) optionally substituted by 1 to 5 substituents selected from the above-mentioned group A, $R^{a6}$ is a $C_{1-4}$ alkyl group, a $C_{3-10}$ carbon ring group optionally substituted by 1 to 5 substituents selected from the above-mentioned group A or a heterocyclic group (as defined above) optionally substituted by 1 to 5 substituents selected from the above-mentioned group A, (8) —$OR^{a7}$, (9) —$SR^{a7}$, (10) —$NR^{a7}R^{a8}$ (11) —$NR^{a7}COR^{a9}$, (12) —$COOR^{a10}$ or (13) —N═CH—$NR^{a10}R^{a11}$ wherein $R^{a7}$ and $R^{a8}$ are the same or different and each is a hydrogen atom, a group selected from the above-mentioned group B or a $C_{1-10}$ alkyl group optionally substituted by 1 to 3 substituents selected from a halogen atom and the above-mentioned group B, $R^{a9}$ is a $C_{1-4}$ alkyl group, $R^{a10}$ and $R^{a11}$ are the same or different and each is a hydrogen atom or a $C_{1-4}$ alkyl group, or a salt thereof, from a compound represented by the formula [II]:

[II]

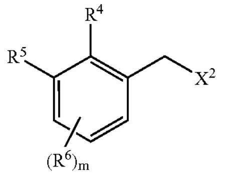

wherein $R^4$ and $R^6$ are the same or different and each is a group selected from group A:

cyano group, phenyl group, nitro group, halogen atom, $C_{1-4}$ alkyl group, halo $C_{1-4}$ alkyl group, halo $C_{1-4}$ alkyloxy group, —$OR^{a1}$, —$SR^{a1}$, —$NR^{a1}R^{a2}$, —$CONR^{a1}R^{a2}$, —$SO_2NR^{a1}R^{a2}$, —$COR^{a3}$, —$NR^{a1}COR^{a3}$, —$SO_2R^{a3}$, —$NR^{a1}SO_2R^{a3}$, —$COOR^{a1}$ and —$NR^{a2}COOR^{a3}$ wherein $R^{a1}$ and $R^{a2}$ are the same or different and each is a hydrogen atom, a $C_{1-4}$ alkyl group or a benzyl group, and $R^{a3}$ is a $C_{1-4}$ alkyl group, $R^5$ is a hydrogen atom or a group selected from the above-mentioned group A, $R^4$ and $R^5$ in combination optionally form a fused ring together with the benzene ring bonded thereto, m is 0, 1, 2 or 3, and when m is 2 or 3, each $R^6$ may be the same or different, and $X^2$ is a halogen atom.

[37] The production method of the above-mentioned [36], which comprises reacting a compound represented by the formula [II]:

[II]

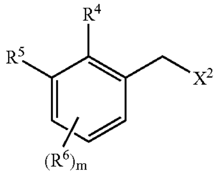

wherein each symbol is as defined in the above-mentioned [36], with a compound represented by the formula [IV]:

[IV]

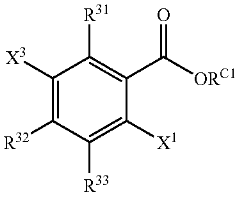

wherein $X^3$ is a halogen atom, and the other symbols are as defined in the above-mentioned [36], in the presence of a metal atom $M^1$.

[38] A method of producing a compound represented by the formula [III]:

[III]

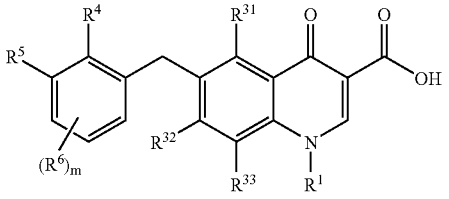

wherein $R^1$ is a group selected from the above-mentioned group B, or a $C_{1-10}$ alkyl group optionally substituted by 1 to 3 substituents selected from halogen atom and the above-mentioned group B, and the other symbols are as defined above, or a salt thereof, from a compound represented by the formula [I]:

[I]

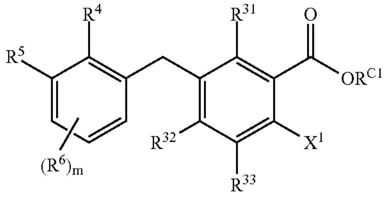

wherein $R^{C1}$ is a hydrogen atom or a carboxyl-protecting group, $X^1$ is a halogen atom, $R^4$ and $R^6$ are the same or different and each is a group selected from group A:

cyano group, phenyl group, nitro group, halogen atom, $C_{1-4}$ alkyl group, halo $C_{1-4}$ alkyl group, halo $C_{1-4}$ alkyloxy group, —$OR^{a1}$, —$SR^{a1}$, —$NR^{a1}R^{a2}$, —$CONR^{a1}R^{a2}$, —$SO_2NR^{a1}R^{a2}$, —$COR^{a3}$, —$NR^{a1}COR^{a3}$, —$SO_2R^{a3}$, —$NR^{a1}SO_2R^{a3}$, —$COOR^{a1}$ and —$NR^{a2}COOR^{a3}$ wherein $R^{a1}$ and $R^{a2}$ are the same or different and each is a hydrogen atom, a $C_{1-4}$ alkyl group or a benzyl group, and $R^{a3}$ is a $C_{1-4}$ alkyl group, $R^5$ is a hydrogen atom or a group selected from the above-mentioned group A, $R^4$ and $R^5$ in combination optionally form a fused ring together with the benzene ring bonded thereto, m is 0, 1, 2 or 3, and when m is 2 or 3, each $R^6$ may be the same or different, $R^{31}$ is a hydrogen atom, a cyano group, a hydroxy group, an amino group, a nitro group, a halogen atom, a $C_{1-4}$ alkyl group, a $C_{1-4}$ alkoxy group, a $C_{1-4}$ alkylsulfanyl group, a halo $C_{1-4}$ alkyl group or a halo $C_{1-4}$ alkyloxy group, $R^{32}$ and $R^{33}$ are the same or different and each is (1) a hydrogen atom, (2) a cyano group, (3) a nitro group, (4) a halogen atom, (5) a $C_{3-10}$ carbon ring group optionally substituted by 1 to 5 substituents selected from the above-mentioned group A, (6) a heterocyclic group optionally substituted by 1 to 5 substituents selected from the above-mentioned group A (wherein the heterocyclic group is a saturated or unsaturated ring containing, besides carbon atom, at least one hetero atom selected from nitrogen atom, oxygen atom and sulfur atom, (7) a $C_{1-10}$ alkyl group optionally substituted by 1 to 3 substituents selected from halogen atom and group B:

a $C_{3-10}$ carbon ring group optionally substituted by 1 to 5 substituents selected from the above-mentioned group A, a heterocyclic group (as defined above) optionally substituted by 1 to 5 substituents selected from the above-mentioned group A, —$OR^{a4}$, —$SR^{a4}$, —$NR^{a4}R^{a5}$, —$CONR^{a4}R^{a5}$, —$SO_2NR^{a4}R^{a5}$, —$COR^{a6}$, —$NR^{a4}COR^{a6}$, —$SO_2R^{a6}$, —$NR^{a4}SO_2R^{a6}$, —$COOR^{a4}$ and —$NR^{a5}COOR^{a6}$ wherein $R^{a4}$ and $R^{a5}$ are the same or different and each is a hydrogen atom, a $C_{1-4}$ alkyl group, a $C_{3-10}$ carbon ring group optionally substituted by 1 to 5 substituents selected from the above-mentioned group A or a heterocyclic group (as defined above) optionally substituted by 1 to 5 substituents selected from the above-mentioned group A, $R^{a6}$ is a $C_{1-4}$ alkyl group, a $C_{3-10}$ carbon ring group optionally substituted by 1 to 5 substituents selected from the above-mentioned group A or a heterocyclic group (as defined above) optionally substituted by 1 to 5 substituents selected from the above-mentioned group A, (8) —$OR^{a7}$, (9) —$SR^{a7}$, (10) —$NR^{a7}R^{a8}$ (11) —$NR^{a7}COR^{a9}$, (12) —$COOR^{a10}$ or (13) —N═CH—$NR^{a10}R^{a11}$ wherein $R^{a7}$ and $R^{a8}$ are the same or different and each is a hydrogen atom, a group selected from the above-mentioned group B, or a $C_{1-10}$ alkyl group optionally substituted by 1 to 3 substituents selected from a halogen atom and the above-mentioned group B, $R^{a9}$ is a $C_{1-4}$ alkyl group, $R^{a10}$ and $R^{a11}$ are the same or different and each is a hydrogen atom or a $C_{1-4}$ alkyl group.

[39] The production method of the above-mentioned [38], which comprises a step of preparing a compound represented by the formula [I]:

[I]

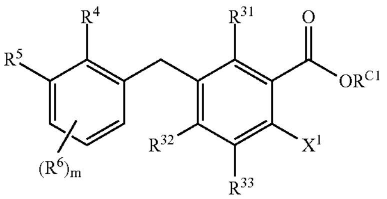

wherein each symbol is as defined in the above-mentioned [38], or a salt thereof, by reacting a compound represented by the formula [II]:

[II]

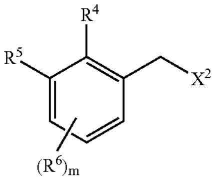

wherein $X^2$ is a halogen atom, and the other symbols are as defined in the above-mentioned [38], with a compound represented by the formula [IV]:

[IV]

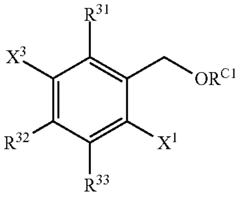

wherein $X^3$ is a halogen atom, and the other symbols are as defined in the above-mentioned [38], in the presence of a metal atom $M^1$.

[40] The production method of the above-mentioned [39], which further comprises at least one of the following steps:

a step of subjecting a compound represented by the formula [I']

[I']

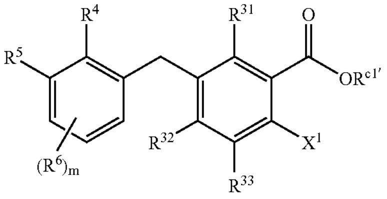

wherein $R^{C1'}$ is a carboxyl-protecting group, and the other symbols are as defined in the above-mentioned [38], or a salt thereof, to hydrolysis to prepare a compound represented by the formula [Ia]:

[Ia]

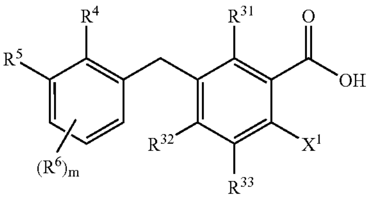

wherein each symbol is as defined in the above-mentioned [38], or a salt thereof;

a step of reacting a compound represented by the above-mentioned formula [Ia], or a salt thereof, with a halogenating agent to prepare a compound represented by the formula [Ib]:

[Ib]

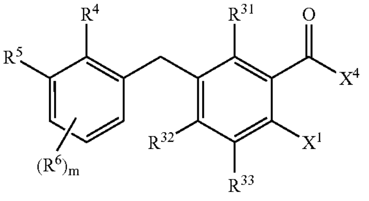

wherein $X^4$ is a halogen atom, and the other symbols are as defined in the above-mentioned [38];

a step of reacting a compound represented by the above-mentioned formula [Ib], or a salt thereof, with a compound represented by the formula [XIIa]:

[XIIa]

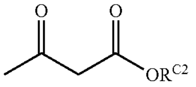

wherein $R^{C2}$ is a carboxyl-protecting group, in the presence of a base, to prepare a compound represented by the formula [XI]:

[XI]

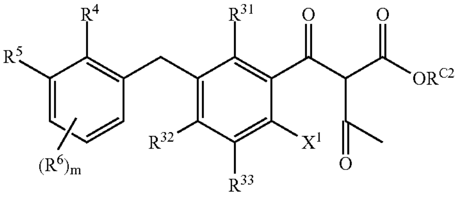

wherein each symbol is as defined in the above-mentioned [38], or a salt thereof;

a step of subjecting a compound represented by the above-mentioned formula [XI], or a salt thereof, to deacetylation to prepare a compound represented by the formula [V]:

[V]

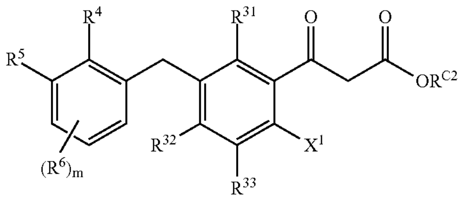

wherein each symbol is as defined in the above-mentioned [38], or a salt thereof;

a step of reacting a compound represented by the above-mentioned formula [Ib], or a salt thereof, with a compound represented by the formula [XIIb]:

[XIIb]

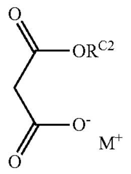

wherein $R^{C2}$ is a carboxyl-protecting group and M is a metal atom M, in the presence of a base and a chelator, and treating the resulting compound with an acid to prepare a compound represented by the formula [V]:

[V]

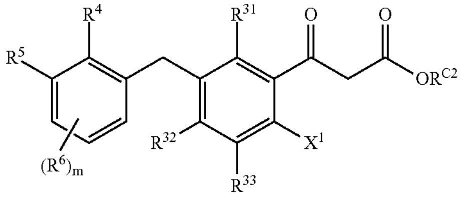

wherein each symbol is as defined in the above-mentioned [38], or a salt thereof;

a step of reacting a compound represented by the above-mentioned formula [V], or a salt thereof, with a compound represented by the formula [XVII]:

[XVII]

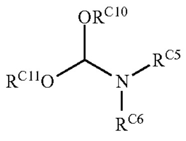

wherein $R^{C5}$ and $R^{C6}$ are the same or different and each is a $C_{1-4}$ is alkyl group, or may form a 5- or 6-membered heterocycle together with the adjacent nitrogen atom, and $R^{C10}$ and $R^{C11}$ are the same or different and each is a $C_{1-4}$ alkyl group, to prepare a compound represented by the formula [VI]:

[VI]

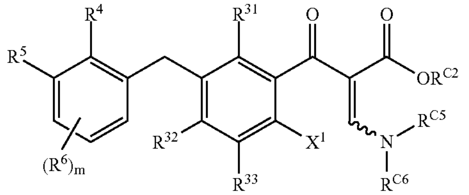

wherein each symbol is as defined in the above-mentioned [38], or a salt thereof;

a step of reacting a compound represented by the above-mentioned formula [VI], or a salt thereof, with a compound represented by the formula [XVI]:

$R^1$—$NH_2$ [XVI]

wherein $R^1$ is as defined in the above-mentioned [38], to prepare a compound represented by the formula [VII]:

[VII]

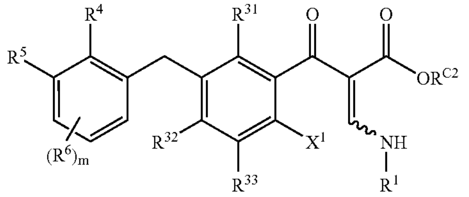

wherein each symbol is as defined in the above-mentioned [38], or a salt thereof;

a step of subjecting a compound represented by the above-mentioned formula [VII] to a cyclization reaction to prepare a compound represented by the formula [VIII]:

[VIII]

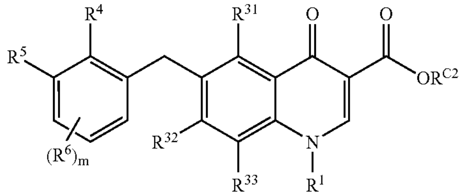

wherein each symbol is as defined in the above-mentioned [38], or a salt thereof; and a step of subjecting a compound represented by the above-mentioned formula [VIII], or a salt thereof, to hydrolysis to prepare a compound represented by the formula [III]:

[III]

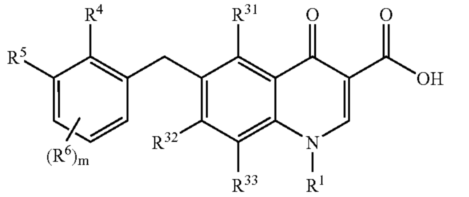

wherein each symbol is as defined in the above-mentioned [38], or a salt thereof.

[41] The production method of the above-mentioned [40], which comprises a step of subjecting a compound represented by the above-mentioned formula [I'], or a salt thereof, to hydrolysis to prepare a compound represented by the above-mentioned formula [Ia], or a salt thereof;

a step of reacting a compound represented by the above-mentioned formula [Ia], or a salt thereof, with a halogenating agent to prepare a compound represented by the above-mentioned formula [Ib], or a salt thereof;

a step of reacting a compound represented by the above-mentioned formula [Ib], or a salt thereof, with a compound represented by the above-mentioned formula [XIIb] in the presence of a base and a chelator, and treating the resulting compound with an acid to prepare a compound represented by the above-mentioned formula [V], or a salt thereof;

a step of reacting a compound represented by the above-mentioned formula [V], or a salt thereof, with a compound represented by the above-mentioned formula [XVII] to prepare a compound represented by the above-mentioned formula [VI], or a salt thereof;

a step of reacting a compound represented by the above-mentioned formula [VI], or a salt thereof, with a compound represented by the above-mentioned formula [XVI] to prepare a compound represented by the above-mentioned formula [VII];

a step of subjecting a compound represented by the above-mentioned formula [VII] to a cyclization reaction to prepare a compound represented by the above-mentioned formula [VIII], or a salt thereof; and a step of subjecting a compound represented by the above-mentioned formula [VIII], or a salt thereof, to hydrolysis to prepare a compound represented by the above-mentioned formula [III], or a salt thereof.

[42] The production method of the above-mentioned [39], which further comprises at least one of the following steps:

a step of subjecting a compound represented by the formula [I']:

[I']

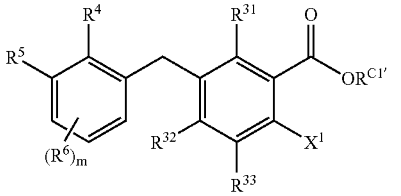

wherein $R^{C1'}$ is a carboxyl-protecting group, and the other symbols are as defined in the above-mentioned [38], or a salt thereof, to hydrolysis to prepare a compound represented by the formula [Ia]:

[Ia]

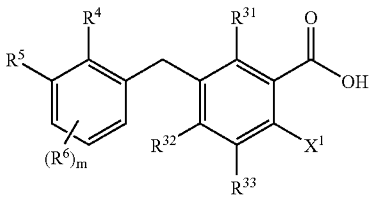

wherein each symbol is as defined in the above-mentioned [38], or a salt thereof;

a step of reacting a compound represented by the above-mentioned formula [Ia], or a salt thereof, with a halogenating agent to prepare a compound represented by the formula [Ib]:

[Ib]

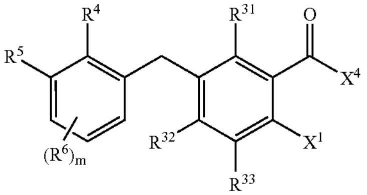

wherein $X^4$ is a halogen atom, and the other symbols are as defined in the above-mentioned [38], or a salt thereof;

a step of reacting a compound represented by the above-mentioned formula [Ib], or a salt thereof, with a compound represented by the formula [XIV]:

[XIV]

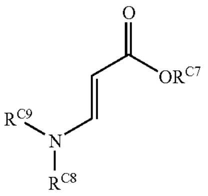

wherein $R^{C7}$ is a $C_{1-4}$ alkyl group, $R^{C8}$ and $R^{C9}$ are the same or different and each is a $C_{1-4}$ alkyl group, or may form a 5- or 6-membered heterocycle together with the adjacent nitrogen atom, in the presence of a base to prepare a compound represented by the formula [XIII]:

[XIII]

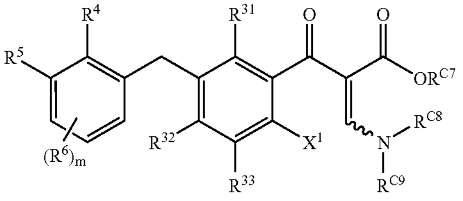

wherein each symbol is as defined in the above-mentioned [38];

a step of reacting a compound represented by the above-mentioned formula [XIII] with a compound represented by the formula [XVI]:

$R^1—NH_2$ [XVI]

wherein $R^1$ is as defined in the above-mentioned [38], to prepare a compound represented by the formula [IX]:

[IX]

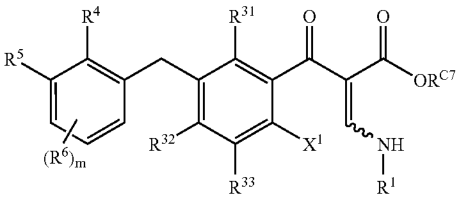

wherein each symbol is as defined in the above-mentioned [38];

a step of subjecting a compound represented by the above-mentioned formula [IX] to a cyclization reaction to prepare a compound represented by the formula [XV]:

[XV]

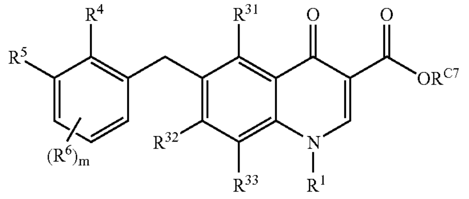

wherein each symbol is as defined in the above-mentioned [38], or a salt thereof; and a step of subjecting a compound represented by the above-mentioned formula [XV], or a salt thereof, to hydrolysis to prepare a compound represented by the formula [III]:

[III]

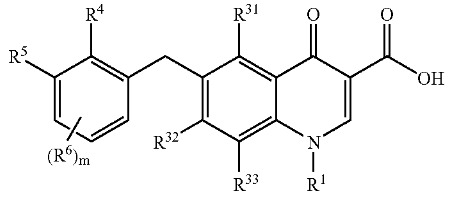

wherein each symbol is as defined in the above-mentioned [38], or a salt thereof.

[43] The production method of the above-mentioned [42], which comprises a step of subjecting a compound represented by the above-mentioned formula [I'], or a salt thereof, to hydrolysis to prepare a compound represented by the above-mentioned formula [Ia] or a salt thereof;

a step of reacting a compound represented by the above-mentioned formula [Ia], or a salt thereof, with a halogenating agent to prepare a compound represented by the above-mentioned formula [Ib] or a salt thereof;

a step of reacting a compound represented by the above-mentioned formula [Ib], or a salt thereof, with a compound represented by the above-mentioned formula [XIV] in the presence of a base to prepare a compound represented by the above-mentioned formula [XIII];

a step of reacting a compound represented by the above-mentioned formula [XIII] with a compound represented by the above-mentioned formula [XVI] to prepare a compound represented by the above-mentioned formula [IX];

a step of subjecting a compound represented by the above-mentioned formula [IX] to a cyclization reaction to prepare a compound represented by the above-mentioned formula [XV] or a salt thereof; and a step of subjecting a compound represented by the above-mentioned formula [XV], or a salt thereof, to hydrolysis to prepare a compound represented by the above-mentioned formula [III] or a salt thereof.

[44] The production method of the above-mentioned [36] or [38], wherein the compound represented by the formula [I] is 5-(3-chloro-2-fluorobenzyl)-2-fluoro-4-methoxybenzoic acid.

[45] The production method of the above-mentioned [36] or [39], wherein the compound represented by the formula [II] is 3-chloro-2-fluorobenzylchloride.

Effect of the Invention

The present invention can provide a novel compound useful as a synthetic intermediate for an anti-HIV agent (compound) having an integrase inhibitory activity, a production method of the synthetic intermediate, and a production method of an anti-HIV agent (compound) (e.g., compound (10) and the like) using the synthetic intermediate.

The present invention can provide an industrially highly valuable production method of an anti-HIV agent (compound). For example, using intermediate compound (2') [compound (2-2): compounds (2-2-A) and (2-2-B) and/or compound (2-3): compounds (2-3-A) and (2-3-B)] having a methoxy group as a synthetic intermediate for the production of compound (10), which is an anti-HIV agent (compound), a decrease in the yield due to the final step (alkoxylation, particularly methoxylation) in the prior art and by-production of sodium fluoride can be avoided. Using compound (2') in a ring-closing step, moreover, the generation of hydrogen fluoride (HF) that causes corrosion of the production facility can be avoided, whereby problems in the prior art (avoidance of decreased yield, corrosion of production facility, etc.) can be overcome.

Further, the present invention can also provide a production method of the above-mentioned synthetic intermediate.

Since the above-mentioned synthetic intermediate can overcome the above-mentioned problems in the prior art during the production of an anti-HIV agent (compound), the production method of the synthetic intermediate also has a high value for industrial application and is significant.

Of the synthetic intermediates, compound (2') is stable by itself, and can tolerate severe conditions and/or long-term preservation. Furthermore, when the quality of compound (2') can be controlled in the initial production stage, not only the quality management in the later steps but also the quality management of an anti-HIV agent (compound) (e.g., compound (10) and the like) can be facilitated. Therefore, compound (2') is an extremely important intermediate compound.

Moreover, the present invention uses highly circulative compound (1) as a starting material. Thus, the production method of the present invention can produce an anti-HIV agent (compound) more economically, since stability of supply of the starting material can be improved.

BEST MODE FOR CARRYING OUT THE INVENTION

Detailed Description of the Invention

The terms and symbols to be used in the present invention are defined in the following.

A "halogen atom" means a fluorine atom, a chlorine atom, a bromine atom or an iodine atom.

A "$C_1$-$C_4$ alkyl group" means a straight chain or branched chain alkyl group having 1 to 4 carbon atoms, and specific examples include methyl group, ethyl group, propyl group, isopropyl group, butyl group, isobutyl group, sec-butyl group and tert-butyl group.

A "hydroxyl-protecting group" means a general hydroxyl-protecting group known to those of ordinary skill in the art, which is introduced to prevent reaction of the hydroxyl group. Examples thereof include the protecting groups described in Protective Groups in Organic Synthesis, published by John Wiley and Sons (1980) and the like, and specific examples thereof include ether protecting groups such as tetrahydropyranyl group, methoxymethyl group and the like; carbonate protecting groups such as methylcarbonate group, ethylcarbonate group and the like; silicon protecting groups such as trimethylsilyl group, tert-butyldimethylsilyl group, tert-butyldiphenylsilyl group, etc. and the like.

R is a fluorine atom or a methoxy group.

$R^{100}$ is a "$C_1$-$C_4$ alkyl group", preferably a methyl group or an ethyl group, and particularly preferably an ethyl group.

$R^{200}$ is "hydroxyl-protecting group", preferably a silicon protecting group, more preferably a tert-butyldimethylsilyl group.

$R^{300}$ is a "$C_1$-$C_4$ alkyl group", preferably a methyl group or an ethyl group, particularly preferably a methyl group.

$R^{400}$ is a hydrogen atom or a "$C_1$-$C_4$ alkyl group", preferably a methyl group or an ethyl group, particularly preferably a methyl group.

$X^{100}$ is a "halogen atom", preferably a chlorine atom or a bromine atom.

$X^{200}$ is a "halogen atom", preferably a bromine atom or an iodine atom, more preferably a bromine atom.

A "metal atom M" is an alkali metal atom, and also includes a monovalent ion. Preferred is a sodium atom or a potassium atom, more preferably a potassium atom.

The "metal atom $M^1$" is a zinc atom, preferably metal zinc.

The expressions of "produced from a compound represented by the formula [I]" and "produced from a compound represented by the formula [II]" not only mean directly producing an object compound from compound [I] or compound [II], but also mean that some steps may be included in the production.

The "carboxyl-protecting group" is a substituent introduced to avoid a reaction of carboxyl group, and examples thereof include a benzyl group, a methyl group, an ethyl group, an n-propyl group, an isopropyl group, a tert-butyl group, a phenacyl group, a 2,2,2-trichloroethyl group, a p-nitrobenzyl group, a diphenylmethyl group, a 4-picolyl group, a cyclohexyl group and the like.

The "carboxyl-protecting group" for $R^{C1}$ is preferably a methyl group, an ethyl group, an n-propyl group, an isopropyl group or a tert-butyl group, more preferably an ethyl group.

The "carboxyl-protecting group" for $R^{C2}$ is preferably a methyl group, an ethyl group, an n-propyl group, an isopropyl group or a tert-butyl group, more preferably an ethyl group.

The "halogen atom" is a fluorine atom, a chlorine atom, a bromine atom or an iodine atom and, unless otherwise specified, it is preferably a fluorine atom, a chlorine atom or a bromine atom.

The "halogen atom" for $R^{32}$, $R^{33}$ or $R^6$ (including $R^{6'}$, $R^{6''}$ or $R^{6'''}$ defined below) or group A (as defined below) is particularly preferably a fluorine atom or a chlorine atom, and the "halogen atom" for $R^{32}$ is more preferably a chlorine atom.

The "halogen atom" for $R^{31}$, $R^{33}$, $R^{6'}$ or $R^{6'''}$ and the "halogen atom" of the "$C_{1-10}$ alkyl group optionally substituted by 1 to 3 substituents selected from halogen atom and group B (as defined below)" for $R^{32}$ or $R^{33}$ is more preferably a fluorine atom.

The "halogen atom" for $R^4$ is preferably a fluorine atom or a chlorine atom, more preferably a fluorine atom.

The "halogen atom" for $R^5$ is preferably a fluorine atom or a chlorine atom, more preferably a chlorine atom.

The "halogen atom" for $X^1$ is preferably a fluorine atom.

The "halogen atom" for $X^2$ is preferably a chlorine atom or a bromine atom, more preferably a chlorine atom.

The "halogen atom" for $X^3$ is preferably a bromine atom.

The "halogen atom" for $X^4$ is preferably a chlorine atom.

The "$C_{1-4}$ alkyl group" represents a straight chain or branched chain alkyl group having 1 to 4 carbon atoms. Specific examples include a methyl group, an ethyl group, a propyl group, an isopropyl group, a butyl group, an isobutyl group, a sec-butyl group and a tert-butyl group.

The "$C_{1-4}$ alkyl group" for $R^{31}$ or $R^{a6}$ is preferably a methyl group or an ethyl group.

The "$C_{1-4}$ alkyl group" for $R^4$, $R^5$ or $R^6$ (including $R^{6'}$, $R^{6''}$ or $R^{6'''}$ defined below) or group A (as defined below) is preferably a methyl group, an ethyl group or an isopropyl group, more preferably a methyl group.

The "$C_{1-4}$ alkyl group" for $R^{a1}$ or $R^{a2}$ is preferably a methyl group, an ethyl group, a propyl group or an isopropyl group, more preferably a methyl group.

The "$C_{1-4}$ alkyl group" for $R^{a3}$, $R^{a9}$, $R^{a10}$ or $R^{a11}$ is preferably a methyl group.

The "$C_{1-4}$ alkyl group" for $R^{a4}$ or $R^{a5}$ is preferably a methyl group, an ethyl group or a tert-butyl group.

The "$C_{1-4}$ alkyl group" for $R^{a6}$ is preferably a methyl group, an ethyl group or a tert-butyl group.

The "$C_{1-4}$ alkyl group" for $R^{C5}$ or $R^{C6}$ is preferably a methyl group, an ethyl group, a propyl group or an isopropyl group, more preferably a methyl group. $R^{C5}$ and $R^{C6}$ are preferably the same alkyl groups.

The "$C_{1-4}$ alkyl group" for $R^{C7}$ is preferably a methyl group, an ethyl group, a propyl group or an isopropyl group, more preferably an ethyl group.

The "$C_{1-4}$ alkyl group" for $R^{C8}$ or $R^{C9}$ is preferably a methyl group, an ethyl group, a propyl group or an isopropyl group, more preferably a methyl group. $R^{C8}$ and $R^{C9}$ are preferably the same alkyl groups.

The "$C_{1-4}$ alkyl group" for $R^{C10}$ or $R^{C11}$ is preferably a methyl group, an ethyl group, a propyl group or an isopropyl group, more preferably a methyl group. $R^{C10}$ and $R^{C11}$ are preferably the same alkyl groups.

The "halo $C_{1-4}$ alkyl group" is the above-defined "$C_{1-4}$ alkyl group", which is substituted by 1 to 9, preferably 1 to 3, "halogen atom(s)" defined above.

Examples of thereof include a 2-fluoroethyl group, a 2-chloroethyl group, a 2-bromoethyl group, a 3-fluoropropyl group, a 3-chloropropyl group, a 4-fluorobutyl group, a 4-chlorobutyl group, a trifluoromethyl group, a 2,2,2-trifluoroethyl group, a 3,3,3-trifluoropropyl group, a 4,4,4-trifluorobutyl group, a pentafluoroethyl group, a 2,2,2-trifluoro-1-trifluoromethylethyl group and the like.

The "halo $C_{1-4}$ alkyl group" for $R^{31}$, $R^4$, $R^5$ or $R^6$ (including $R^{6'}$, $R^{6''}$ or $R^{6'''}$ defined below) or group A (as defined below) is preferably a trifluoromethyl group.

The "$C_{1-4}$ alkoxy group" is an alkyloxy group wherein the alkyl moiety is the above-defined "$C_{1-4}$ alkyl group", specifically a methoxy group, an ethoxy group, a propoxy group, an isopropoxy group, a butoxy group, an isobutoxy group or a tert-butoxy group.

The "$C_{1-4}$ alkoxyl group" for $R^{31}$ is preferably a methoxy group.

The "$C_{1-4}$ alkylsulfanyl group" is an alkylsulfanyl group wherein the alkyl moiety is the above-defined "$C_{1-4}$ alkyl group", specifically a methylsulfanyl group, an ethylsulfanyl group, a propylsulfanyl group, an isopropylsulfanyl group, a butylsulfanyl group, an isobutylsulfanyl group or a tert-butylsulfanyl group.

The "$C_{1-4}$ alkylsulfanyl group" for $R^{31}$ is preferably a methylsulfanyl group.

The "halo $C_{1-4}$ alkyloxy group" is a haloalkyloxy group wherein the haloalkyl moiety is the above-defined "halo $C_{1-4}$ alkyl group".

Specific examples include a 2-fluoroethyloxy group, a 2-chloroethyloxy group, a 2-bromoethyloxy group, a 3-fluoropropyloxy group, a 3-chloropropyloxy group, a 4-fluorobutyloxy group, a 4-chlorobutyloxy group, a trifluoromethyloxy group, a 2,2,2-trifluoroethyloxy group, a 3,3,3-trifluoropropyloxy group, a 4,4,4-trifluorobutyloxy group, a pentafluoroethyloxy group, a 2,2,2-trifluoro-1-trifluoromethylethyloxy group and the like.

The "halo $C_{1-4}$ alkyloxy group" for $R^{31}$, $R^4$, $R^5$, $R^6$, $R^{6'}$, $R^{6''}$ $R^{6'''}$ or group A (as defined below) is preferably a trifluoromethyloxy group.

The "$C_{3-10}$ carbon ring group" is a saturated or unsaturated cyclic hydrocarbon group having 3 to 10 carbon atoms, and means an aryl group, a cycloalkyl group, a cycloalkenyl group or a fused ring thereof.

Examples of the "aryl group" include a $C_{6-10}$ aryl group, specifically a phenyl group, a naphthyl group, a pentalenyl group, an azulenyl group and the like, preferably a phenyl group and a naphthyl group, and particularly preferably a phenyl group.

Examples of the "cycloalkyl group" include a $C_{3-10}$ cycloalkyl group, specifically a cyclopropyl group, a cyclobutyl group, a cyclopentyl group, a cyclohexyl group, a cycloheptyl group, a cyclooctyl group, an adamantyl group, a norbornanyl group and the like, preferably a cyclopropyl group, a cyclobutyl group, a cyclopentyl group and a cyclohexyl group.

Examples of the "cycloalkenyl group" include a $C_{3-10}$ cycloalkenyl group comprising at least one, preferably 1 or 2, double bonds, specifically a cyclopropenyl group, a cyclobutenyl group, a cyclopentenyl group, a cyclopentadienyl group, a cyclohexenyl group, a cyclohexadienyl group (e.g., a 2,4-cyclohexadien-1-yl group, a 2,5-cyclohexadien-1-yl group etc.), a cycloheptenyl group and a cyclooctenyl group and the like.

Examples of the ring that these "aryl group", "cycloalkyl group" and "cycloalkenyl group" are condensed to form include an indenyl group, an indanyl group, a 1,4-dihydronaphthyl group, a 1,2,3,4-tetrahydronaphthyl group (e.g., 1,2,3,4-tetrahydro-2-naphthyl group, 5,6,7,8-tetrahydro-2-naphthyl group etc.), a perhydronaphthyl group and the like. Preferred is a fused ring of a phenyl group and other ring, an indenyl group, an indanyl group, an 1,4-dihydronaphthyl group, an 1,2,3,4-tetrahydronaphthyl group and the like, particularly preferred is an indanyl group.

The "$C_{3-10}$ carbon ring group optionally substituted by 1 to 5 substituents selected from group A" is the above-defined "$C_{3-10}$ carbon ring group" optionally substituted by 1 to 5, preferably 1 to 3, substituents selected from group A defined below, and includes an unsubstituted "$C_{3-10}$ carbon ring group". In addition, the position of substitution is not particularly limited as long as it is a substitutable position.

In the specification, the "group A" is a group consisting of a cyano group, a phenyl group, a nitro group, the above-defined "halogen atom", the above-defined "$C_{1-4}$ alkyl group", the above-defined "halo $C_{1-4}$ alkyl group", the above-defined "halo $C_{1-4}$ alkyloxy group", $—OR^{a1}$, $—SR^{a1}$, $—NR^{a1}R^{a2}$, $—CONR^{a1}R^{a2}$, $—SO_2NR^{a1}R^{a2}$, $—COR^{a3}$, $—NR^{a1}COR^{a3}$, $—SO_2R^{a3}$, $—NR^{a1}SO_2R^{a3}$, $—COOR^{a1}$ and $—NR^{a2}COOR^{a3}$ wherein $R^{a1}$ and $R^{a2}$ are the same or different and each is a hydrogen atom, the above-defined "$C_{1-4}$ alkyl group" or a benzyl group, and $R^{a3}$ is the above-defined "$C_{1-4}$ alkyl group".

Examples of "$—OR^{a1}$" include a hydroxy group, a methoxy group, an ethoxy group, a propoxy group, an isopropoxy group, a tert-butoxy group and the like.

Examples of the "$—SR^{a1}$" include a mercapto group, a methylsulfanyl group, an ethylsulfanyl group, a propylsulfanyl group, an isopropylsulfanyl group, a tert-butylsulfanyl group and the like.

Examples of "$—NR^{a1}R^{a2}$" include an amino group, a methylamino group, an ethylamino group, a propylamino group, an isopropylamino group, a tert-butylamino group, a dimethylamino group, a diethylamino group, an N-ethyl-N-methylamino group, an N-methyl-N-propylamino group, an N-isopropyl-N-methylamino group, an N-benzyl-N-methylamino group and the like.

Examples of "$—CONR^{a1}R^{a2}$" include a carbamoyl group, a methylaminocarbonyl group, an ethylaminocarbonyl group, a propylaminocarbonyl group, an isopropylaminocarbonyl group, a tert-butylaminocarbonyl group, a dimethylaminocarbonyl group, a diethylaminocarbonyl group, an N-methyl-N-ethylaminocarbonyl group and the like.

Examples of "$—SO_2NR^{a1}R^{a2}$" include a sulfamoyl group, a methylaminosulfonyl group, an ethylaminosulfonyl group, a propylaminosulfonyl group, an isopropylaminosulfonyl group, a tert-butylaminosulfonyl group, a dimethylaminosulfonyl group, a diethylaminosulfonyl group, an N-methyl-N-ethylaminosulfonyl group and the like.

Examples of "$—COR^{a3}$" include an acetyl group, a propionyl group, a butyryl group, an isobutyryl group, a pivaloyl group and the like.

Examples of "$—NR^{a1}COR^{a3}$" include an acetylamino group, a propionylamino group, a butyrylamino group, an isobutyrylamino group, a pivaloylamino group, an N-acetyl-N-methylamino group and the like.

Examples of "$—SO_2R^{a3}$" include a methylsulfonyl group, an ethylsulfonyl group, a propylsulfonyl group, an isopropylsulfonyl group, a tert-butylsulfonyl group and the like.

Examples of "$—NR^{a1}SO_2R^{a3}$" include a methylsulfonylamino group, an ethylsulfonylamino group, a propylsulfonylamino group, an isopropylsulfonylamino group, a tert-butylsulfonylamino group, an N-methyl-N-(methylsulfonyl)amino group and the like.

Examples of "$—COOR^{a1}$" include a carboxyl group, a methoxycarbonyl group, an ethoxycarbonyl group, a propoxycarbonyl group, an isopropoxycarbonyl group, a tert-butoxycarbonyl group and the like.

Examples of "$—NR^{a2}COOR^{a3}$" include a methoxycarbonylamino group, an ethoxycarbonylamino group, a propoxycarbonylamino group, an isopropoxycarbonylamino group, a tert-butoxycarbonylamino group and the like.

Group A preferably contains a cyano group, a phenyl group, a nitro group, a fluorine atom, a chlorine atom, a bromine atom, a methyl group, an ethyl group, an isopropyl group, a trifluoromethyl group, a trifluoromethyloxy group, a hydroxy group, a methoxy group, an ethoxy group, a propoxy group, a methylsulfanyl group, an amino group, a methylamino group, an ethylamino group, an isopropylamino group, a dimethylamino group, a diethylamino group, an N-ethyl-N-methylamino group, an N-methyl-N-propylamino group, an N-isopropyl-N-methylamino group, an N-benzyl-N-methylamino group, a carbamoyl group, a methylaminocarbonyl group, a dimethylaminocarbonyl group, a sulfamoyl group, methylaminosulfonyl group, a dimethylaminosulfonyl group, an acetyl group, an acetylamino group, an N-acetyl-N-methylamino group, a methylsulfonyl group, a methylsulfonylamino group, an N-methyl-N-(methylsulfonyl)amino group, a carboxyl group, a methoxycarbonyl group, a carboxyamino group and a methoxycarbonylamino group.

Group A particularly preferably contains a cyano group, a phenyl group, a nitro group, a fluorine atom, a chlorine atom, a bromine atom, a methyl group, a trifluoromethyl group, a trifluoromethyloxy group, a hydroxy group, a methoxy group, an ethoxy group, a methylsulfanyl group, an amino group, a methylamino group, a dimethylamino group, a diethylamino group, an N-ethyl-N-methylamino group, an N-methyl-N-propylamino group, an N-isopropyl-N-methylamino group, an N-benzyl-N-methylamino group, a dimethylaminocarbonyl group, a methylaminosulfonyl group, a dimethylaminosulfonyl group, an acetylamino group, an N-acetyl-N-methylamino group, a methylsulfonyl group, an N-methyl-N-(methylsulfonyl)amino group and a carboxyl group, more preferably contains a fluorine atom and a chlorine atom.

The number of the substituents that the above-mentioned "$C_{3-10}$ carbon ring group" may have is preferably 1 to 3, and when the "$C_{3-10}$ carbon ring group" is a phenyl group, preferred are 2-position monosubstitution, 3-position monosubstitution, 2,3-position disubstitution, 2,4-position disubstitution, 2,5-position disubstitution, 2,6-position disubstitution, 2,3,4-position trisubstitution, 2,3,5-position trisubstitution and 2,3,6-position trisubstitution, particularly preferred is 2,3-position disubstitution.

Specific examples of the "$C_{3-10}$ carbon ring group optionally substituted by 1 to 5 substituents selected from group A" include a phenyl group, a naphthyl group, a 2-fluorophenyl group, a 2-chlorophenyl group, a 2-bromophenyl group, a 3-fluorophenyl group, a 3-chlorophenyl group, a 3-bromophenyl group, a 4-fluorophenyl group, a 2-nitrophenyl group, a 3-nitrophenyl group, a 2-cyanophenyl group, a 3-cyanophenyl group, a 2-methylphenyl group, a 3-methylphenyl group, a 4-methylphenyl group, a 2-ethylphenyl group, a 3-ethylphenyl group, a 2-isopropylphenyl group, a 3-isopropylphenyl group, a 2-trifluoromethylphenyl group, a 3-trifluoromethylphenyl group, a 2-hydroxyphenyl group, a 3-hydroxyphenyl group, a 4-hydroxyphenyl group, a 2-methoxyphenyl group, a 3-methoxyphenyl group, a 2-ethoxyphenyl group, a 3-ethoxyphenyl group, a 2-propoxyphenyl group, a 3-propoxyphenyl group, a 2-(trifluoromethyl)phenyl group, a 3-(trifluoromethyl)phenyl group, a 2-(trifluoromethyloxy)phenyl group, a 3-(trifluoromethyloxy)phenyl group, a 2-methylsulfamoylphenyl group, a 3-methylsulfamoylphenyl group, a 2-aminophenyl group, a 3-aminophenyl group, a 2-(methylamino)phenyl group, a 3-(methylamino)phenyl group, a 2-(dimethylamino)phenyl group, a 3-(dimethylamino)phenyl group, a 2-(acetylamino) phenyl group, a 3-(acetylamino)phenyl group, a 2-biphenyl group, a 3-biphenyl group, a 2-(methylsulfonyl)phenyl group, a 3-(methylsulfonyl)phenyl group, a 2-sulfamoylphenyl group, a 3-sulfamoylphenyl group, a 2-(methylaminosulfonyl)phenyl group, a 3-(methylaminosulfonyl)phenyl group, a 2-(dimethylaminosulfonyl)phenyl group, a 3-(dimethylaminosulfonyl)phenyl group, a 2-(dimethylsulfonyl) phenyl group, a 2-(methylsulfonylamino)phenyl group, a 3-(methylsulfonylamino)phenyl group, a 2-carbamoylphenyl group, a 3-carbamoylphenyl group, a 2-(methylcarbamoyl) phenyl group, a 3-(methylcarbamoyl)phenyl group, a 2-(dimethylcarbamoyl)phenyl group, a 3-(dimethylcarbamoyl)phenyl group, a 2,3-difluorophenyl group, a 3,4-difluorophenyl group, a 2,3-dichlorophenyl group, a 3,4-dichlorophenyl group, a 2,3-dibromophenyl group, a 3,4-dibromophenyl group, a 2,4-difluorophenyl group, a 2,4-dichlorophenyl group, a 2,5-dichlorophenyl group, a 2,6-dichlorophenyl group, a 2-chloro-3-fluorophenyl group, a 2-chloro-4-fluorophenyl group, a 2-chloro-5-fluorophenyl group, a 2-chloro-6-fluorophenyl group, a 3-chloro-2-fluorophenyl group, a 5-chloro-2-fluorophenyl group, a 5-bromo-2-chlorophenyl group, a 2-chloro-5-nitrophenyl group, a 2-chloro-3-methylphenyl group, a 2-chloro-5-methylphenyl group, a 2-chloro-3-(trifluoromethyl)phenyl group, a 2-chloro-5-(trifluoromethyl)phenyl group, a 2-chloro-3-hydroxyphenyl group, a 2-chloro-5-hydroxyphenyl group, a 2-chloro-3-methoxyphenyl group, a 2-chloro-5-methoxyphenyl group, a 2-chloro-3-methylsulfamoylphenyl group, a 2-chloro-5-methylsulfamoylphenyl group, a 2-chloro-5-methylsulfanylphenyl group, a 2-chloro-3-aminophenyl group, 2-chloro-5-aminophenyl group, a 2-chloro-3-(methylamino)phenyl group, a 2-chloro-5-(methylamino)phenyl group, a 2-chloro-3-(dimethylamino)phenyl group, a 2-chloro-5-(dimethylamino)phenyl group, a 2-chloro-3-(acetylamino)phenyl group, a 2-chloro-5-(acetylamino)phenyl group, a 2-chloro-3-(methylsulfonyl)phenyl group, a 2-chloro-5-(methylsulfonyl)phenyl group, a 2-chloro-3-(methylsulfonylamino)phenyl group, a 2-chloro-5-(methylsulfonylamino)phenyl group, a 2,3,4-trifluorophenyl group, a 2-chloro-3,4-difluorophenyl group, a 2-chloro-3,5-difluorophenyl group, a 2-chloro-3,6-difluorophenyl group, a 2-chloro-4,5-difluorophenyl group, a 2-chloro-4,6-difluorophenyl group, a 3-chloro-2,4-difluorophenyl group, a 3-chloro-2,5-difluorophenyl group, a 3-chloro-2,6-difluorophenyl group, a 2,3-dichloro-4-fluorophenyl group, a 3-chloro-2-fluoro-5-trifluoromethylphenyl group, a 2-chloro-3,5,6-trifluorophenyl group, a 3-chloro-2,4,5-trifluorophenyl group, a 3-chloro-2,4,6-trifluorophenyl group, a 2,3-dichloro-4,5,6-trifluorophenyl group, a 3,5-dichloro-3,4,6-trifluorophenyl group, a 2,6-dichloro-3,4,5-trifluorophenyl group, a perfluorophenyl group, a 2-biphenylyl group, a 3-biphenylyl group, a 4-biphenylyl group, a cyclopropyl group, a cyclobutyl group, a cyclopentyl group, a cyclohexyl group, a 2-hydroxycyclopropyl group, a 2-hydroxycyclobutyl group, a 3-hydroxycyclobutyl group, a 2-hydroxycyclopentyl group, a 3-hydroxycyclopentyl group, a 2-hydroxycyclohexyl group, a 3-hydroxycyclohexyl group, a 4-hydroxycyclohexyl group, a 4-indanyl group, an 1H-inden-4-yl group and the like.

Preferably is a 2-chlorophenyl group, a 2-bromophenyl group, a 2-ethylphenyl group, a 2-trifluoromethylphenyl group, a 2-hydroxyphenyl group, a 2-ethoxyphenyl group, a 2-(methylsulfonyl)phenyl group, a 2-(dimethylaminosulfonyl)phenyl group, a 2,3-difluorophenyl group, a 2,3-dichlorophenyl group, a 2-chloro-3-fluorophenyl group, a 2-chloro-4-fluorophenyl group, a 2-chloro-5-fluorophenyl group, a 2-chloro-6-fluorophenyl group, a 3-chloro-2-fluorophenyl group, a 5-bromo-2-chlorophenyl group, a 2-chloro-3-methylphenyl group, a 2-chloro-5-methylphenyl group, a 2-chloro-5-hydroxyphenyl group, a 2-chloro-3-methoxyphenyl group, a 2-chloro-5-methylsulfanylphenyl group, a 2-chloro-5-(methylsulfonyl)phenyl group, a 2-chloro-3,6-difluorophenyl group and a 3-chloro-2,6-difluorophenyl group.

More preferred are a 2,3-difluorophenyl group, a 2,3-dichlorophenyl group, a 2-chloro-3-fluorophenyl group and a 3-chloro-2-fluorophenyl group.

The "$C_{3-10}$ carbon ring group optionally substituted by 1 to 5 substituents selected from group A" for $R^1$ or group B (as defined below) is preferably a phenyl group, a 3,4-dichlorophenyl group, a 2-biphenylyl group, a cyclopropyl group, a cyclobutyl group, a cyclopentyl group, a cyclohexyl group, a 2-hydroxycyclopropyl group, a 2-hydroxycyclobutyl group, a 3-hydroxycyclobutyl group, a 2-hydroxycyclopentyl group, a 3-hydroxycyclopentyl group, a 2-hydroxycyclohexyl group, a 3-hydroxycyclohexyl group or a 4-hydroxycyclohexyl group, particularly preferably a phenyl group, a 3,4-dichlorophenyl group, a 2-biphenylyl group, a cyclopropyl group, a cyclobutyl group, a cyclopentyl group or a cyclohexyl group, more preferably a phenyl group or a cyclohexyl group.

The "$C_{3-10}$ carbon ring group optionally substituted by 1 to 5 substituents selected from group A" for $R^{32}$ or $R^{33}$ is preferably a phenyl group or a cyclohexyl group.

The "heterocyclic group" means a group derived from a saturated or unsaturated (including partially or completely unsaturated) monocyclic 5-membered or 6-membered heterocycle containing, besides carbon atom, at least one, preferably 1 to 4 hetero atoms selected from nitrogen atom, oxygen atom and sulfur atom, or a fused ring of the heterocycles, or a fused ring of a $C_{3-10}$ carbon ring selected from benzene, cyclopentane and cyclohexane and the heterocycle (hereinafter sometimes to be abbreviated as fused heterocycle).

Examples of the "saturated monocyclic 5-membered or 6-membered heterocyclic group" include a pyrrolidinyl group, a tetrahydrofuryl group, a tetrahydrothienyl group, an imidazolidinyl group, a pyrazolidinyl group, a 1,3-a dioxolanyl group, a 1,3-oxathiolanyl group, an oxazolidinyl group, a thiazolidinyl group, a piperidinyl group, a piperazinyl group, a tetrahydropyranyl group, a tetrahydrothiopyranyl group, a dioxanyl group, a morpholinyl group, a thiomorpholinyl group, a 2-oxopyrrolidinyl group, a 2-oxopiperidinyl group, a 4-oxopiperidinyl group, a 2,6-dioxopiperidinyl group and the like. Preferred is a pyrrolidinyl group, a piperidinyl group or a morpholinyl group.

Examples of the "unsaturated monocyclic 5-membered or 6-membered heterocyclic group" include a pyrrolyl group, a furyl group, a thienyl group, an imidazolyl group, a 1,2-dihydro-2-oxoimidazolyl group, a pyrazolyl group, a diazolyl group, an oxazolyl group, an isoxazolyl group, a thiazolyl group, an isothiazolyl group, a 1,2,4-triazolyl group, a 1,2,3-triazolyl group, a tetrazolyl group, a 1,3,4-oxadiazolyl group, a 1,2,4-oxadiazolyl group, a 1,3,4-thiadiazolyl group, a 1,2,4-thiadiazolyl group, a furazanyl group, a pyridyl group, a pyrimidinyl group, a 3,4-dihydro-4-oxopyrimidinyl group, a pyridazinyl group, a pyrazinyl group, a 1,3,5-triazinyl group, an imidazolinyl group, a pyrazolinyl group, an oxazolinyl group (e.g., 2-oxazolinyl group, 3-oxazolinyl group, 4-oxazolinyl group etc.), an isoxazolinyl group, a thiazolinyl group, an isothiazolinyl group, a pyranyl group, a 2-oxopyranyl group, a 2-oxo-2,5-dihydrofuranyl group, a 1,1-dioxo-1H-isothiazolyl group and the like. Preferred is a pyrrolyl group, a furyl group, a thienyl group, an imidazolyl group, a pyrazolyl group, an oxazolyl group, an isoxazolyl group, a thiazolyl group, an isothiazolyl group, a pyridyl group, a 2-oxo-2,5-dihydrofuranyl group or a 1,1-dioxo-1H-isothiazolyl group.

Examples of the "fused heterocycle group" include an indolyl group (e.g., 2-indolyl group, 3-indolyl group, 4-indolyl group, 7-indolyl group etc.), an isoindolyl group, a 1,3-dihydro-1,3-dioxoisoindolyl group, a benzofuranyl group (e.g., 2-benzofuranyl group, 4-benzofuranyl group, 7-benzofuranyl group etc.), an indazolyl group, an isobenzofuranyl group, a benzothiophenyl group (e.g., 2-benzothiophenyl group, 4-benzothiophenyl group, 7-benzothiophenyl group etc.), a benzoxazolyl group (e.g., 2-benzoxazolyl group, 4-benzoxazolyl group, 7-benzoxazolyl group etc.), a benzimidazolyl group (e.g., 2-benzimidazolyl group, 4-benzimidazolyl group, 7-benzimidazolyl group etc.), a benzothiazolyl group (e.g., 2-benzothiazolyl group, 4-benzothiazolyl group, 7-benzothiazolyl group etc.), an indolizinyl group, a quinolyl group, an isoquinolyl group, a 1,2-dihydro-2-oxoquinolyl group, a quinazolinyl group, a quinoxalinyl group, a cinnolinyl group, a phthalazinyl group, a quinolizinyl group, a purinyl group, a pteridinyl group, an indolinyl group, an isoindolinyl group, a 5,6,7,8-tetrahydroquinolyl group, a 1,2,3,4-tetrahydroquinolyl group, a 2-oxo-1,2,3,4-tetrahydroquinolyl group, a benzo[1,3]dioxolyl group, a 3,4-methylenedioxypyridyl group, a 4,5-ethylenedioxypyrimidinyl group, a chromenyl group, a chromanyl group, an isochromanyl group and the like.

Preferred is a fused ring of a saturated or unsaturated monocyclic 5-membered or 6-membered heterocycle and a benzene ring, specifically, an indolyl group, a benzofuranyl group, a benzothiophenyl group, a benzoxazolyl group, a benzimidazolyl group, a benzothiazolyl group, a benzo[1,3]dioxolyl group and the like.

The "heterocyclic group optionally substituted by 1 to 5 substituents selected from group A" is the above-defined "heterocyclic group" optionally substituted by 1 to 5, preferably 1 to 3, substituents selected from the above-defined "group A", and includes an unsubstituted "heterocyclic group". In addition, the position of substitution is not particularly limited as long as it is a substitutable position.

The "heterocyclic group" is preferably a monocyclic heterocycle containing 1 or 2 hetero atoms, or a heterocycle which is a fused ring of the monocyclic heterocycle with a benzene ring.

Examples of the "heterocyclic group optionally substituted by 1 to 5 substituents selected from group A" include a pyrrolidinyl group, a piperidinyl group, a morpholinyl group, a pyrrolyl group, a 2-pyrrolyl group, a 3-pyrrolyl group, a 2-furyl group, a 3-furyl group, a 2-thienyl group, a 3-thienyl group, a 4,5-dichlorothiophen-3-yl group, a 2-oxo-2,5-dihydrofuran-3-yl group, a 1,1-dioxo-1H-isothiazol-5-yl group, a 4-methylthiazol-5-yl group, an imidazolyl group, a 2-imidazolyl group, a 3-imidazolyl group, a 4-imidazolyl group, a pyrazolyl group, a 2-oxazolyl group, a 3-isoxazolyl group, a 2-thiazolyl group, a 3-isothiazolyl group, a 2-pyridyl group, a 3-fluoropyridin-2-yl group, a 3-chloropyridin-2-yl group, a 3-chloro-4-fluoropyridin-2-yl group, a 3,5-dichloropyridin-2-yl group, a 3-pyridyl group, a 2-fluoropyridin-3-yl group, a 2-chloropyridin-3-yl group, a 2-chloro-4-fluoropyridin-3-yl group, a 2-chloro-5-fluoropyridin-3-yl group, a 2,5-dichloropyridin-3-yl group, a 2-chloro-6-fluoropyridin-3-yl group, a 2,6-dichloropyridin-3-yl group, a 4-pyridyl group, a 2-fluoropyridin-4-yl group, a 2-chloropyridin-4-yl group, a 2-chloro-3-fluoropyridin-4-yl group, a 2,3-difluoropyridin-4-yl group, a 2,3-dichloropyridin-4-yl group, a 2,5-dichloropyridin-4-yl group, a 2-chloro-6-fluoropyridin-4-yl group, a 2,6-dichloropyridin-4-yl group, a 2-chloro-3,6-difluoropyridin-4-yl group, a 2-chloro-3,5-difluoropyridin-4-yl group, a 2,3,6-trifluoropyridin-4-yl group, a 2,3,5,6-tetrafluoropyridin-4-yl group, a 2-indolyl group, a 3-indolyl group, a 4-indolyl group, a 7-indolyl group, a 2-benzofuranyl group, a 4-benzofuranyl group, a 7-benzofuranyl group, a 2-benzothiophenyl group, a 4-benzothiophenyl group, a 7-benzothiophenyl group, a 2-benzimidazolyl group, a 4-benzimidazolyl group, a 2-benzoxazolyl group, a 4-benzoxazolyl group, a 7-benzoxazolyl group, a 2-benzothiazolyl group, a 4-benzothiazolyl group, a 7-benzothiazolyl group, a 2-benzo[1,3]dioxolyl group, a 4-benzo[1,3]dioxolyl group, a 5-benzo[1,3]dioxolyl group and the like.

The "heterocyclic group optionally substituted by 1 to 5 substituents selected from group A" for $R^1$ or group B (as defined below) is preferably a morpholinyl group, a 4-methylthiazol-5-yl group, an imidazolyl group, a 2-pyridyl group or a 2-benzothiophenyl group.

The "heterocyclic group optionally substituted by 1 to 5 substituents selected from group A" for $R^{32}$ or $R^{33}$ is preferably a pyrrolidinyl group.

The "$C_{1-10}$ alkyl group optionally substituted by 1 to 3 substituents selected from halogen atom and group B (as defined below)" is a $C_{1-10}$ alkyl group optionally substituted by substituent(s) selected from the above-defined "halogen atom" and the below-defined "group B", and may be an unsubstituted alkyl group. The alkyl moiety is a straight chain or branched chain alkyl group having 1 to 10 carbon atoms, and specifically a methyl group, an ethyl group, a propyl group, an isopropyl group, a butyl group, an isobutyl group, a sec-butyl group, a tert-butyl group, a pentyl group, an isopentyl group, a 1-methylbutyl group, a 1-ethylpropyl group, a 2-ethylpropyl group, a 1,1-dimethylpropyl group, a 1,2-dimethylpropyl group, a tert-pentyl group, a hexyl group, an isohexyl group, a 1-methylpentyl group, a 1,1-dimethylbutyl group, a 1,2-dimethylbutyl group, a 1,3-dimethylbutyl group, a 1-ethylbutyl group, a 1-ethyl-1-methylpropyl group, a 1-ethyl-2-methylpropyl group, a 1,1,2-trimethylpropyl group, a 1,2,2-trimethylpropyl group, a 1-ethyl-1-methylpropyl group, a heptyl group, an isoheptyl group, a 1-methylhexyl group, a 1,1-dimethylpentyl group, a 1,2-dimethylpentyl group, a 1,3-dimethylpentyl group, a 1,4-dimethylpentyl group, a 1,1,2-trimethylbutyl group, a 1,1,3-trimethylbutyl group, a 1,2,2-trimethylbutyl group, a 1,2,3-trimethylbutyl group, a 1,3,3-trimethylbutyl group, a 1-ethylpentyl group, a 1-ethyl-2-methylbutyl group, a 1-ethyl-3-methylbutyl group, a 2-ethyl-1-methylbutyl group, a 1-propylbutyl group, a 1-ethyl-2,2-dimethylpropyl group, a 1-isopropyl-2-methylpropyl group, a 1-isopropyl-1-methylpropyl group, a 1,1-diethylpropyl group, a 1,1,2,2-tetramethylpropyl group, a 1-isopropylbutyl group, a 1-ethyl-1-methylbutyl group, an octyl group, a nonyl group, a decanyl group and the like, and preferred is a straight chain or branched chain alkyl group having 1 to 6 carbon atoms, particularly preferably a branched chain alkyl group having 1 to 6 carbon atoms. In addition, the position of substitution is not particularly limited as long as it is a substitutable position.

The "group B" is a group containing the above-defined "$C_{3-10}$ carbon ring group optionally substituted by 1 to 5 substituents selected from group A", the above-defined "heterocyclic group optionally substituted by 1 to 5 substituents selected from group A", $—OR^{a4}$, $—SR^{a4}$, $—NR^{a4}R^{a5}$, $—CONR^{a4}R^{a5}$, $—SO_2NR^{a4}R^{a5}$, $—COR^{a6}$, $—NR^{a4}COR^{a6}$, $—SO_2R^{a6}$, $—NR^{a4}SO_2R^{a6}$, $—COOR^{a4}$ and $—NR^{a5}COOR^{a6}$ wherein $R^{a4}$ and $R^{a5}$ are the same or different and each is a hydrogen atom, the above-defined "$C_{1-4}$ alkyl group", the above-defined "$C_{3-10}$ carbon ring group optionally substituted by 1 to 5 substituents selected from group A" or the above-defined "heterocyclic group optionally substituted by 1 to 5 substituents selected from group A", and $R^{a6}$ is the above-defined "$C_{1-4}$ alkyl group", the above-defined "$C_{3-10}$ carbon ring group optionally substituted by 1 to 5 substituents selected from group A" or the above-defined "heterocyclic group optionally substituted by 1 to 5 substituents selected from group A".

Examples of "$—OR^{a4}$" include a hydroxy group, a methoxy group, an ethoxy group, a propoxy group, an isopropoxy group, a tert-butoxy group and the like.

Examples of "$—SR^{a4}$" include a mercapto group, a methylsulfanyl group, an ethylsulfanyl group, a propylsulfanyl group, an isopropylsulfanyl group, a tert-butylsulfanyl group and the like.

Examples of "$—NR^{a4}R^{a5}$" include an amino group, a methylamino group, an ethylamino group, a propylamino group, an isopropylamino group, a tert-butylamino group, a dimethylamino group, a diethylamino group, an N-ethyl-N-methylamino group, an N-methyl-N-propylamino group, an N-isopropyl-N-methylamino group, an N-benzyl-N-methylamino group and the like.

Examples of "$—CONR^{a4}R^{a5}$" include a carbamoyl group, a methylaminocarbonyl group, an ethylaminocarbonyl group, a propylaminocarbonyl group, an isopropylaminocarbonyl group, a tert-butylaminocarbonyl group, a dimethylaminocarbonyl group, a diethylaminocarbonyl group, an N-methyl-N-ethylaminocarbonyl group and the like.

Examples of "$—SO_2NR^{a4}R^{a5}$", include a sulfamoyl group, a methylaminosulfonyl group, an ethylaminosulfonyl group, a propylaminosulfonyl group, an isopropylaminosulfonyl group, a tert-butylaminosulfonyl group, a dimethylaminosulfonyl group, a diethylaminosulfonyl group, an N-methyl-N-ethylaminosulfonyl group and the like.

Examples of "$—COR^{a6}$" include an acetyl group, a propionyl group, a butyryl group, an isobutyryl group, a pivaloyl group and the like.

Examples of "$—NR^{a4}COR^{a6}$" include an acetylamino group, a propionylamino group, a butyrylamino group, an isobutyrylamino group, a pivaloylamino group, an N-acetyl-N-methylamino group and the like.

Examples of "$—SO_2R^{a6}$" include a methylsulfonyl group, an ethylsulfonyl group, a propylsulfonyl group, an isopropylsulfonyl group, a tert-butylsulfonyl group and the like.

Examples of "$—NR^{a4}SO_2R^{a6}$" include a methylsulfonylamino group, an ethylsulfonylamino group, a propylsulfonylamino group, an isopropylsulfonylamino group, a tert-butylsulfonylamino group, an N-methyl-N-(methylsulfonyl) amino group and the like.

Examples of "$—COOR^{a4}$" include a carboxyl group, a methoxycarbonyl group, an ethoxycarbonyl group, a propoxycarbonyl group, an isopropoxycarbonyl group, a tert-butoxycarbonyl group and the like.

Examples of "$—NR^{a5}COOR^{a6}$" include a methoxycarbonylamino group, an ethoxycarbonylamino group, a propoxycarbonylamino group, an isopropoxycarbonylamino group, a tert-butoxycarbonylamino group and the like.

Examples of the above-mentioned "$C_{1-10}$ alkyl group optionally substituted by 1 to 3 substituents selected from halogen atom and the above-mentioned group B" include a methyl group, an ethyl group, a propyl group, an isopropyl group, a butyl group, an isobutyl group, a sec-butyl group, a tert-butyl group, a pentyl group, an isopentyl group, a 1-methylbutyl group, a 1-ethylpropyl group, a 2-ethylpropyl group, a 1,1-dimethylpropyl group, a 1,2-dimethylpropyl group, a tert-pentyl group, a hexyl group, an isohexyl group, a 1-methylpentyl group, a 1,1-dimethylbutyl group, a 1,2-dimethylbutyl group, a 1,3-dimethylbutyl group, a 1-ethylbutyl group, a 1-ethyl-1-methylpropyl group, a 1-ethyl-2-methylpropyl group, a 1,1,2-trimethylpropyl group, a 1,2,2-trimethylpropyl group, a 1-ethyl-1-methylpropyl group, a heptyl group, an isoheptyl group, a 1-methylhexyl group, a 1,1-dimethylpentyl group, a 1,2-dimethylpentyl group, a 1,3-dimethylpentyl group, a 1,4-dimethylpentyl group, a 1,1,2-trimethylbutyl group, a 1,1,3-trimethylbutyl group, a 1,2,2-trimethylbutyl group, a 1,2,3-trimethylbutyl group, a 1,3,3-trimethylbutyl group, a 1-ethylpentyl group, a 1-ethyl-2-methylbutyl group, a 1-ethyl-3-methylbutyl group, a 2-ethyl-1-methylbutyl group, a 1-propylbutyl group, a 1-ethyl-2,2-dimethylpropyl group, a 1-isopropyl-2-methylpropyl group, a 1-isopropyl-1-methylpropyl group, a 1,1-diethylpropyl group, a 1,1,2,2-tetramethylpropyl group, a 1-isopropylbutyl group, a 1-ethyl-1-methylbutyl group, an octyl group, a nonyl group, a decanyl group, a fluoromethyl group, a trifluoromethyl group, a chloroethyl group, a 2-fluoroethyl group, a 2-chloroethyl group, a 3-fluoropropyl group, a 2-chloropropyl group, a 2,2,2-trifluoroethyl group, a 2-hydroxyethyl group, a 2-hydroxypropyl group, a 2-hydroxy-1-methylethyl group, a 2-hydroxy-1,1-dimethylethyl group, a 1-(hydroxymethyl)propyl group, a 3-hydroxypropyl group, a 2-hydroxybutyl group, a 4-hydroxybutyl group, a 2-hydroxypentyl group, a 5-hydroxypentyl group, a 2,3-dihydroxypropyl group, a 2,3-dihydroxybutyl group, a 2-hydroxy-1-(hydroxymethyl)ethyl group, a 2-hydroxy-2-methylpropyl group, a 1-(hydroxymethyl)butyl group, a 1-(hydroxymethyl)-2-methylpropyl group, a 1-(hydroxymethyl)-2,2-dimethylpropyl group, a 1-(hydroxymethyl)-2-methylbutyl group, a 2-hydroxy-1-phenylethyl group, a 2-hydroxy-2-phenylethyl group, a 1-(hydroxymethyl)-2-phenylethyl group, a 1-(hydroxymethyl)-3-methylbutyl group, a 2-ethyl-1-(hydroxymethyl)butyl group, a 3-hydroxy-1-methylpropyl group, a 1,1-dimethyl-3-hydroxypropyl group, a 1,2-dimethyl-3-hydroxypropyl group, a 1-isopropyl-3-hydroxypropyl group, a 2,2-dimethyl-1-(2-hydroxyethyl)propyl group, a 1-ethyl-3-hydroxypropyl group, a 2-hydroxy-1-isopropylpropyl group, a 1-ethyl-1-(hydroxymethyl)propyl group, a 1,1-dimethyl-2-hydroxypropyl group, a 1,2-dimethyl-2-hydroxypropyl group, a 1-ethyl-2-hydroxypropyl group, a 4-hydroxy-1-methylbutyl group, a 2-ethyl-1-(hydroxymethyl)-2-methylbutyl group, a 3,3-dimethyl-1-(hydroxymethyl)butyl group, a 1-(hydroxymethyl)pentyl group, a 4-methyl-1-(hydroxymethyl)pentyl group, a methoxymethyl group, a 2-methoxyethyl group, a methylsulfanylmethyl group, a 2-(methylsulfanyl)ethyl group, a 2-aminoethyl group, a 2-(dimethylamino)ethyl group, a carboxymethyl group, a 2-carboxyethyl group, a 2-carboxypropyl group, a 3-carboxypropyl group, a carbamoylmethyl group, a 2-carbamoylethyl group, a methylaminocarbonylmethyl group, a dimethylaminocarbonylmethyl group, a 2-(phenylaminocarbonyl)ethyl group, a 2-oxopropyl group, a methylsulfonylmethyl group, a 2-(methylsulfonyl)ethyl group, a sulfamoylmethyl group, methylaminosulfonylmethyl group, dimethylaminosulfonylmethyl group, a tert-butylaminosulfonylmethyl group, a 2-(acetylamino)ethyl group, a 2-(methylsulfonylamino)ethyl group, a 2-(ethoxycarbonylamino)ethyl group, a benzyl group, a phenethyl group, a 3-phenylpropyl group, a 4-phenylbutyl group, a 2-biphenylylmethyl group, a 3,4-dichlorobenzyl group, 2-hydroxy-2-phenylethyl group, a cyclopentylmethyl group, a cyclohexylmethyl group, a 2-cyclohexylethyl group, a 1-cyclohexyl-2-hydroxyethyl group, a 1-cyclohexylmethyl-2-hydroxyethyl group, a phenylaminocarbonylmethyl group, a 2-pyridin-2-ylethyl group, a 2-imidazol-1-ylethyl group, a benzothiophen-2-ylmethyl group, a 2-benzothiophen-2-ylethyl group, a 2-morpholinoethyl group, a 2-(4-methylthiazolin-5-yl)ethyl group, a 1-carboxyethyl group, a 1-carbamoylethyl group, a 1-carboxy-2-methylpropyl group, a 1-carbamoyl-2-methylpropyl group, a 2-hydroxy-1-(hydroxymethyl)propyl group, a 1-(hydroxymethyl)-2-mercaptoethyl group, a 1-(hydroxymethyl)-3-(methylsulfanyl)propyl group, a 2-carboxy-1-(hydroxymethyl)ethyl group, a 2-carbamoyl-1-(hydroxymethyl)ethyl group, a 2-(indol-3-yl)-1-(hydroxymethyl)ethyl group, a 2-(imidazol-4-yl)-1-(hydroxymethyl)ethyl group, a 2-(4-hydroxyphenyl)-1-(hydroxymethyl)ethyl group, a 3-carbamoyl-1-(hydroxymethyl)propyl group, a 5-amino-1-(hydroxymethyl)pentyl group and the like.

The "$C_{1-10}$ alkyl group optionally substituted by 1 to 3 substituents selected from halogen atom and the above-mentioned group B" for $R^1$ is preferably a methyl group, an ethyl group, a propyl group, an isopropyl group, a butyl group, an isobutyl group, a tert-butyl group, a 2-fluoroethyl group, a 2,2,2-trifluoroethyl group, a 2-hydroxyethyl group, a 2-hydroxypropyl group, a 2-hydroxy-1-methylethyl group, a 2-hydroxy-1,1-dimethylethyl group, a 1-(hydroxymethyl)propyl group, a 3-hydroxypropyl group, a 4-hydroxybutyl group, a 5-hydroxypentyl group, a 2,3-dihydroxypropyl group, a 2-hydroxy-1-(hydroxymethyl)ethyl group, a 2-hydroxy-2-methylpropyl group, a 1-(hydroxymethyl)butyl group, a 1-(hydroxymethyl)-2-methylpropyl group, a 1-(hydroxymethyl)-2,2-dimethylpropyl group, a 1-(hydroxymethyl)-2-methylbutyl group, a 2-hydroxy-1-phenylethyl group, a 2-hydroxy-2-phenylethyl group, a 1-(hydroxymethyl)-2-phenylethyl group, a 1-(hydroxymethyl)-3-methylbutyl group, a 2-methoxyethyl group, a methylsulfanylmethyl group, a 2-(methylsulfanyl)ethyl group, a 2-aminoethyl group, a 2-(dimethylamino)ethyl group, a carboxymethyl group, a 2-carboxyethyl group, a 3-carboxypropyl group, a carbamoylmethyl group, a 2-carbamoylethyl group, a methylaminocarbonylmethyl group, a dimethylaminocarbonylmethyl group, a 2-(phenylaminocarbonyl)ethyl group, a 2-oxopropyl group, a methylsulfonylmethyl group, a 2-(methylsulfonyl)ethyl group, a sulfamoylmethyl group, a methylaminosulfonylmethyl group, a dimethylaminosulfonylmethyl group, a tert-butylaminosulfonylmethyl group, a 2-(acetylamino)ethyl group, a 2-(methylsulfonylamino)ethyl group, a 2-(ethoxycarbonylamino)ethyl group, a benzyl group, a phenethyl group, a 3-phenylpropyl group, a 4-phenylbutyl group, a 2-biphenylylmethyl group, a 3,4-dichlorobenzyl group, a cyclopentylmethyl group, a cyclohexylmethyl group, a 1-cyclohexyl-2-hydroxyethyl group, a 1-cyclohexylmethyl-2-hydroxyethyl group, a 2-pyridin-2-ylethyl group, a 2-imidazol-1-ylethyl group, a benzothiophen-2-ylmethyl group, a 2-morpholinoethyl group or a 2-(4-methylthiazolin-5-yl)ethyl group, particularly preferably an alkyl group branched at the 1-position and/or substituted by a hydroxy group, specifically a 2-hydroxy-1-methylethyl group, a 2-hydroxy-1-(hydroxymethyl)ethyl group, a 1-(hydroxymethyl)-2-methylpropyl group, a 1-(hydroxymethyl)-2,2-dimethylpropyl group, a 1-(hydroxymethyl)-2-methylbutyl group or a 1-(hydroxymethyl)-2-phenylethyl group. When the particularly preferable substituent is an optically active form, an S form is more preferable.

The "$C_{1-10}$ alkyl group optionally substituted by 1 to 3 substituents selected from a halogen atom and the above-mentioned group B" for $R^1$ is most preferably a 1-(hydroxymethyl)-2-methylpropyl group, more preferably an S form.

The "$C_{1-10}$ alkyl group optionally substituted by 1 to 3 substituents selected from a halogen atom and the above-mentioned group B" for $R^{32}$ or $R^{33}$ is preferably a methyl group, an ethyl group or a trifluoromethyl group.

The "$C_{1-10}$ alkyl group optionally substituted by 1 to 3 substituents selected from a halogen atom and the above-mentioned group B" for $R^{a7}$ or $R^{a8}$ is preferably a methyl group, an ethyl group, a propyl group, an isopropyl group, a 2-hydroxyethyl group, a 3-hydroxypropyl group or a cyclohexylmethyl group, more preferably a methyl group, an ethyl group or an isopropyl group, particularly preferably a methyl group.

Examples of the "fused ring" optionally formed by $R^4$ and $R^5$ together with a benzene ring bonded thereto include naphthalen-1-yl and the like.

The "5- or 6-membered heterocycle" optionally formed by $R^{c5}$ and $R^{c6}$ together with the adjacent nitrogen atom is, of the above-mentioned "heterocyclic group", a saturated monocyclic 5-membered or 6-membered heterocycle containing a nitrogen atom, and specifically includes pyrrolidine, piperidine and the like.

The "5- or 6-membered heterocycle" optionally formed by $R^{c8}$ and $R^{c9}$ together with the adjacent nitrogen atom is, of the above-mentioned "heterocyclic group", a saturated monocyclic 5-membered or 6-membered heterocycle containing a nitrogen atom, and specifically includes pyrrolidine, piperidine and the like.

m is 0, 1, 2 or 3, and when m is 2 or 3, each $R^6$ may be the same or different.

The group represented by the formula:

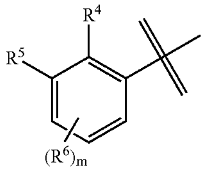

wherein $R^4$, $R^5$, $R^6$ and m are as defined above, is preferably a group represented by the formula:

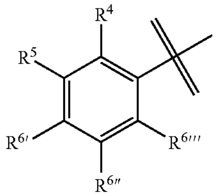

wherein $R^{6'}$, $R^{6''}$ and $R^{6'''}$ are the same or different and each is a hydrogen atom (i.e., when m is 0) or a group selected from and the above-defined "group A", and $R^4$ and $R^5$ are as defined above.

$R^4$ is preferably a phenyl group, the above-defined "halogen atom", the above-defined "$C_{1-4}$ alkyl group", the above-defined "halo $C_{1-4}$ alkyloxy group", the above-defined "—$OR^{a1}$", the above-defined "—$NR^{a1}R^{a2}$", the above-defined "—$SO_2NR^{a1}R^{a2}$", the above-defined "—$NR^{a1}COR^{a3}$", the above-defined "—$SO_2R^{a3}$", the above-defined "—$NR^{a1}SO_2R^{a3}$" or the above-defined "—$COOR^{a1}$", more preferably "halogen atom", "$C_{1-4}$ alkyl group", "halo $C_{1-4}$ alkyloxy group", "—$OR^{a1}$" or "—$NR^{a1}R^{a2}$", particularly preferably "halogen atom".

$R^5$ is preferably a hydrogen atom, a cyano group, a nitro group, the above-defined "halogen atom", the above-defined "$C_{1-4}$ alkyl group", the above-defined "halo $C_{1-4}$ alkyl group", the above-defined "—$OR^{a1}$", the above-defined "—$SR^{a1}$", the above-defined "—$NR^{a1}R^{a2}$", the above-defined "—$CONR^{a1}R^{a2}$", the above-defined "—$SO_2NR^{a1}R^{a2}$" or the above-defined "—$NR^{a1}COR^{a3}$", more preferably a hydrogen atom, "halogen atom" or "$C_{1-4}$ alkyl group", particularly preferably "halogen atom".

$R^6$ is preferably the above-defined "halogen atom", the above-defined "$C_{1-4}$ alkyl group", the above-defined "—$OR^{a1}$", the above-defined "—$SR^{a1}$" or the above-defined "—$SO_2R^{a3}$", more preferably "halogen atom".

$R^{6'}$ and $R^{6'''}$ are preferably the same or different and each is a hydrogen atom or the above-defined "halogen atom".

$R^{6''}$ is preferably a hydrogen atom, the above-defined "halogen atom", the above-defined "$C_{1-4}$ alkyl group", the above-defined "—$OR^{a1}$", the above-defined "—$SR^{a1}$" or the above-defined "—$SO_2R^{a3}$", more preferably a hydrogen atom, "halogen atom", "$C_{1-4}$ alkyl group" or "—$SR^{a1}$", more preferably a hydrogen atom.

Preferable examples of the above-mentioned substituted phenyl group include a 2-chlorophenyl group, a 2-bromophenyl group, a 2-ethylphenyl group, a 2-hydroxyphenyl group, a 2-ethoxyphenyl group, a 2,3-difluorophenyl group, a 2,3-dichlorophenyl group, a 2-chloro-3-fluorophenyl group, a 2-chloro-4-fluorophenyl group, a 2-chloro-5-fluorophenyl group, a 2-chloro-6-fluorophenyl group, a 3-chloro-2-fluorophenyl group, a 5-bromo-2-chlorophenyl group, a 2-chloro-5-methylphenyl group, a 2-chloro-5-hydroxyphenyl group, a 2-chloro-5-(methylsulfonyl)phenyl group, a 2-chloro-3,6-difluorophenyl group, a 3-chloro-2,4-difluorophenyl group, a 3-chloro-2,6-difluorophenyl group, a 2-chloro-3-methylphenyl group, a 3-chloro-2-methylphenyl group, a 2-chloro-3-methoxyphenyl group, a 3-chloro-2-methoxyphenyl group, a 2-trifluoromethylphenyl group, a 2-(trifluoromethyloxy)phenyl group, 2-(methylamino)phenyl group, 2-(dimethylamino)phenyl group, a 2-(diethylamino)phenyl group, a 2-(N-ethyl-N-methylamino)phenyl group, a 2-(N-isopropyl-N-methylamino)phenyl group, a 2-(N-benzyl-N-methylamino)phenyl group, a 2-(N-acetyl-N-methylamino)phenyl group, a 2-(N-methyl-N-methylsulfonylamino)phenyl group, a 2-carboxyphenyl group, a 2-biphenylyl group, a 2-(methylsulfonyl)phenyl group, a 2-chloro-5-methylsulfanylphenyl group, a 2-chloro-5-methylphenyl group, a 2-(methylaminosulfonyl)phenyl group and a 2-(dimethylaminosulfonyl)phenyl group.

Preferred is a 2-chlorophenyl group, a 2-bromophenyl group, a 2-ethylphenyl group, a 2-hydroxyphenyl group, a 2-ethoxyphenyl group, a 2,3-difluorophenyl group, a 2,3-dichlorophenyl group, a 2-chloro-3-fluorophenyl group, a 2-chloro-4-fluorophenyl group, a 2-chloro-5-fluorophenyl group, a 2-chloro-6-fluorophenyl group, a 3-chloro-2-fluorophenyl group, a 5-bromo-2-chlorophenyl group, a 2-chloro-5-methylphenyl group, a 2-chloro-5-hydroxyphenyl group, a 2-chloro-5-(methylsulfonyl)phenyl group, a 2-chloro-3,6-difluorophenyl group, a 3-chloro-2,6-difluorophenyl group, a 2-chloro-3-methylphenyl group, a 2-chloro-3-methoxyphenyl group, a 2-trifluoromethylphenyl group, a 2-(methylsulfonyl)phenyl group, a 2-chloro-5-methylsulfanylphenyl group and a 2-(dimethylaminosulfonyl) phenyl group.

More preferred is a 2,3-difluorophenyl group, a 2,3-dichlorophenyl group, a 2-chloro-3-fluorophenyl group or a 3-chloro-2-fluorophenyl group.

Preferable examples of $R^1$ include the above-defined "$C_{3-10}$ carbon ring group optionally substituted by 1 to 5 substituents selected from group A", the above-defined "heterocyclic group optionally substituted by 1 to 5 substituents selected from group A", the above-defined "—$OR^{a4}$" (specifically preferred is a methoxy group), the above-defined "—$NR^{a4}R^{a5}$" (specifically preferred is an amino group, a methylamino group, an ethylamino group and a dimethylamino group), the above-defined "—$NR^{a4}COR^{a6}$" (specifically preferred is an acetylamino group), the above-defined "—$NR^{a4}SO_2R^{a6}$" (specifically preferred is a methylsulfonylamino group and an N-methyl-N-(methylsulfonyl)amino group), the above-defined "—$NR^{a5}COOR^{a6}$" (specifically preferred is a methoxycarbonylamino group) and the above-defined "$C_{1-10}$ alkyl group optionally substituted by 1 to 3 substituents selected from halogen atom and the above-mentioned group B", more preferably "$C_{3-10}$ carbon ring group optionally substituted by 1 to 5 substituents selected from group A" and "$C_{1-10}$ alkyl group optionally substituted by 1 to 3 substituents selected from halogen atom and the above-mentioned group B", still more preferably "$C_{1-10}$ alkyl group optionally substituted by 1 to 3 substituents selected from halogen atom and the above-mentioned group B".

Preferable examples of $R^{31}$ include a hydrogen atom, a cyano group, a hydroxy group, the above-defined "halogen atom" and the above-defined "$C_{1-4}$ alkoxy group", more preferably a hydrogen atom, a cyano group, "halogen atom" and "$C_{1-4}$ alkoxy group", still more preferably a hydrogen atom, a cyano group and "$C_{1-4}$ alkoxy group", particularly preferably a hydrogen atom.

Preferable examples of $R^{32}$ include a hydrogen atom, a cyano group, the above-defined "halogen atom", the above-defined "heterocyclic group optionally substituted by 1 to 5 substituents selected from group A", the above-defined "$C_{1-10}$ alkyl group optionally substituted by 1 to 3 substituents selected from halogen atom and the above-mentioned group B", the above-defined "—$OR^{a7}$", the above-defined "—$SR^{a7}$", the above-defined "—$NR^{a7}R^{a8}$, the above-defined "—$COOR^{a10}$" and the above-defined "—N═CH—$NR^{a10}R^{a11}$", more preferably a hydrogen atom, —$OR^{a7}$", "—$SR^{a7}$" and "—$NR^{a7}R^{a8}$", still more preferably a hydrogen atom and "—$OR^{a7}$", particularly preferably "—$OR^{a7}$".

As other embodiment for $R^{32}$, preferred is the above-defined "halogen atom", the above-defined "$C_{1-10}$ alkyl group optionally substituted by 1 to 3 substituents selected from halogen atom and the above-mentioned group B" or the above-defined "—$OR^{a7}$", more preferably "—$OR^{a7}$", wherein $R^{a7}$ is preferably the above-defined "$C_{1-10}$ alkyl group optionally substituted by 1 to 3 substituents selected from a halogen atom and the above-mentioned group B".

As $R^{33}$, preferred is a hydrogen atom, the above-defined "$C_{1-10}$ alkyl group optionally substituted by 1 to 3 substituents selected from halogen atom and the above-mentioned group B", the above-defined "—$OR^{a7}$" or the above-defined "—$NR^{a7}R^{a8}$", more preferably a hydrogen atom, "—$OR^{a7}$" or "—$NR^{a7}R^{a8}$", still more preferably a hydrogen atom or "—$OR^{a7}$", particularly preferably a hydrogen atom.

One of $R^{32}$ and $R^{33}$ is preferably a hydrogen atom, and the other is preferably the above-defined "—$OR^{a7}$".

It is preferable that $R^{31}$ be a hydrogen atom and $R^{32}$ or $R^{33}$ be other than a hydrogen atom.

$R^{C1}$ is preferably the above-defined "carboxyl-protecting group". Particularly, $R^{C1}$, which is a carboxyl-protecting group, is $R^{C1'}$.

$R^{C5}$ and $R^{C6}$ are the same or different and each is preferably the above-defined "$C_{1-4}$ alkyl group", more preferably the same $C_{1-4}$ alkyl group.

$R^{C7}$, $R^{C8}$ and $R^{C9}$ are the same or different and each is preferably the above-defined "$C_{1-4}$ alkyl group", preferably the same $C_{1-4}$ alkyl group.

Compound [I] is particularly preferably 5-(3-chloro-2-fluorobenzyl)-2-fluoro-4-methoxybenzoic acid, 5-(3-chloro-2-fluorobenzyl)-2-fluoro-4-methoxybenzoic acid methyl ester or 5-(3-chloro-2-fluorobenzyl)-2-fluoro-4-methoxybenzoic acid ethyl ester.

Compound [II] is particularly preferably 3-chloro-2-fluorobenzyl chloride.

Compound (1) [compounds (1-A) and (1-B)], compound (2) [compounds (2-A) and (2-B)], compound (2-3) [compounds (2-3-A) and (2-3-B)], compound (4) [compounds (4-A) and (4-B)], compound (4-1) [compounds (4-1-A) and (4-1-B)], compound (4-2) [compounds (4-2-A) and (4-2-B)], compound (10), compound [I] and the like to be used or produced in the present invention may be pharmaceutically acceptable salts (sometimes to be simply referred to as salts in the present specification).

The "salt" may be any nontoxic salt as long as it can be formed from the compound to be used in the present invention and, for example, salts obtained by reaction with inorganic acids such as hydrochloric acid, sulfuric acid, phosphoric acid, hydrobromic acid and the like; organic acids such as oxalic acid, malonic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid and the like; inorganic bases such as sodium hydroxide, potassium hydroxide, calcium hydroxide, magnesium hydroxide, ammonium hydroxide and the like; organic bases such as methylamine, diethylamine, triethylamine, triethanolamine, ethylenediamine, tris(hydroxymethyl)methylamine, guanidine, choline, cinchonine and the like; amino acid such as lysin, arginine, alanine and the like, and the like can be mentioned. Preferably, salts obtained by reaction with inorganic acids such as hydrochloric acid, sulfuric acid, hydrobromic acid and the like; organic acids such as oxalic acid, malonic acid, citric acid, fumaric acid, acetic acid, trifluoroacetic acid, methanesulfonic acid, benzenesulfonic acid and the like; inorganic bases such as sodium hydroxide, potassium hydroxide, calcium hydroxide, magnesium hydroxide, ammonium hydroxide and the like; organic base such as methylamine, diethylamine, triethylamine, tris(hydroxymethyl)methylamine and the like, and the like can be mentioned. The compound used in the present invention also encompasses water-containing product, hydrate and solvate of each compound.

In addition, the compound used in the present invention may have various isomers. For example, when a double bond is present, E form and Z form are present as geometric isomers. Moreover, tautomer can also be present. Further, when an optical isomer may be present as an isomer, each optical isomer and a mixture thereof are also encompassed in the present invention. When desired, these isomers may be optically resolved or individually produced by a method known per se.

Accordingly, those of ordinary skill in the art should understand that all of these isomers and mixtures thereof are encompassed in the present invention. The compound of the present invention is preferably isolated and purified from various isomers, by-products, metabolites and prodrugs, and preferably has a purity of not less than 90%, more preferably not less than 95%.

One example of the production method of the present invention is explained in the following. However, the present invention is not limited thereto.

Even in the absence of description in the production methods, those of ordinary skill in the art will understand that an efficient production can be performed by employing, where necessary, introduction of a protecting group into a functional group, removal of the protecting group during workup, conversion to a desired functional group at any stage and the like.

The workup after reaction in each step can be applied by a typical method, wherein isolation and purification is performed by selecting or combining conventional methods as necessary, such as crystallization, recrystallization, distillation, partition, silica gel column chromatography, preparative HPLC and the like.

In the following production methods and the present specification, "room temperature" means generally 15° C.-30° C., unless particularly described.

Unless otherwise specified, the amount of the solvent to be used in the following production methods and the present specification is an amount that can be stirred in the reaction system.

In the compounds represented by the formulas (1), (2), (2-1), (2-2), (2-3), (3), (4-1), (4-2), (4), (5) and (6), when R is a methoxy group, they are compounds (1-A), (2-A), (2-1-A), (2-2-A), (2-3-A), (3-A), (4-1-A), (4-2-A), (4-A), (5-A) and (6-A), respectively, and when R is a fluorine atom, they are compounds (1-B), (2-B), (2-1-B), (2-2-B), (2-3-B), (3-B), (4-1-B), (4-2-B), (4-B), (5-B) and (6-B), respectively.

The production method of compound (10) or a salt thereof, which is an anti-HIV agent (compound), from compound (1) or a salt thereof, is shown in the following scheme. Specifically, the method using compound (1-A), which is compound (1) wherein R is a methoxy group is shown.

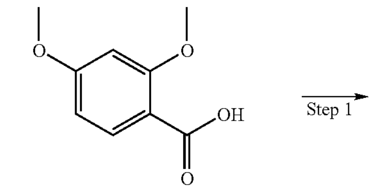
(1-A)
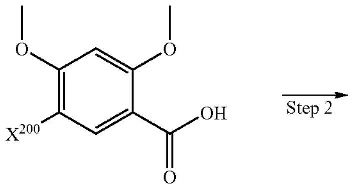
(2-A)
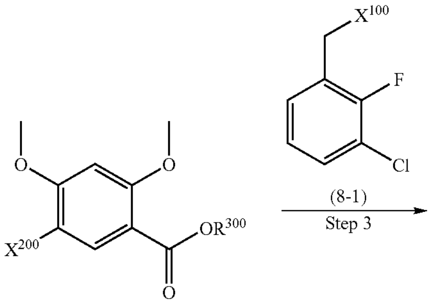
(2-1-A)
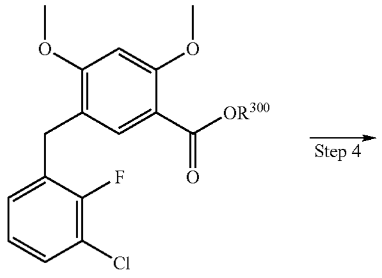
(2-2-A)
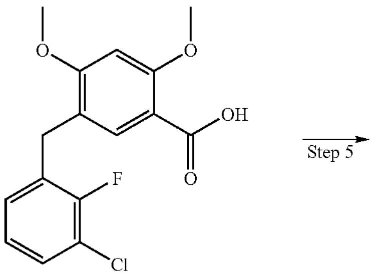
(2-3-A)
-continued
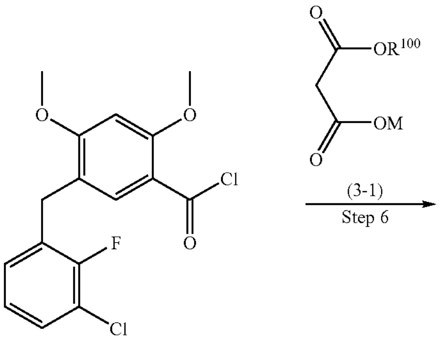
(3-A)
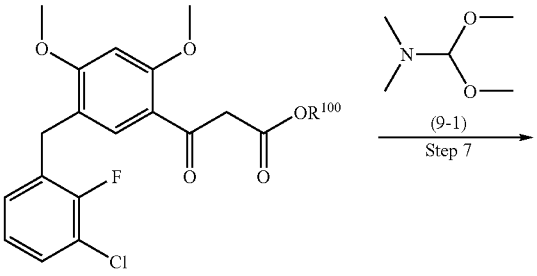
(4-A)
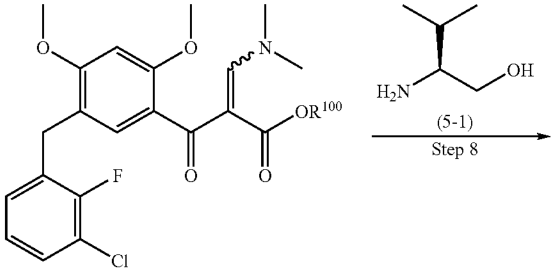
(5-A)
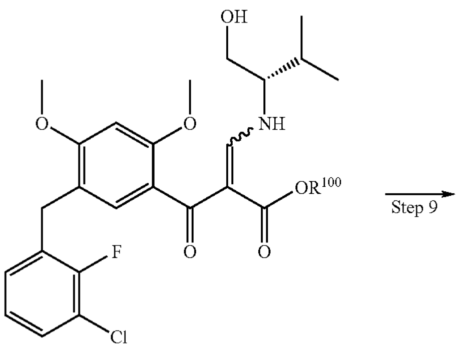
(6-A)

-continued

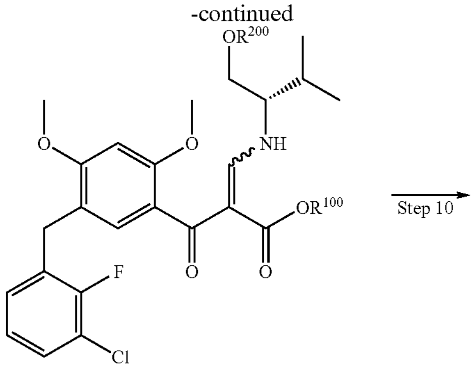

(7)

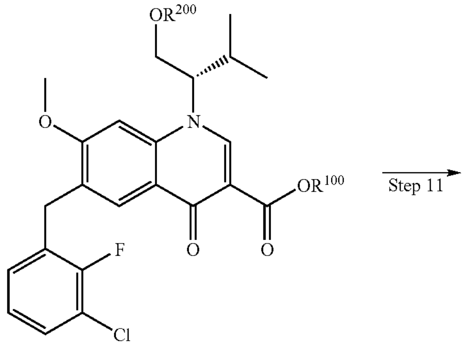

(9)

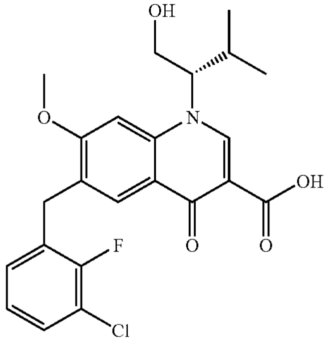

(10)

In the above-mentioned scheme, $R^{100}$ is a $C_1$-$C_4$ alkyl group, $R^{200}$ is a hydroxyl-protecting group, $R^{300}$ is a $C_1$-$C_4$ alkyl group, $X^{100}$ is a halogen atom, $X^{200}$ is a halogen atom, and M is a metal atom M.

Step 1

Compound (2-A) or a salt thereof can be produced by reacting compound (1-A) or a salt thereof with a halogenating agent in a solvent.

Compound (1-A) and a salt thereof may be commercially available product, or can be synthesized separately according to a known technique.

Examples of the halogenating agent include brominating agents such as bromine, N-bromosuccinimide and the like, and iodinating agents such as iodine, N-iodosuccinimide and the like. A brominating agent is preferable and bromine is more preferable.

The halogenating agent is generally 1.0 to 2.0 mol, preferably 1.0 to 1.2 mol, per 1 mol of compound (1-A).

In addition, a sulfite (e.g., sodium sulfite etc.) may be added after completion of the reaction, for the purpose of the treatment of the free halogen.

The amount of the sulfite to be used is generally 0 to 1.1 mol, preferably 0 to 0.3 mol, per 1 mol of compound (1-A).

Examples of the solvent include halogenated solvents such as dichloromethane, chloroform, carbon tetrachloride, 1,2-dichloroethane and the like; polar solvents such as N,N-dimethylformamide (DMF), N,N-dimethylacetamide (DMA), dimethyl sulfoxide, acetonitrile and the like; acidic solvents such as trifluoromethanesulfonic acid, sulfuric acid, acetic acid and the like or a mixed solvent thereof and the like. An acidic solvent is preferable and acetic acid is particularly preferable.

The reaction temperature is generally 0° C. to 50° C., preferably 15° C. to 30° C.

The reaction time is generally 1 hr to 48 hr, preferably 1 hr to 12 hr, more preferably 1 hr to 3 hr.

Step 2

Compound (2-1-A) can be obtained by subjecting a compound represented by the formula (2-A) or a salt thereof to a carboxyl-protecting reaction in a solvent under an acidic condition.

Compound (2-A) and a salt thereof may be commercially available product, or can be synthesized separately according to a known technique.

As one example of the carboxyl-protecting reaction, an esterification reaction is explained in the following. However, those of ordinary skill in the art will understand that the carboxyl-protecting reaction is not limited thereto.

Examples of the acid include trifluoromethanesulfonic acid, acetic acid, sulfuric acid, concentrated sulfuric acid and the like, with preference given to sulfuric acid.

The number of equivalence of the acid to be used is 0.1 to 1.0, preferably 0.2 to 0.8, per 1 equivalent of compound (2-A) or a salt thereof.

The reaction temperature is generally 0° C. to 100° C., preferably 30° C. to 80° C., particularly preferably 60° C. to 70° C. The reaction time is generally 1 hr to 48 hr, preferably 6 hr to 12 hr.

Examples of the solvent include alcohol solvents such as methanol, ethanol, n-propanol, isopropanol, n-butanol, branched butanol and the like, with preference given to methanol and ethanol.

Step 3

Compound (2-2-A) can be obtained by reacting compound (2-1-A) with a compound represented by the formula (8-1'):

(8-1')

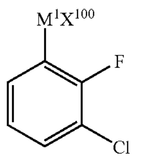

wherein $X^{100}$ is a halogen atom, $M^1$ is a metal atom (e.g., zinc atom etc. (hereinafter sometimes to be abbreviated as compound (8-1')) in a solvent, in the presence of a catalyst, as necessary in the presence of a ligand.

Compound (8-1') can be synthesized separately according to Reference Example 1, 2 or a known technique. Compound (2-1-A) can be obtained in the same manner as in the above-mentioned Step 2.

Specifically, a compound represented by the formula (8-1') can be obtained by reacting, in advance, the metal atom $M^1$ with a halide and an alkylsilyl compound in a solvent, and reacting the reaction mixture with the compound (8-1) solution.

Compound (8-1) may be commercially available product, or can be synthesized separately according to a known technique. It is preferably 3-chloro-2-fluorobenzyl chloride or 3-chloro-2-fluorobenzyl bromide.

The metal atom $M^1$ is generally 1 to 5 mol, preferably 1 to 1.5 mol, per 1 mol of compound (8-1).

Examples of the halide include 1,2-dibromoethane and the like, with preference given to 1,2-dibromoethane.

The amount of the halide to be used is 0.01 to 0.1 mol, preferably 0.01 to 0.02 mol, per 1 mol of compound (8-1).

Examples of the alkylsilyl compound include trimethylsilyl chloride and the like, with preference given to trimethylsilyl chloride.

The amount of the alkylsilyl compound to be used is 0.01 to 0.1 mol, preferably 0.01 to 0.02 mol, per 1 mol of compound (8-1).

Examples of the solvent include ether solvents such as 1,4-dioxane, diethyl ether, 1,2-dimethoxyethane, tetrahydrofuran (THF) and the like; hydrocarbon solvents such as toluene, hexane and the like, and the like. Preferable examples of the solvent include ether solvent, and it is particularly preferably THF.

The reaction temperature is generally 0° C. to 100° C., particularly preferably 20° C. to 65° C.

The reaction time is generally 1 hr to 24 hr, preferably 1 hr to 12 hr, particularly preferably 3 hr to 8 hr.

The reaction is preferably carried out under argon atmosphere or under nitrogen atmosphere, particularly preferably under argon atmosphere.

Compound (8-1') is particularly preferably 3-chloro-2-fluorobenzylzinc bromide, 3-chloro-2-fluorobenzylzinc chloride or a tetrahydrofuran solution thereof.

The amount of compound (8-1') to be used is generally 1 to 5 mol, preferably 1 to 2 mol, per 1 mol of compound (2-1-A).

Examples of the catalyst include palladium catalysts such as bis(dibenzylideneacetone)palladium, tris(dibenzylideneacetone)dipalladium, dichlorobis(triphenylphosphine)palladium, dichlorobis(benzonitrile)palladium, dichloroethylenediaminepalladium, palladium acetate, palladium chloride, tetrakis(triphenylphosphine)palladium, bis(triphenylphosphine)palladium(II) dichloride, palladium-carbon and the like, nickel catalyst and the like, with preference given to tris(dibenzylideneacetone)dipalladium.

Examples of the ligand include triphenylphosphine, tri(2-tolyl)phosphine, tri(2-furyl)phosphine and the like, with preference given to triphenylphosphine.

The amount of the ligand and catalyst to be used is generally 0.01 to 0.1 mol, preferably 0.02 to 0.07 mol, particularly preferably 0.02 to 0.06 mol, per 1 mol of compound (2-1-A), respectively.

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; polar solvents such as 1-methyl-2-pyrrolidinone, N,N-dimethylformamide (DMF), N,N-dimethylacetamide (DMA), dimethyl sulfoxide, acetonitrile and the like or a mixed solvent thereof and the like. An ether solvent, polar solvent or a mixed solvent thereof is preferable and tetrahydrofuran, 1-methyl-2-pyrrolidinone or a mixed solvent thereof is more preferable.

The reaction temperature is generally 0° C. to 100° C., preferably 40° C. to 80° C., more preferably 50° C. to 70° C.

The reaction time is generally 1 hr to 24 hr, preferably 1 hr to 10 hr, more preferably 2 hr to 6 hr.

The reaction is preferably carried out under argon atmosphere or under nitrogen atmosphere, particularly preferably under nitrogen atmosphere.

When the used catalyst is removed, the reaction mixture is preferably treated with a base such as ammonium chloride, sodium hydroxide, potassium hydroxide, lithium hydroxide, diethylenetriamine, ethylenediamine and the like, particularly preferably an aqueous ammonium chloride solution or an aqueous ethylenediamine solution.

Step 4

Compound (2-3-A) or a salt thereof can be obtained by subjecting compound (2-2-A) to hydrolysis in a solvent under a basic condition (e.g., in the presence of a base such as sodium hydroxide, potassium hydroxide, lithium hydroxide and the like) or under an acidic condition (e.g., in the presence of an acid such as hydrochloric acid, sulfuric acid and the like).

Compound (2-2-A) can be obtained in the same manner as in the above-mentioned Step 2.

The amount of the base to be used is generally 1 to 10 mol, preferably 1 to 5 mol, particularly preferably 1 to 2 mol, per 1 mol of compound (2-2-A).

The amount of the acid to be used is not particularly limited.

The reaction conditions is preferably a basic condition, and the reaction is carried out more preferably in the presence of sodium hydroxide, particularly preferably using an aqueous sodium hydroxide solution.

Examples of the solvent include hydrocarbon solvents such as toluene, xylene, hexane, heptane and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile, water and the like or a mixed solvent thereof and the like, with preference given to a mixed solvent of isopropanol and water.

The reaction temperature is generally 0° C. to 100° C., preferably 15° C. to 100° C., more preferably 50° C. to 70° C.

The reaction time is generally 1 hr to 24 hr, preferably 1 hr to 12 hr, more preferably 1 hr to 8 hr.

For the workup, a treatment with an activated carbon can be carried out for the purpose of purification of compound (2-3-A). For example, when the reaction condition is a basic condition, the treatment can be carried out without any limitation on the amount of the activated carbon to be used.

Step 5

Compound (3-A) can be obtained by reacting compound (2-3-A) or a salt thereof with a chlorinating agent in a solvent according to a conventional method.

Compound (2-3-A) and a salt thereof can be obtained in the same manner as in the above-mentioned Step 4.

Examples of the chlorinating agent include oxalyl chloride, phosphorus oxychloride, thionyl chloride and the like, with preference given to thionyl chloride. When oxalyl chloride or thionyl chloride is used as a chlorinating agent, a catalyst (e.g., N,N-dimethylformamide etc.) may be added.

The amount of the chlorinating agent to be used is generally 1.0 to 1.5 mol, preferably 1.0 to 1.2 mol, per 1 mol of compound (2-3-A) or a salt thereof.

Examples of the solvent include hydrocarbon solvents such as toluene, xylene, hexane, heptane and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; polar solvents such as N,N-dimethylformamide (DMF), N,N-dimethylacetamide (DMA), dimethyl sulfoxide, acetonitrile and the like or a mixed solvent thereof and the like. A hydrocarbon solvent is preferable and toluene is more preferable.

The reaction temperature is generally 0° C. to 100° C., preferably 60° C. to 80° C., more preferably 70° C. to 80° C.

The reaction time is generally 1 hr to 24 hr, preferably 1 hr to 10 hr, more preferably 1 hr to 5 hr.

The reaction is preferably carried out under argon atmosphere or under nitrogen atmosphere, particularly preferably under nitrogen atmosphere.

Step 6

Compound (4-A) or a salt thereof, which is a β-ketoester, can be produced by reacting a malonic acid monoester represented by the formula (3-1) or a salt thereof (hereinafter sometimes to be abbreviated as compound (3-1)) with compound (3-A) in a solvent, in the presence of a base and a chelator, and treating the resulting compound with an acid.

Compound (3-A) can be obtained in the same manner as in the above-mentioned Step 5.

In compound (3-1), M is a metal atom M.

Compound (3-1) may be commercially available product, or can be synthesized separately according to a known technique. It is particularly preferably potassium ethyl malonate.

The amount of compound (3-1) to be used is generally 1 to 10 mol, preferably 1.0 to 2.0 mol, per 1 mol of compound (3-A).

Examples of the base include organic bases such as triethylamine, N-methylmorpholine and the like, with preference given to triethylamine.

The amount of the base to be used is generally 1 to 10 mol, preferably 2.0 to 3.0 mol, per 1 mol of compound (3-A).

Examples of the chelator include a divalent magnesium compound (e.g., magnesium chloride) and the like, with preference given to magnesium chloride.

The amount of the chelator to be used is generally 1 to 10 mol, preferably 2.0 to 3.0 mol, per 1 mol of compound (3-A).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; polar solvents such as N,N-dimethylformamide (DMF), N,N-dimethylacetamide (DMA), dimethyl sulfoxide, acetonitrile and the like or a mixed solvent thereof and the like. An ether solvent, an ester solvent or a mixed solvent thereof is preferable and tetrahydrofuran, ethyl acetate or a mixed solvent thereof is more preferable.

The reaction temperature is generally 0° C. to 100° C., preferably 60° C. to 80° C., more preferably 70° C. to 80° C.

The reaction time is generally 1 hr to 24 hr, preferably 2 hr to 10 hr, more preferably 2 hr to 5 hr.

Examples of the acid include acetic acid, hydrochloric acid, sulfuric acid and the like, with preference given to hydrochloric acid.

The amount of the acid to be used is not particularly limited.

The reaction temperature after the addition of the acid is generally 0° C. to 100° C., preferably 0° C. to 50° C., more preferably 15° C. to 30° C. The reaction time is generally 0.5 hr to 10 hr, preferably 0.5 hr to 5 hr, more preferably 0.5 hr to 2 hr.

The reaction is preferably carried out under argon atmosphere or under nitrogen atmosphere, particularly preferably under nitrogen atmosphere.

The production process compound (4-A) or a salt thereof from compound (3-A) is shown in the following scheme.

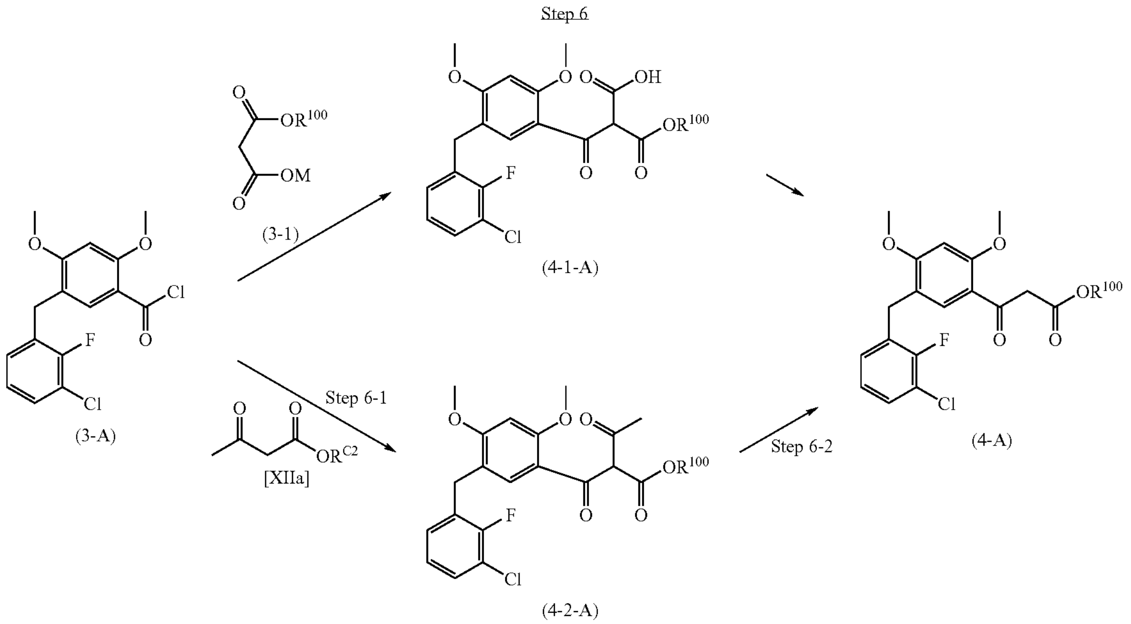

wherein $R^{100}$ is a $C_1$-$C_4$ alkyl group, $R^{C2}$ is a carboxyl-protecting group.

Step 6 is, in detail, a step of producing compound (4-A) or a salt thereof via compound (4-1-A) or a salt thereof, by reacting compound (3-A) with compound (3-1), and treating the resulting compound with an acid.

Compound (4-2-A) or a salt thereof can be obtained by reacting compound (3-A) with a β-ketoester compound represented by the formula [XIIa]:

[XIIa]

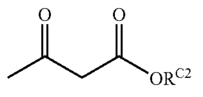

wherein $R^{C2}$ is a carboxyl-protecting group, in a solvent in the presence of a base (Step 6-1).

Examples of the base used in Step 6-1 include magnesium compounds (e.g., magnesium chloride etc.), barium oxide and the like, with preference given to barium oxide. The amount of the base to be used is generally 1 to 10 mol, preferably 1 to 2 mol, per 1 mol of compound (3-A).

Examples of the solvent used in Step 6-1 include alcohol solvents such as methanol, ethanol, n-propanol, isopropanol and the like; hydrocarbon solvents such as toluene, hexane, xylene and the like; halogenated solvents such as dichloromethane, carbon tetrachloride, 1,2-dichloroethane and the like; ether solvents such as 1,4-dioxane, diethyl ether, 1,2-dimethoxyethane, THF and the like; polar solvents such as N,N-dimethylformamide (DMF), dimethyl sulfoxide, acetonitrile and the like; water or a mixed solvent thereof and the like. A mixed solvent of toluene and water, or ethanol is preferable and a mixed solvent of toluene and water is more preferable.

Compound [XIIa] may be commercially available product, or can be synthesized separately according to a known technique. It is particularly preferably ethyl acetoacetate.

The amount of compound [XIIa] to be used is generally 1 to 10 mol, preferably 1 to 2 mol, per 1 mol of compound (3-A).

The reaction temperature of Step 6-1 is generally 0° C. to 100° C., preferably 0° C. to 50° C., particularly preferably 0° C. to 30° C.

Furthermore, compound (4-A) or a salt thereof can be obtained by subjecting compound (4-2-A) or a salt thereof to a deacetylation reaction in a solvent under a basic condition (e.g., in the presence of a base such as sodium acetate, potassium acetate, sodium carbonate, lithium hydroxide and the like) or under an acidic condition (e.g., in the presence of an acid such as hydrochloric acid, sulfuric acid or acetic acid and the like) (Step 6-2).

The amount of the base used in Step 6-2 is generally 1 to 10 mol, preferably 2 to 4 mol, particularly preferably 3 mol, per 1 mol of compound (4-2-A).

The amount of the acid used in Step 6-2 is not particularly limited.

The reaction conditions of Step 6-2 is preferably a basic condition, particularly preferably in the presence of sodium acetate.

Examples of the solvent used in Step 6-2 include alcohol solvents such as methanol, ethanol, n-propanol, isopropanol and the like; hydrocarbon solvents such as toluene, hexane, xylene and the like; halogenated solvents such as dichloromethane, chloroform, carbon tetrachloride, 1,2-dichloromethane and the like; ether solvents such as 1,4-dioxane, diethyl ether, 1,2-dimethoxyethane, tetrahydrofuran and the like; polar solvents such as acetonitrile and the like; water or a mixed solvent thereof and the like, with preference given to a mixed solvent of ethanol and water.

The reaction temperature of Step 6-2 is generally 0° C. to 100° C., preferably 0° C. to 50° C., particularly preferably 0° C. to 30° C.

The reaction time of Step 6-2 is generally 20 hr to 120 hr, preferably 24 hr to 100 hr.

Step 6-2 can be continuously performed after the above-mentioned Step 6-1 without isolation treatment of compound (4-2-A) or a salt thereof obtained in the above-mentioned Step 6-1.

In the case, the reaction condition is preferably a basic condition, and the reaction is preferably carried out in the presence of sodium acetate.

The amount of the base to be used is generally 1 to 10 mol, preferably 2 to 4 mol, particularly preferably 3 mol, per 1 mol of compound (3-A).

The reaction temperature is generally 0° C. to 100° C., preferably 0° C. to 50° C., particularly preferably 0° C. to 30° C.

The reaction time is generally 20 hr to 120 hr, preferably 24 hr to 100 hr.

Step 7

Compound (5-A) can be obtained by reacting compound (4-A) or a salt thereof with compound (9-1): N,N-dimethylformamide dimethyl acetal in a solvent.

Compound (4-A) and a salt thereof can be obtained in the same manner as in the above-mentioned Step 6.

Compound (9-1) may be commercially available product, or can be synthesized separately according to a known technique.

The amount of compound (9-1) to be used is generally 1 to 10 mol, preferably 1.0 to 2 mol, particularly preferably 1.0 to 1.5 mol, per 1 mol of compound (4-A) or a salt thereof.

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; polar solvents such as N,N-dimethylformamide (DMF), N,N-dimethylacetamide (DMA), dimethyl sulfoxide, acetonitrile and the like or a mixed solvent thereof and the like, with preference given to toluene.

The reaction temperature is generally 20° C. to 110° C., preferably 70° C. to 110° C., more preferably 90° C. to 100° C.

The reaction time is generally 1 hr to 48 hr, preferably 10 hr to 24 hr, more preferably 15 hr to 24 hr.

The reaction is preferably carried out under argon atmosphere or under nitrogen atmosphere, particularly preferably under nitrogen atmosphere.

Step 8

Compound (6-A) can be obtained by reacting compound (5-A) with compound (5-1): L-valinol((S)-2-amino-3-methylbutan-1-ol) in a solvent.

Step 8-1

Compound (5-A) can be obtained in the same manner as in the above-mentioned Step 7.

Compound (5-1) may be commercially available product, or can be synthesized separately according to a known technique.

The optical purity of compound (5-1) is not less than 95% ee, preferably not less than 97% ee, more preferably not less than 99% ee.

The amount of compound (5-1) to be used is generally 1 to 10 mol, preferably 1 to 2 mol, particularly preferably 1.1 to 1.3 mol, per 1 mol of compound (5-A).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile and the like or a mixed solvent thereof and the like, with preference given to toluene.

The reaction temperature is generally 0° C. to 100° C., preferably 0° C. to 50° C., more preferably 0° C. to 30° C.

The reaction time is generally 0.5 hr to 24 hr, preferably 0.5 hr to 12 hr, more preferably 0.5 hr to 3 hr.

The reaction is preferably carried out under argon atmosphere or under nitrogen atmosphere, particularly preferably under nitrogen atmosphere.

Step 8-2

Compound (7) can be obtained directly by reacting compound (5-A) with compound (5-1) wherein the hydroxyl group is protected by the "hydroxyl-protecting group" mentioned above in a solvent.

Compound (5-1) protected by the hydroxyl-protecting group can be synthesized separately according to a known technique. Examples of the compound (5-1) protected by the hydroxyl-protecting group include (S)-1-(tert-butyldimethylsilanyloxymethyl)-2-methylpropylamine, (S)-2-methyl-1-(trimethylsilanyloxymethyl)propylamine, (S)-2-methyl-1-(tetrahydropyran-2-yloxymethyl)propylamine, methyl 2-amino-3-methylbutylcarbonate and ethyl 2-amino-3-methylbutylcarbonate. It is preferably (S)-1-(tert-butyldimethylsilanyloxymethyl)-2-methylpropylamine, (S)-2-methyl-1-(tetrahydropyran-2-yloxymethyl)propylamine or methyl 2-amino-3-methylbutylcarbonate, particularly preferably (S)-1-(tert-butyldimethylsilanyloxymethyl)-2-methylpropylamine.

The optical purity of compound (5-1) protected by the hydroxyl-protecting group is not less than 95% ee, preferably not less than 97% ee, more preferably not less than 99% ee.

The amount of compound (5-1) protected by the hydroxyl-protecting group to be used is generally 1 to 10 mol, preferably 1 to 2 mol, particularly preferably 1.1 to 1.3 mol, per 1 mol of compound (5-A).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile and the like or a mixed solvent thereof and the like, with preference given to toluene.

The reaction temperature is generally 0° C. to 100° C., preferably 0° C. to 50° C., more preferably 0° C. to 30° C.

The reaction time is generally 0.5 hr to 24 hr, preferably 0.5 hr to 12 hr, more preferably 0.5 hr to 3 hr.

The reaction is preferably carried out under argon atmosphere or under nitrogen atmosphere, particularly preferably under nitrogen atmosphere.

Step 9

Compound (7) can be obtained by introducing a protecting group to the hydroxyl group of compound (6-A) in a solvent according to a conventional method.

Compound (6-A) can be obtained in the same manner as in the above-mentioned Step 8-1.

For example, when the hydroxyl-protecting group is a tert-butyldimethylsilyl group, compound (7) can be obtained by adding a base and tert-butyldimethylsilyl chloride to compound (6-A) in a solvent.

The amount of the tert-butyldimethylsilyl chloride to be used is generally 1 to 10 mol, preferably 1 to 2 mol, particularly preferably 1 to 1.3 mol, per 1 mol of compound (6-A).

Examples of the base include triethylamine, diisopropylethylamine, pyridine, imidazole and the like. It is preferably imidazole.

The amount of the base to be used is generally 1 to 10 mol, preferably 1 to 2 mol, particularly preferably 1 to 1.3 mol, per 1 mol of compound (6-A).

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; polar solvents such as N,N-dimethylformamide (DMF), N,N-dimethylacetamide (DMA), dimethyl sulfoxide, acetonitrile, water and the like or a mixed solvent thereof and the like. An ether solvent, a hydrocarbon solvent, a mixed solvent thereof or the like is preferable and tetrahydrofuran, toluene, a mixed solvent thereof or the like is more preferable.

The reaction temperature is generally 0° C. to 100° C., preferably 15° C. to 70° C., more preferably 40° C. to 50° C.

The reaction time is generally 1 hr to 24 hr, preferably 1 hr to 10 hr, more preferably 1 hr to 5 hr.

The reaction is preferably carried out under argon atmosphere or under nitrogen atmosphere, particularly preferably under nitrogen atmosphere.

Step 10

Compound (9) can be obtained by subjecting compound (7) to a cyclization reaction in a solvent. A base and an additive can be added to the reaction system.

Compound (7) can be obtained in the same manner as in the above-mentioned Step 9 or the above-mentioned Step 8-2.

Examples of the base include sodium carbonate, potassium carbonate, sodium hydroxide, potassium hydroxide, potassium tert-butoxide, sodium hydride, potassium hydride, 1,8-diazabicyclo[5.4.0]-7-undecene and the like, with preference given to potassium carbonate.

The amount of the base to be used is generally 0.5 to 10 mol, preferably 0.5 to 2 mol, particularly preferably 0.5 to 1 mol, per 1 mol of compound (7).

Examples of the additive include quaternary ammonium salts such as tetra-n-butylammonium bromide and the like, quaternary phosphonium salts such as tetra-n-butylphosphonium bromide and the like, crown ethers such as 18-crown-6 and the like, and the like. A quaternary ammonium salt, a quaternary phosphonium salt or a crown ether is preferable and tetra-n-butylphosphonium bromide is more preferable.

The amount of the additive to be used is generally 0.05 to 10 mol, preferably 0.05 to 2 mol, particularly preferably 0.05 to 1.0 mol, per 1 mol of compound (7).

The additive may be added during the progress of the reaction.

Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile, water and the like or a mixed solvent thereof and the like, with preference given to toluene.

The reaction temperature is generally 20° C. to 140° C., preferably 80° C. to 120° C., more preferably 100° C. to 120° C.

The reaction time is generally 1 hr to 48 hr, preferably 4 hr to 36 hr, more preferably 8 hr to 24 hr.

The reaction is preferably carried out under argon atmosphere or under nitrogen atmosphere, particularly preferably under nitrogen atmosphere.

Step 11

Compound (10) or a salt thereof can be obtained by subjecting compound (9) to hydrolysis in a solvent under a basic condition (e.g., in the presence of a base such as sodium hydroxide, potassium hydroxide, lithium hydroxide and the like) or under an acidic condition (e.g., in the presence of an acid such as hydrochloric acid, sulfuric acid and the like).

The amount of the base to be used is generally 1 to 10 mol, preferably 1 to 5 mol, particularly preferably 1 to 2 mol, per 1 mol of compound (9).

The amount of the acid to be used is not particularly limited.

The reaction condition is preferably a basic condition, and the reaction is more preferably carried out in the presence of sodium hydroxide, particularly preferably using an aqueous sodium hydroxide solution.

Examples of the solvent include hydrocarbon solvents such as toluene, xylene, hexane, heptane and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile, water and the like or a mixed solvent thereof and the like, with preference given to a mixed solvent of isopropanol and water.

The reaction temperature is generally 0° C. to 150° C., preferably 15° C. to 100° C., more preferably 65° C. to 75° C.

The reaction time is generally 1 hr to 24 hr, preferably 1 hr to 12 hr, more preferably 1 hr to 8 hr.

For the workup, a treatment with an activated carbon or extraction operation can be carried out for the purpose of the purification of compound (10). For example, when the reaction condition is a basic condition, the activated carbon treatment can be carried out without any limitation on the amount of the activated carbon to be used. Moreover, when hydrochloric acid or the like is used in the extraction operation, the amount thereof to be used is generally 1 to 10 mol, preferably 1 to 5 mol, particularly preferably 1 to 2 mol, per 1 mol of compound (9).

Examples of the solvent used in the extraction operation include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ketone solvents such as acetone, methylethylketone, methylisobutylketone, methylisopropylketone and the like; ether solvents such as 1,4-dioxane, diethyl ether, 1,2-dimethoxyethane, tetrahydrofuran, anisole and the like; polar solvents such as acetonitrile and the like or a mixed solvent thereof and the like, with preference given to toluene, heptane, methyl acetate, ethyl acetate, propyl acetate, isopropyl acetate, butyl acetate, isobutyl acetate, acetone, methylethylketone, methylisobutylketone, methylisopropylketone and anisole.

Compound (10) or a salt thereof, which is an anti-HIV agent (compound), can be also produced using compound (1-B), which is compound (1) wherein R is a fluorine atom.

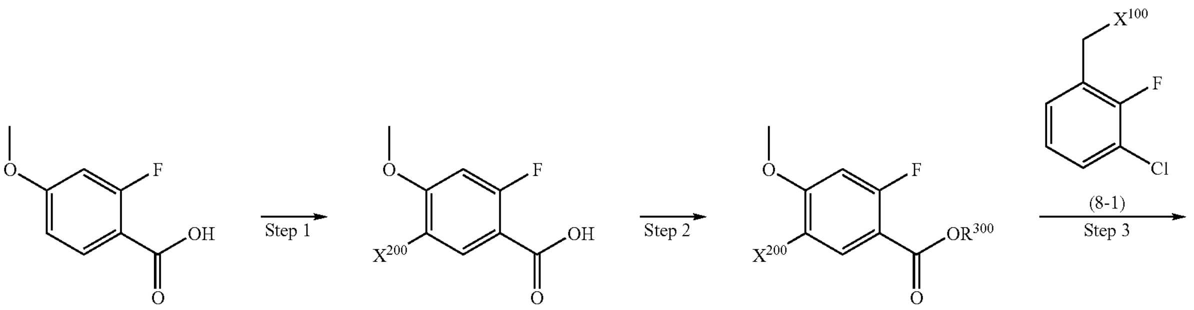

(1-B) (2-B) (2-1-B)

-continued
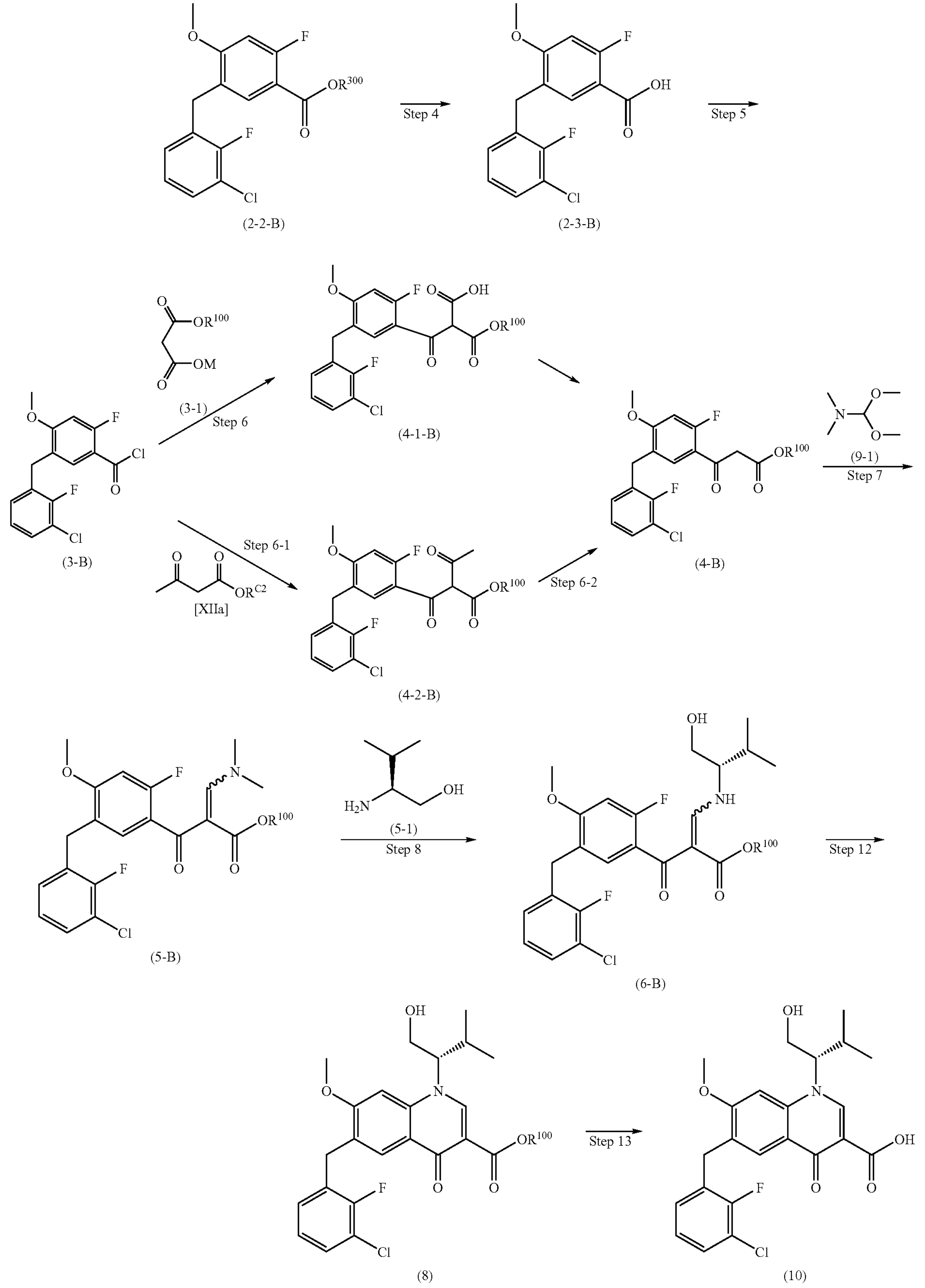

In the above-mentioned scheme, $R^{100}$ is a $C_1$-$C_4$ alkyl group, $R^{300}$ is a $C_1$-$C_4$ alkyl group, $X^{100}$ is a halogen atom, $X^{200}$ is a halogen atom, M is a metal atom M, $R^{C2}$ is a carboxyl-protecting group.

Compound (2-B) or a salt thereof can be obtained by reacting compound (1-B) or a salt thereof with a halogenating agent, in the same manner as in the above-mentioned Step 1. Compound (1-B) and a salt thereof may be commercially available product, or can be synthesized separately according to a known technique.

Compound (2-1-B) can be obtained by subjecting compound (2-B) or a salt thereof to a carboxyl-protecting reaction, in the same manner as in the above-mentioned Step 2.

Compound (2-2-B) can be obtained by reacting compound (2-1-B) with compound (8-1'), in the same manner as in the above-mentioned Step 3.

Compound (2-3-B) or a salt thereof can be obtained by subjecting compound (2-2-B) to hydrolysis, in the same manner as in the above-mentioned Step 4.

Compound (3-B) can be obtained by reacting compound (2-3-B) or a salt thereof with a chlorinating agent, in the same manner as in the above-mentioned Step 5.

Compound (4-B) or a salt thereof can be obtained via compound (4-1-B) or a salt thereof, by reacting compound (3-B) with compound (3-1), in the same manner as in the above-mentioned Step 6, and treating the resulting compound with an acid.

Alternatively, compound (4-B) or a salt thereof can be obtained by reacting compound (3-B) with the formula [XIIa] in a solvent, in the same manners as in the above-mentioned Step 6-1 and Step 6-2, and subjecting the obtained compound (4-2-B) to a deacetylation reaction.

Compound (5-B) can be obtained by reacting compound (4-B) or a salt thereof with compound (9-1), in the same manner as in the above-mentioned Step 7.

Compound (6-B) can be obtained by reacting compound (5-B) with compound (5-1), in the same manner as in the above-mentioned Step 8-1.

Step 12

Compound (8) can be obtained by subjecting compound (6-B) to a cyclization reaction in a solvent (Step 12).

A base can be added to the reaction system, as necessary.

Examples of the base include sodium carbonate, potassium carbonate, sodium hydroxide, potassium hydroxide, potassium tert-butoxide, sodium hydride, potassium hydride, 1,8-diazabicyclo[5.4.0]-7-undecene and the like, with preference given to potassium carbonate.

The amount of the base to be used is generally 1 to 10 mol, preferably 1 to 5 mol, particularly preferably 1 to 2 mol, per 1 mol of compound (6-B).

Examples of the solvent include hydrocarbon solvents such as toluene, hexane, xylene and the like; halogenated solvents such as dichloromethane, chloroform, carbon tetrachloride, 1,2-dichloromethane and the like; ether solvents such as 1,4-dioxane, diethyl ether, 1,2-dimethoxyethane, tetrahydrofuran and the like; polar solvents such as N,N-dimethylformamide (DMF), dimethyl sulfoxide, acetonitrile and the like; ethyl acetate or a mixed solvent thereof and the like, with preference given to N,N-dimethylformamide.

The reaction temperature is generally room temperature to 150° C., preferably 50° C. to 100° C. or 60° C. to 110° C.

The reaction time is generally 1 hr to 24 hr, preferably 5 hr to 12 hr, particularly preferably 8 hr to 10 hr.

Step 13

Compound (10) or a salt thereof can be obtained by subjecting compound (8) to hydrolysis in a solvent under a basic condition (e.g., in the presence of a base such as sodium hydroxide, potassium hydroxide, lithium hydroxide and the like) or under an acidic condition (e.g., in the presence of an acid such as hydrochloric acid, sulfuric acid and the like).

The amount of the base to be used is generally 1 to 10 mol, preferably 1 to 5 mol, particularly preferably 1 to 2 mol, per 1 mol of compound (8).

The amount of the acid to be used is not particularly limited.

The reaction condition is preferably a basic condition, and the reaction is particularly preferably carried out in the presence of sodium hydroxide.

Examples of the solvent include alcohol solvents such as methanol, ethanol, n-propanol, isopropanol and the like; hydrocarbon solvents such as toluene, hexane, xylene and the like; halogenated solvents such as dichloromethane, chloroform, carbon tetrachloride, 1,2-dichloromethane and the like; ether solvents such as 1,4-dioxane, diethyl ether, 1,2-dimethoxyethane, tetrahydrofuran and the like; polar solvents such as N,N-dimethylformamide (DMF), dimethyl sulfoxide, acetonitrile and the like; water or a mixed solvent thereof and the like, with preference given to a mixed solvent of ethanol and water.

The reaction temperature is preferably 0° C. to 100° C., more preferably 40° C. to 60° C.

The reaction time is preferably 0.5 hr to 12 hr, preferably 0.5 hr to 3 hr.

In the workup, the pH of the reaction mixture is preferably 3-5.

The obtained compound (10) can be purified by recrystallization. Examples of the solvent include hydrocarbon solvents such as toluene, xylene, hexane, heptane and the like; ester solvents such as methyl acetate, ethyl acetate, propyl acetate, isopropyl acetate, butyl acetate, isobutyl acetate and the like; halogenated solvents such as dichloromethane, chloroform, carbon tetrachloride, 1,2-dichloroethane and the like; ketone solvents such as acetone, methylethylketone, methylisobutylketone and the like; ether solvents such as 1,4-dioxane, diethyl ether, 1,2-dimethoxyethane, tetrahydrofuran, anisole and the like; alcohol solvents such as methanol, ethanol, n-propanol, isopropanol and the like; polar solvents such as N,N-dimethylformamide (DMF), N,N-dimethylacetamide (DMA), dimethyl sulfoxide, acetonitrile, water and the like or a mixed solvent thereof and the like, with preference given to a mixed solvent of ethanol and water, and toluene.

The production method of compound [I] and the production method of compound [III] from compound [I] are shown below.

Production Method-1

The production method of compound [I] or a salt thereof characterized by reacting compound [II] with compound [IV] in the presence of a metal atom $M^1$ is shown in the following scheme.

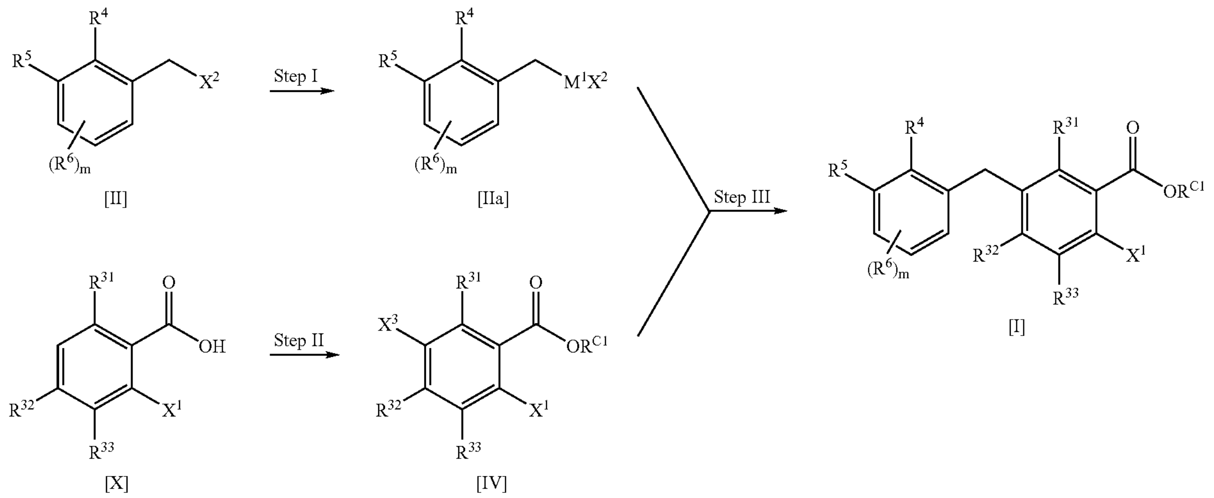

wherein $M^1$ is a metal atom such as zinc and the like, and each symbol is as defined above.

Step I

A compound represented by the formula [IIa] (hereinafter sometimes to be abbreviated as compound [IIa]) can be obtained by reacting, in advance, a metal atom with a halide and an alkylsilyl compound in a solvent, and reacting the reaction mixture with the compound [II] solution.

Compound [II] may be commercially available product, or can be synthesized separately according to a known technique. It is particularly preferably 3-chloro-2-fluorobenzyl chloride.

The amount of the metal atom $M^1$ to be used is generally 1 to 5 mol, preferably 1 to 1.5 mol, per 1 mol of compound [II].

Examples of the halide include 1,2-dibromoethane and the like, with preference given to 1,2-dibromoethane.

The amount of the halide to be used is 0.01 to 0.1 mol, preferably 0.01 to 0.02 mol, per 1 mol of compound [II].

Examples of the alkylsilyl compound include trimethylsilyl chloride and the like, with preference given to trimethylsilyl chloride.

The amount of the alkylsilyl compound to be used is 0.01 to 0.1 mol, preferably 0.01 to 0.02 mol, per 1 mol of compound [II].

Examples of the solvent include ether solvents such as 1,4-dioxane, diethyl ether, 1,2-dimethoxyethane, tetrahydrofuran (THF) and the like; hydrocarbon solvents such as toluene, hexane and the like, and the like. Preferable examples of the solvent include ether solvents, particularly preferably THF.

The amount of the solvent to be used is generally 1 to 20 ml, preferably 2 to 5 ml, per 1 g of the halide.

The reaction temperature is generally 0° C. to 100° C., particularly preferably 20° C. to 65° C.

The reaction time is generally 1 hr to 24 hr, preferably 1 hr to 12 hr, particularly preferably 3 hr to 8 hr.

The reaction is preferably carried out under argon atmosphere or under nitrogen atmosphere, particularly preferably under nitrogen atmosphere.

Step II

Compound [IV] can be obtained by subjecting a compound represented by the formula [X](hereinafter sometimes to be abbreviated as compound [X]) to a carboxyl-protecting reaction (e.g., esterification reaction) in an alcohol solvent under an acidic condition, and reacting the resulting compound with a halogenating agent.

The carboxyl-protecting reaction can be carried out according to a method known by those of ordinary skill in the art.

As one example of the carboxyl-protecting reaction, an esterification reaction is explained in the following. However, those of ordinary skill in the art will understand that the carboxyl-protecting reaction is not limited thereto.

(Esterification Reaction)

Compound [X] may be commercially available product, or can be synthesized separately according to a known technique.

Examples of the acid include trifluoromethanesulfonic acid, acetic acid, sulfuric acid, concentrated sulfuric acid and the like, with preference given to sulfuric acid.

The number of equivalence of the acid to be used is 0.1 to 1.0, preferably 0.2 to 0.3, relative to compound [X].

The reaction temperature is generally 0° C. to 100° C., preferably 30° C. to 80° C., particularly preferably 60° C. to 70° C.

The reaction time is generally 1 hr to 48 hr, preferably 6 hr to 12 hr.

(Halogenation)

Examples of the halogenating agent include bromine, iodine, N-bromosuccinimide, N-iodosuccinimide and the like, with preference given to bromine.

The amount of the halogenating agent to be used is generally 1 to 5 mol, preferably 1 to 3 mol, per 1 mol of compound [X].

In addition, a sulfite (e.g., sodium sulfite etc.) can be added as necessary, for the purpose of the treatment of the free halogen.

The amount of the sulfite to be used is generally 1 to 5 mol, preferably 1 to 2 mol, per 1 mol of compound [X].

Examples of the solvent include alcohol solvents such as methanol, ethanol, n-propanol, isopropanol and the like; hydrocarbon solvents such as toluene, hexane, xylene and the like; halogenated solvents such as dichloromethane, carbon tetrachloride, 1,2-dichloroethane and the like; ether solvents such as 1,4-dioxane, diethyl ether, 1,2-dimethoxyethane, THF and the like; polar solvents such as N,N-dimethylformamide (DMF), dimethyl sulfoxide, acetonitrile and the like, and the like. An alcohol solvent is preferable and methanol is particularly preferable.

The amount of the solvent to be used is generally 1 to 20 ml, preferably 10 to 12 ml, per 1 g of compound [X].

The reaction temperature is generally 0° C. to 100° C., preferably 20° C. to 50° C.

The reaction time is generally 1 hr to 48 hr, preferably 1 hr to 12 hr, particularly preferably 1 to 5 hr.

Step III

Compound [I] or a salt thereof can be obtained by reacting compound [IIa] with compound [IV] in a solvent in the presence of a catalyst, as necessary, in the presence of a ligand.

The amount of compound [IIa] to be used is generally 1 to 5 mol, preferably 1 to 2 mol, per 1 mol of compound [IV].

Examples of the catalyst include palladium catalyst such as bis(dibenzylideneacetone)palladium, tris(dibenzylideneacetone)dipalladium, dichlorobis(triphenylphosphine)palladium, dichlorobis(benzonitrile)palladium, dichloroethylenediaminepalladium, palladium acetate, palladium chloride, tetrakis(triphenylphosphine)palladium, bis(triphenylphosphine)palladium(II)dichloride, palladium-carbon and the like, nickel catalyst and the like, with preference given to tris(dibenzylideneacetone)dipalladium.

Examples of the ligand include triphenylphosphine, tri(2-tolyl)phosphine, tri(2-furyl)phosphine and the like, with preference given to triphenylphosphine.

The amount of the ligand and catalyst to be used is generally 0.01 to 0.1 mol, preferably 0.02 to 0.07 mol, particularly preferably 0.02 to 0.06 mol, per 1 mol of compound [IV], respectively.

Examples of the solvent include ether solvents such as 1,4-dioxane, 1,3-dioxolane, diethyl ether, 1,2-dimethoxyethane, THF and the like; hydrocarbon solvents such as toluene, hexane, xylene and the like; polar solvents such as 1-methyl-2-pyrrolidinone, N,N-dimethylformamide (DMF), dimethyl sulfoxide, acetonitrile and the like, and the like, with preference given to 1-methyl-2-pyrrolidinone.

The amount of the solvent to be used is generally 1 to 20 ml, preferably 10 to 15 ml, per 1 g of compound [IV].

The reaction temperature is generally room temperature to 100° C., preferably 70° C. to 90° C.

The reaction time is 1 hr to 24 hr, preferably 1 hr to 6 hr.

The reaction is preferably carried out under argon atmosphere or under nitrogen atmosphere, particularly preferably under nitrogen atmosphere.

When the used catalyst is removed, the reaction mixture is preferably treated with a base such as ammonium chloride, sodium hydroxide, potassium hydroxide, lithium hydroxide, diethylenetriamine, ethylenediamine and the like, particularly preferably an aqueous ammonium chloride solution or an aqueous ethylenediamine solution.

The amount of the base to be used is not particularly limited as long as the used catalyst can be removed.

Production Method-2

The production method of compound [III] or a salt thereof from compound [I] or a salt thereof via β-ketoester compound [V] is shown in the following scheme. Compound [I'], which is compound [I] wherein $R^{C1}$ is a carboxyl-protecting group, is used as a starting material. When $R^{C1}$ is a hydrogen atom, compound [Ia] is used as a starting material.

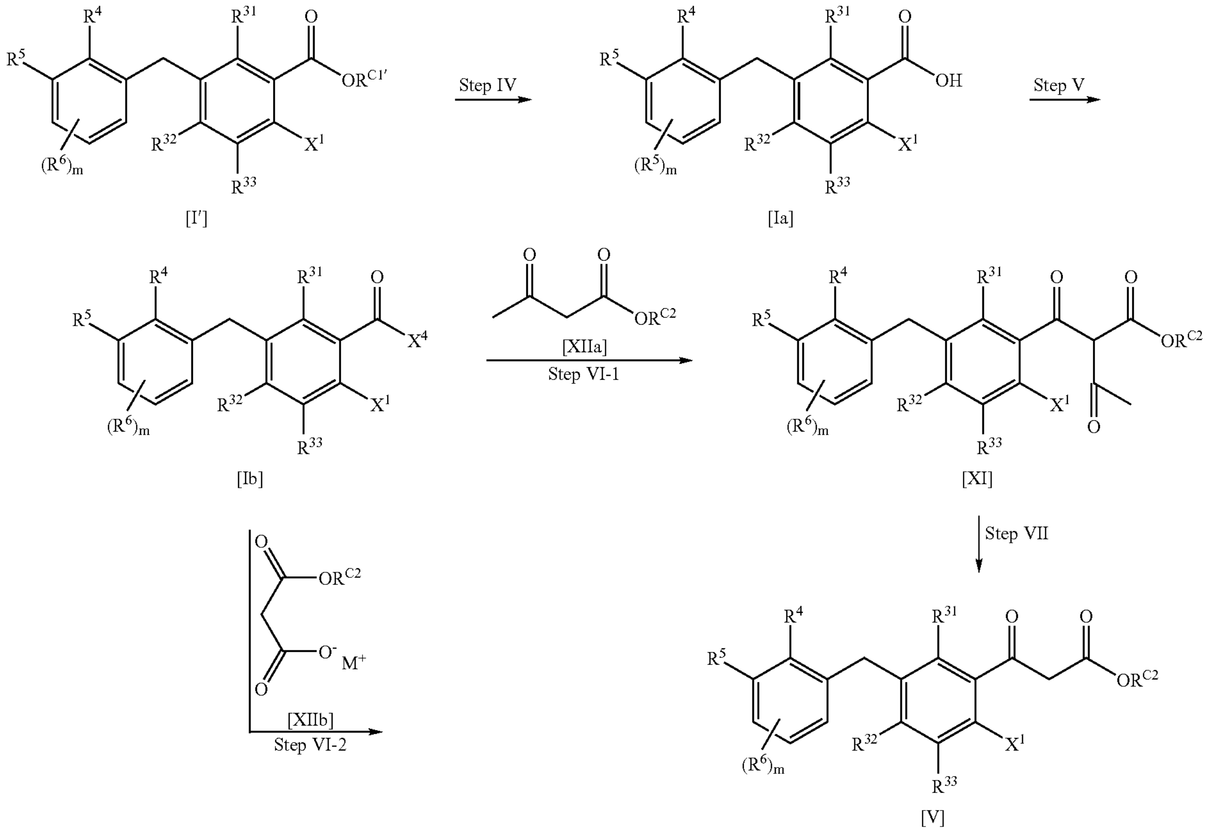

[I'] [Ia] [Ib] [XI] [V]

-continued

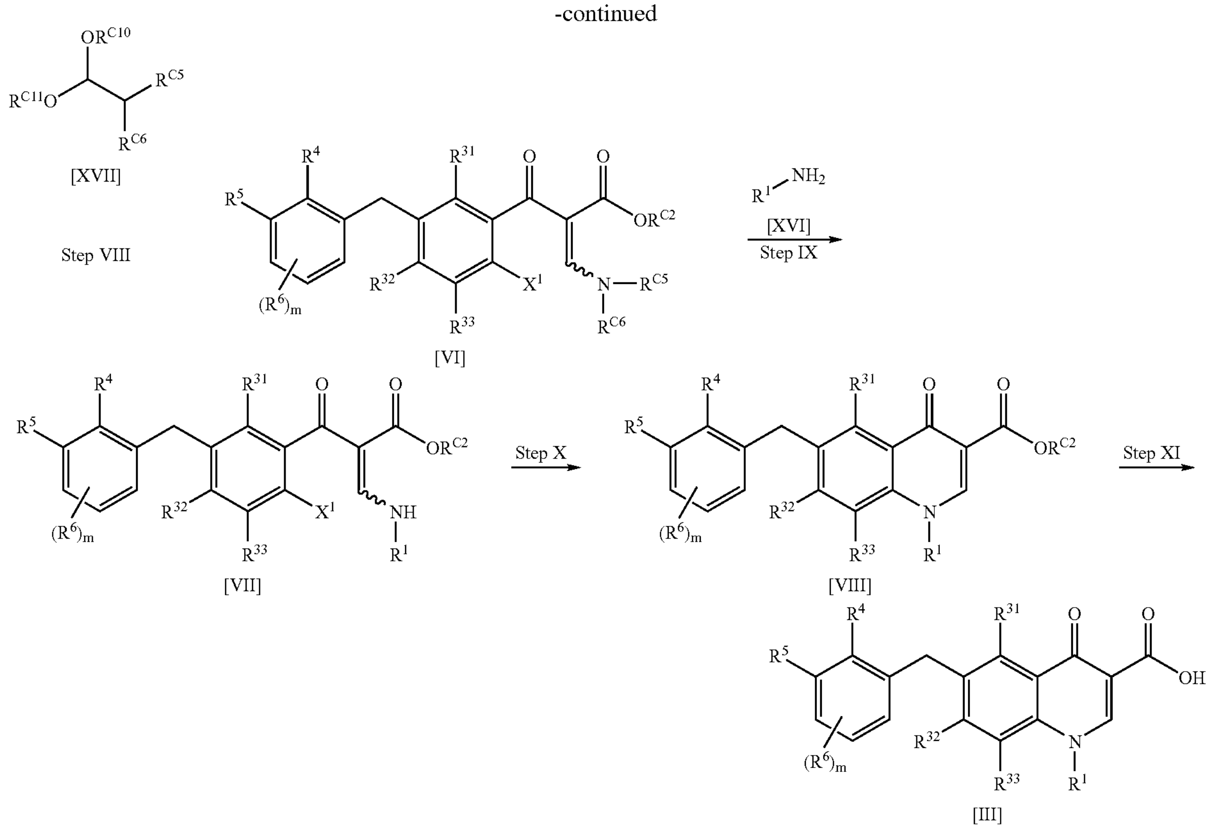

[XVII] [VI] [VII] [VIII] [III]

wherein $R^{C1'}$ is a carboxyl-protecting group, $R^{C2}$ is a carboxyl-protecting group, $R^{C5}$ and $R^{C6}$ are the same or different and each is a $C_{1-4}$ alkyl group, or optionally form, together with the adjacent nitrogen atom, a 5 or 6-membered heterocycle, $R^{C10}$ and $R^{C11}$ are the same or different and each is a $C_{1-4}$ alkyl group, $X^4$ is a halogen atom, M is a metal atom M, and other symbols are as defined above.

Step IV

Compound [Ia] or a salt thereof can be obtained by subjecting compound [I'] or a salt thereof to hydrolysis in a solvent under a basic condition (e.g., in the presence of a base such as sodium hydroxide, potassium hydroxide, lithium hydroxide and the like) or under an acidic condition (e.g., in the presence of an acid such as hydrochloric acid, sulfuric acid and the like). The salt of compound [Ia] is as defined for the above-mentioned definition "pharmaceutically acceptable salt" of the compound of the present invention.

Examples of the solvent include alcohol solvents such as methanol, ethanol, n-propanol, isopropanol and the like; hydrocarbon solvents such as toluene, hexane, xylene and the like; halogenated solvents such as dichloromethane, carbon tetrachloride, 1,2-dichloroethane and the like; ether solvents such as 1,4-dioxane, diethyl ether, 1,2-dimethoxyethane, THF and the like; polar solvents such as 1-methyl-2-pyrrolidinone, N,N-dimethylformamide (DMF), dimethyl sulfoxide, acetonitrile and the like; water or a mixed solvent thereof and the like, with preference given to a mixed solvent of 1-methyl-2-pyrrolidinone and water.

The amount of the base to be used is generally 1 to 10 mol, preferably 1 to 2 mol, per 1 mol of compound [I'].

The amount of the acid to be used is not particularly limited.

The reaction condition is preferably a basic condition, and the reaction is more preferably carried out in the presence of sodium hydroxide, particularly preferably using an aqueous sodium hydroxide solution.

The reaction temperature is generally room temperature to 100° C., preferably room temperature to 40° C. The reaction time is generally 1 hr to 24 hr, preferably 3 hr to 5 hr.

Step V

Compound [Ib] or a salt thereof is obtained by reacting compound [Ia] or a salt thereof with a halogenating agent in a solvent according to a conventional method. The salt of compound [Ib] is as defined for the above-mentioned definition "pharmaceutically acceptable salt" of the compound of the present invention.

Examples of the halogenating agent include phosphorus oxychloride, oxalyl chloride, thionyl chloride and the like, with preference given to thionyl chloride.

The amount of the halogenating agent to be used is generally 1 to 10 mol, preferably 1 to 2 mol, per 1 mol of compound [Ia].

When thionyl chloride is used as a halogenating agent, a base (e.g., N,N-dimethylformamide (DMF) etc.) can be added as necessary.

The amount of the base to be used is not particularly limited.

Examples of the solvent include hydrocarbon solvents such as toluene, xylene and the like; halogenated solvents such as dichloromethane, chloroform, carbon tetrachloride, 1,2-dichloroethane and the like; ethyl acetate and the like, with preference given to toluene.

The reaction temperature is generally room temperature to 100° C., preferably 50° C. to 100° C., particularly preferably 70° C. to 90° C.

The reaction time is generally 1 hr to 10 hr, preferably 1 hr to 3 hr.

Step VI-1

Compound [XI] or a salt thereof, which is a β-diketoester, can be obtained by reacting compound [Ib] or a salt thereof and β-ketoester compound [XIIa] in a solvent in the presence of a base. The salt of compound [XI] is as defined for the above-mentioned definition "pharmaceutically acceptable salt" of the compound of the present invention.

Examples of the base (ligand) include magnesium compounds (e.g., magnesium chloride etc.) or barium oxide and the like.

As the base, barium oxide is preferable

The amount of the base to be used is generally 1 to 10 mol, preferably 1 to 2 mol, per 1 mol of compound [Ib].

Examples of the solvent include alcohol solvents such as methanol, ethanol, n-propanol, isopropanol and the like; hydrocarbon solvents such as toluene, hexane, xylene and the like; halogenated solvents such as dichloromethane, carbon tetrachloride, 1,2-dichloroethane and the like; ether solvents such as 1,4-dioxane, diethyl ether, 1,2-dimethoxyethane, THF and the like; polar solvents such as N,N-dimethylformamide (DMF), dimethyl sulfoxide, acetonitrile and the like; water or a mixed solvent thereof and the like. A mixed solvent of toluene and water, or ethanol is preferable and a mixed solvent of toluene and water is more preferable.

Compound [XIIa] may be commercially available product, or can be synthesized separately according to a known technique. It is particularly preferably ethyl acetoacetate.

The amount of compound [XIIa] to be used is generally 1 to 10 mol, preferably 1 to 2 mol, per 1 mol of compound [Ib].

The reaction temperature is generally 0° C. to 100° C., preferably 0° C. to 50° C., particularly preferably 0° C. to 30° C.

Step VI-2

Compound [V] or a salt thereof, which is a β-diketoester, can be obtained by reacting compound [Ib] or a salt thereof with compound [XIIb], which is a malonic acid monoester, in a solvent in the presence of a base and a chelator, and treating the resulting compound with an acid. The salt of compound [V] is as defined for the above-mentioned definition "pharmaceutically acceptable salt" of the compound of the present invention.

In compound [XIIb], M is a metal atom M.

Compound [XIIb] may be commercially available product, or can be synthesized separately according to a known technique. It is particularly preferably potassium ethyl malonate.

The amount of compound [XIIb] to be used is generally 1 to 10 mol, preferably 2 to 4 mol, per 1 mol of compound [Ib].

Examples of the base include triethylamine and the like, with preference given to triethylamine.

The amount of the base to be used is generally 1 to 10 mol, preferably 2 to 4 mol, per 1 mol of compound [Ib].

Examples of the chelator include magnesium compound such as magnesium(II) chloride and the like, with preference given to magnesium(II) chloride.

The amount of the chelator to be used is generally 1 to 10 mol, preferably 2 to 4 mol, per 1 mol of compound [Ib].

Examples of the solvent include alcohol solvents such as methanol, ethanol, n-propanol, isopropanol and the like; hydrocarbon solvents such as toluene, hexane, xylene and the like; halogenated solvents such as dichloromethane, carbon tetrachloride, 1,2-dichloroethane and the like; ether solvents such as 1,4-dioxane, diethyl ether, 1,2-dimethoxyethane, THF and the like; polar solvents such as N,N-dimethylformamide (DMF), dimethyl sulfoxide, acetonitrile and the like, and the like. An ether solvent is preferable and THF is more preferable.

Examples of the acid include acetic acid, hydrochloric acid, sulfuric acid and the like, with preference given to hydrochloric acid.

The amount of the acid to be used is not particularly limited.

The reaction temperature is generally room temperature to 100° C., preferably 60° C. to 80° C.

The reaction time is generally 1 hr to 12 hr, preferably 3 hr to 8 hr.

Step VII

Compound [V] or a salt thereof can be obtained by subjecting compound [XI] or a salt thereof to a deacetylation reaction in a solvent under a basic condition (e.g., in the presence of a base such as sodium acetate, potassium acetate, sodium carbonate, lithium hydroxide and the like) or under an acidic condition (e.g., in the presence of an acid such as hydrochloric acid, sulfuric acid or acetic acid and the like).

The amount of the base to be used is generally 1 to 10 mol, preferably 2 to 4 mol, particularly preferably 3 mol, per 1 mol of compound [XI].

The amount of the acid to be used is not particularly limited.

The reaction condition is preferably a basic condition, and the reaction is particularly preferably carried out in the presence of sodium acetate.

Examples of the solvent include alcohol solvents such as methanol, ethanol, n-propanol, isopropanol and the like; hydrocarbon solvents such as toluene, hexane, xylene and the like; halogenated solvents such as dichloromethane, chloroform, carbon tetrachloride, 1,2-dichloromethane and the like; ether solvents such as 1,4-dioxane, diethyl ether, 1,2-dimethoxyethane, tetrahydrofuran and the like; polar solvents such as acetonitrile and the like; water or a mixed solvent thereof and the like.

Preferable solvent is a mixed solvent of ethanol and water.

The reaction temperature is generally 0° C. to 100° C., preferably 0° C. to 50° C., particularly preferably 0° C. to 30° C.

The reaction time is generally 20 hr to 120 hr, preferably 24 hr to 100 hr.

Step VII can be continuously performed after the above-mentioned Step VI-1 without isolation treatment of compound [XI] obtained in the above-mentioned Step VI-1.

In this case, the reaction condition is preferably a basic condition, and the reaction is particularly preferably carried out in the presence of sodium acetate.

The amount of the base to be used is generally 1 to 10 mol, preferably 2 to 4 mol, particularly preferably 3 mol, per 1 mol of compound [Ib].

The reaction temperature is generally 0° C. to 100° C., preferably 0° C. to 50° C., particularly preferably 0° C. to 30° C.

The reaction time is generally 20 hr to 120 hr, preferably 24 hr to 100 hr.

Step VIII

Compound [VI] or a salt thereof can be obtained by reacting compound [V] or a salt thereof with compound [XVII] in a solvent. The salt of compound [VI] is as defined for the above-mentioned definition "pharmaceutically acceptable salt" of the compound of the present invention.

Compound [XVII] may be commercially available product, or can be synthesized separately according to a known technique. It is preferably N,N-dimethylformamide dimethyl acetal.

The amount of compound [XVII] to be used is generally 1 to 20 mol, preferably 1 to 10 mol, particularly preferably 1 to 2 mol, per 1 mol of compound [V].

Examples of the solvent include ether solvents such as 1,4-dioxane, diethyl ether, 1,2-dimethoxyethane, THF and the like; hydrocarbon solvents such as toluene, hexane and the like, and the like, with preference given to toluene.

The reaction temperature is generally 20° C. to 100° C., preferably 75° C. to 90° C.

The reaction time is preferably 1 hr to 24 hr, preferably 3 hr to 5 hr.

Step IX

Compound [VII] can be obtained by reacting compound [VI] or a salt thereof with compound [XVI] in a solvent.

Compound [XVI] may be commercially available product, or can be synthesized separately according to a known technique. It is particularly preferably (S)-2-amino-3-methylbutan-1-ol.

The amount of compound [XVI] to be used is generally 1 to 10 mol, preferably 1 to 5 mol, particularly preferably 1 to 2 mol, per 1 mol of compound [VI].

A base can be added to the reaction system, as necessary.

Examples of the base include triethylamine, diisopropylethylamine, pyridine, potassium carbonate and the like.

The amount of the base to be used is not particularly limited.

Examples of the solvent include hydrocarbon solvents such as toluene, hexane, xylene and the like; halogenated solvents such as dichloromethane, chloroform, carbon tetrachloride, 1,2-dichloromethane and the like; ether solvents such as 1,4-dioxane, diethyl ether, 1,2-dimethoxyethane, tetrahydrofuran and the like; polar solvents such as N,N-dimethylformamide (DMF), dimethyl sulfoxide, acetonitrile and the like; ethyl acetate or a mixed solvent thereof and the like, with preference given to toluene.

The reaction temperature is generally room temperature to 100° C., preferably room temperature to 70° C., particularly preferably room temperature to 50° C.

The reaction time is generally 1 hr to 12 hr, preferably 1 hr to 8 hr, particularly preferably 1.5 hr to 5 hr.

The pH of the reaction system after the reaction is preferably 7 to 8.

Step X

Compound [VIII] or a salt thereof can be obtained by subjecting compound [VII] to a cyclization reaction in a solvent. The salt of compound [VIII] is as defined for the above-mentioned definition "pharmaceutically acceptable salt" of the compound of the present invention.

A base can be added to the reaction system, as necessary.

Examples of the base include sodium carbonate, potassium carbonate, sodium hydroxide, potassium hydroxide, potassium tert-butoxide, sodium hydride, potassium hydride, 1,8-diazabicyclo[5.4.0]-7-undecene and the like, with preference given to potassium carbonate.

The amount of the base to be used is generally 1 to 10 mol, preferably 1 to 5 mol, particularly preferably 1 to 2 mol, per 1 mol of compound [VII].

Examples of the solvent include hydrocarbon solvents such as toluene, hexane, xylene and the like; halogenated solvents such as dichloromethane, chloroform, carbon tetrachloride, 1,2-dichloromethane and the like; ether solvents such as 1,4-dioxane, diethyl ether, 1,2-dimethoxyethane, tetrahydrofuran and the like; polar solvents such as N,N-dimethylformamide (DMF), dimethyl sulfoxide, acetonitrile and the like; ethyl acetate or a mixed solvent thereof and the like, with preference given to N,N-dimethylformamide.

The reaction temperature is generally room temperature to 150° C., preferably 50° C. to 100° C. or 60° C. to 110° C.

The reaction time is generally 1 hr to 24 hr, preferably 5 hr to 12 hr, particularly preferably 8 hr to 10 hr.

Step XI

Compound [III] or a salt thereof can be obtained by subjecting compound [VIII] or a salt thereof to hydrolysis in a solvent under a basic condition (e.g., in the presence of a base such as sodium hydroxide, potassium hydroxide, lithium hydroxide and the like) or under an acidic condition (e.g., in the presence of an acid such as hydrochloric acid, sulfuric acid and the like). The salt of compound [III] is as defined for the above-mentioned definition "pharmaceutically acceptable salt" of the compound of the present invention.

The amount of the base to be used is generally 1 to 10 mol, preferably 1 to 5 mol, particularly preferably 1 to 2 mol, per 1 mol of compound [VIII].

The amount of the acid to be used is not particularly limited.

The reaction condition is preferably a basic condition, and the reaction is particularly preferably carried out in the presence of sodium hydroxide.

Examples of the solvent include alcohol solvents such as methanol, ethanol, n-propanol, isopropanol and the like; hydrocarbon solvents such as toluene, hexane, xylene and the like; halogenated solvents such as dichloromethane, chloroform, carbon tetrachloride, 1,2-dichloromethane and the like; ether solvents such as 1,4-dioxane, diethyl ether, 1,2-dimethoxyethane, tetrahydrofuran and the like; polar solvents such as N,N-dimethylformamide (DMF), dimethyl sulfoxide, acetonitrile and the like; water or a mixed solvent thereof and the like, with preference given to a mixed solvent of ethanol and water.

The reaction temperature is preferably 0° C. to 100° C., more preferably 40° C. to 60° C.

The reaction time is preferably 0.5 hr to 12 hr, preferably 0.5 hr to 3 hr.

In the workup, the pH of the reaction mixture is preferably 3-5.

Production Method-3

The production method of compound [III] or a salt thereof from compound [Ib] or a salt thereof obtained in Production method-2, via compound [XIII] (which is a 3-aminoacrylic acid ester derivative), is shown in the following scheme.

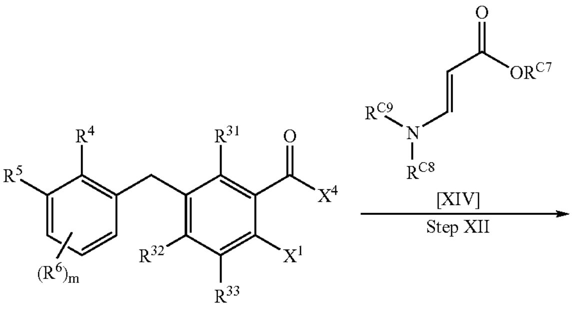

[Ib]

-continued

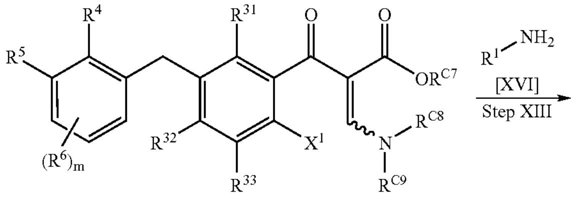

[XIII]

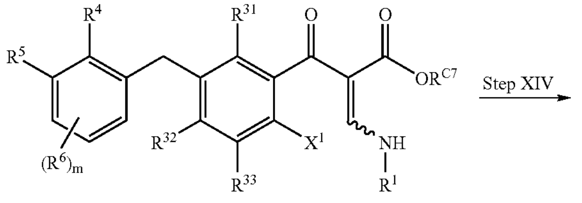

[IX]

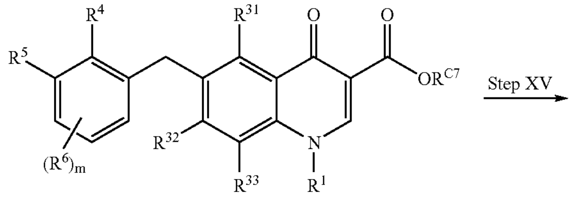

[XV]

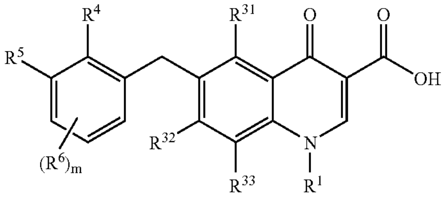

[III]

wherein $R^{C7}$ is a $C_{1-4}$ alkyl group, $R^{C8}$ and $R^{C9}$ are the same or different and each is a $C_{1-4}$ alkyl group, or optionally form, together with the adjacent nitrogen atom, a 5 or 6-membered heterocycle, and the other symbols are as defined above.

Step XII

Compound [XIII] can be obtained by reacting compound [Ib] or a salt thereof obtained in Step V of Production method-2 with compound [XIV] in a solvent in the presence of a base.

Compound [XIV] may be commercially available product, or can be synthesized separately according to a known technique. It is particularly preferably ethyl 3-dimethylaminoacrylate.

The amount of compound [XIV] to be used is generally 1 to 10 mol, preferably 1 to 3 mol, particularly preferably 1 to 2 mol, per 1 mol of compound [Ib].

Examples of the base include triethylamine, N,N-diisopropylamine, potassium carbonate, pyridine and the like with preference given to N,N-diisopropylamine.

The amount of the base to be used is not particularly limited.

Examples of the solvent include hydrocarbon solvents such as toluene, hexane, xylene and the like; halogenated solvents such as dichloromethane, chloroform, carbon tetrachloride, 1,2-dichloroethane and the like; ether solvents such as 1,4-dioxane, diethyl ether, 1,2-dimethoxyethane, THF and the like; polar solvents such as acetonitrile and the like; ethyl acetate or a mixed solvent thereof and the like, with preference given to toluene.

The reaction temperature is generally room temperature to 100° C., preferably 70° C. to 80° C.

The reaction time is generally 1 hr to 12 hr, preferably 6 hr to 12 hr.

Step XIII (Similar to Step IX of Production Method-2)

Compound [IX] can be obtained by reacting compound [XIII] with compound [XVI] in a solvent.

Compound [XVI] may be commercially available product, or can be synthesized separately according to a known technique. It is particularly preferably (S)-2-amino-3-methylbutan-1-ol.

The amount of compound [XVI] to be used is generally 1 to 10 mol, preferably 1 to 5 mol, particularly preferably 1 to 2 mol, per 1 mol of compound [XIII].

A base can be added to the reaction system, as necessary.

Examples of the base include triethylamine, diisopropylethylamine, pyridine, potassium carbonate and the like.

The amount of the base to be used is not particularly limited.

Examples of the solvent include hydrocarbon solvents such as toluene, hexane, xylene and the like; halogenated solvents such as dichloromethane, chloroform, carbon tetrachloride, 1,2-dichloromethane and the like; ether solvents such as 1,4-dioxane, diethyl ether, 1,2-dimethoxyethane, tetrahydrofuran and the like; polar solvents such as N,N-dimethylformamide (DMF), dimethyl sulfoxide, acetonitrile and the like; ethyl acetate or a mixed solvent thereof and the like, with preference given to toluene.

The reaction temperature is generally room temperature to 100° C., preferably room temperature to 70° C., particularly preferably room temperature to 50° C.

The reaction time is generally 1 hr to 12 hr, preferably 1 hr to 8 hr, particularly preferably 1.5 hr to 5 hr.

The pH of the reaction system after the reaction is preferably 7 to 8.

Step XIV (Similar to Step X of Production Method-2)

Compound [XV] or a salt thereof can be obtained by subjecting compound [IX] to a cyclization reaction in a solvent. The salt of compound [XV] is as defined for the above-mentioned definition "pharmaceutically acceptable salt" of the compound of the present invention.

A base can be added to the reaction system, as necessary.

Examples of the base include sodium carbonate, potassium carbonate, sodium hydroxide, potassium hydroxide, potassium tert-butoxide, sodium hydride, potassium hydride, 1,8-diazabicyclo[5.4.0]-7-undecene and the like, with preference given to potassium carbonate.

The amount of the base to be used is generally 1 to 10 mol, preferably 1 to 5 mol, particularly preferably 1 to 2 mol, per 1 mol of compound [IX].

Examples of the solvent include hydrocarbon solvents such as toluene, hexane, xylene and the like; halogenated solvents such as dichloromethane, chloroform, carbon tetrachloride, 1,2-dichloromethane and the like; ether solvents such as 1,4-dioxane, diethyl ether, 1,2-dimethoxyethane, tetrahydrofuran and the like; polar solvents such as N,N-dimethylformamide (DMF), dimethyl sulfoxide, acetonitrile and the like; ethyl acetate or a mixed solvent thereof and the like, with preference given to N,N-dimethylformamide.

The reaction temperature is generally room temperature to 150° C., preferably 50° C. to 100° C. or 60° C. to 110° C.

The reaction time is generally 1 hr to 24 hr, preferably 5 hr to 12 hr, particularly preferably 8 hr to 10 hr.

Step XV (Similar to Step XI of Production Method-2)

Compound [III] or a salt thereof can be obtained by subjecting compound [XV] or a salt thereof to hydrolysis in a solvent under a basic condition (e.g., in the presence of a base such as sodium hydroxide, potassium hydroxide, lithium hydroxide and the like) or under an acidic condition (e.g., in the presence of an acid such as hydrochloric acid, sulfuric acid and the like).

The amount of the base to be used is generally 1 to 10 mol, preferably 1 to 5 mol, particularly preferably 1 to 2 mol, per 1 mol of compound [XV].

The amount of the acid to be used is not particularly limited.

The reaction condition is preferably a basic condition, and the reaction is particularly preferably carried out in the presence of sodium hydroxide.

Examples of the solvent include alcohol solvents such as methanol, ethanol, n-propanol, isopropanol and the like; hydrocarbon solvents such as toluene, hexane, xylene and the like; halogenated solvents such as dichloromethane, chloroform, carbon tetrachloride, 1,2-dichloromethane and the like; ether solvents such as 1,4-dioxane, diethyl ether, 1,2-dimethoxyethane, tetrahydrofuran and the like; polar solvents such as N,N-dimethylformamide (DMF), dimethyl sulfoxide, acetonitrile and the like; water or a mixed solvent thereof and the like, with preference given to a mixed solvent of ethanol and water.

The reaction temperature is preferably 0° C. to 100° C., more preferably 40° C. to 60° C.

The reaction time is preferably 0.5 hr to 12 hr, preferably 0.5 hr to 3 hr.

In the workup, the pH of the reaction mixture is preferably 3-5.

EXAMPLES

A compound useful as a synthetic intermediate for an anti-HIV agent having an integrase inhibitory activity and a production method thereof, and a production method of an anti-HIV agent using the synthetic intermediate are specifically explained next. Those of ordinary skill in the art will understand that the present invention is not limited to these Examples.

Reference Example 1

Synthesis of 3-chloro-2-fluorobenzylzinc bromide

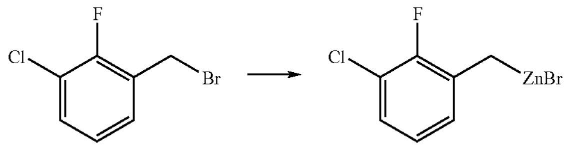

Under an argon atmosphere, a zinc powder (3.18 g) was suspended in tetrahydrofuran (8 ml), 1,2-dibromoethane (0.061 g, 0.32 mmol) and trimethylsilylchloride (0.071 g, 0.65 mmol) were successively added at 60° C., and the mixture was stirred for 30 min. A solution of 3-chloro-2-fluorobenzyl bromide (7.48 g, 32.5 mmol) in tetrahydrofuran (20 ml) was added dropwise to the solution prepared above at 60° C. The mixture was further stirred under heating for 1 hr to give a solution of 3-chloro-2-fluorobenzylzinc bromide in tetrahydrofuran.

Reference Example 2

Synthesis of 3-chloro-2-fluorobenzylzinc chloride

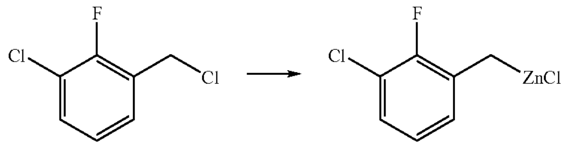

Under an argon atmosphere, a zinc powder (1.44 g) was suspended in tetrahydrofuran (3.6 ml), 1,2-dibromoethane (38 mg) and trimethylsilyl chloride (43 mg) were successively added at 60° C., and the mixture was stirred for 30 min. A solution of 3-chloro-2-fluorobenzylchloride (3.58 g) in tetrahydrofuran (9 ml) was added dropwise at 60° C. to the solution prepared above. The mixture was further stirred under heating for 1 hr to prepare a solution of 3-chloro-2-fluorobenzylzinc chloride in tetrahydrofuran.

Example 1

Step 1

Synthesis of 5-bromo-2,4-dimethoxybenzoic acid

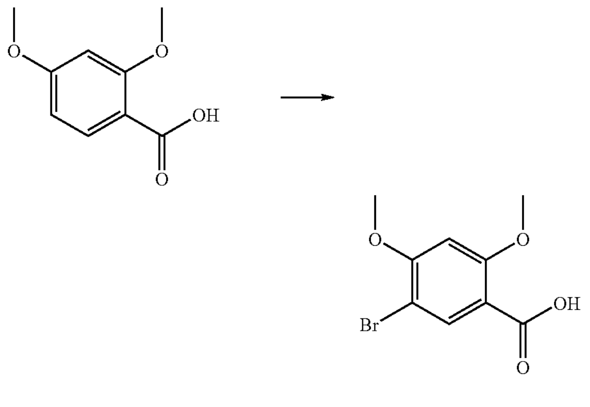

2,4-Dimethoxybenzoic acid (30.0 g) was suspended in acetic acid (180 mL). A bromine (27.6 g)/acetic acid (60 mL) solution was slowly added dropwise to the suspension and, after completion of the dropwise addition, the mixture was stirred at 25° C. for 2 hrs, and the termination of the reaction was confirmed by HPLC. An aqueous solution of sodium sulfite (2.10 g) and water (360 mL) was added dropwise to the reaction mixture. After completion of the dropwise addition, the mixture was stirred at 25° C. for 1 hr. Precipitated crystals were filtered, washed 4 times with water (150 mL), and vacuum dried to give 5-bromo-2,4-dimethoxybenzoic acid as white crystals (41.2 g) (96%).

Step 2

Synthesis of methyl 5-bromo-2,4-dimethoxybenzoate

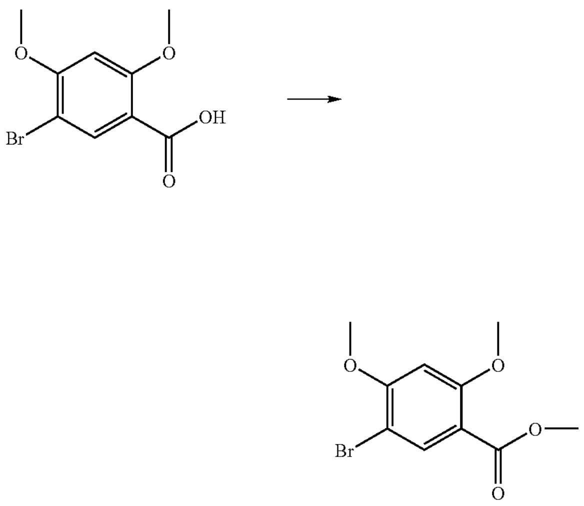

5-Bromo-2,4-dimethoxybenzoic acid (10.0 g) and con sulfuric acid (2.4 g) were added to methanol (80 mL). After reaction at 70° C. for 5 hr, completion of the reaction was confirmed by HPLC. The reaction mixture was cooled and adjusted to pH 7 with 2 mol/L aqueous sodium hydroxide solution, and ethyl acetate (50 mL) was added. The organic solvent was evaporated from the mixture under reduced pressure. To the concentrated residue was added ethyl acetate (50 mL), and the mixture was concentrated again under reduced pressure. To the concentrated residue was added ethyl acetate (70 mL), and the mixture was stirred and partitioned. The obtained organic layer was washed successively with water (50 mL), 5% sodium hydrogencarbonate (50 mL) and water (50 mL). After washing, ethyl acetate was evaporated under reduced pressure to give methyl 5-bromo-2,4-dimethoxybenzoate (9.4 g) (90%).

Step 3

Synthesis of methyl 5-(3-chloro-2-fluorobenzyl)-2,4-dimethoxybenzoate

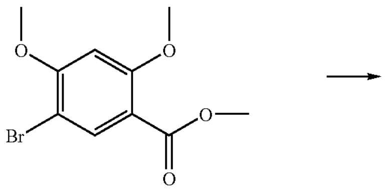

-continued

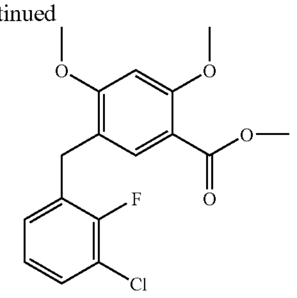

Under a nitrogen atmosphere, tris(dibenzylideneacetone) dipalladium(0) (318 mg) and triphenylphosphine (286 mg) were added to THF (40 mL), and the mixture was stirred at room temperature for 1 hr. A solution of methyl 5-bromo-2, 4-dimethoxybenzoate (5.0 g) obtained in the above-mentioned Step 2/1-methyl-2-pyrrolidinone (40 mL) and a solution (23.4 g) of 29% 3-chloro-2-fluorobenzylzinc bromide in tetrahydrofuran were successively added dropwise at room temperature. After dropwise addition, the mixture was stirred at 65° C. for 2 hr, and completion of the reaction was confirmed by HPLC. After cooling the reaction mixture, toluene (75 mL) and 12.5% aqueous ammonium chloride solution (50 mL) were added, and the mixture was thoroughly stirred and the aqueous layer was discarded. The organic layer was washed successively with 25% aqueous ammonium chloride solution (25 mL), twice with 2% aqueous ethylenediamine solution (25 mL) and three times with 10% brine (25 mL). After washing, the solvent was evaporated under reduced pressure to give methyl 5-(3-chloro-2-fluorobenzyl)-2,4-dimethoxybenzoate (6.81 g). This was directly used in the next step.

Step 4

Synthesis of 5-(3-chloro-2-fluorobenzyl)-2,4-dimethoxybenzoic acid

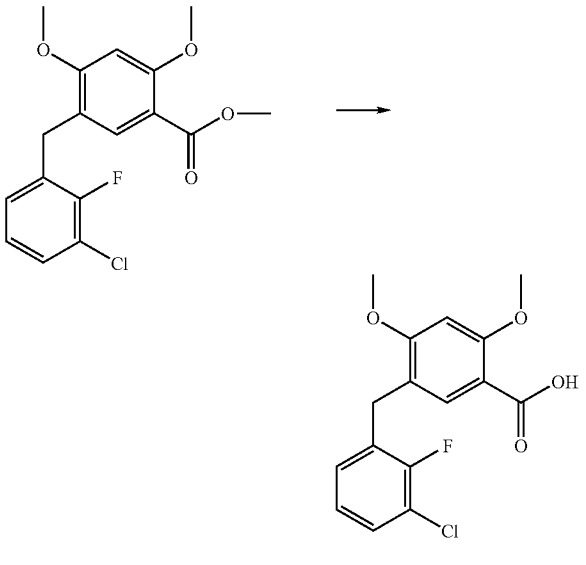

Methyl 5-(3-chloro-2-fluorobenzyl)-2,4-dimethoxybenzoate was dissolved in isopropanol (20 mL), and 1 mol/L aqueous sodium hydroxide solution (30 mL) was added. The mixture was stirred at 70° C. for 3 h, and completion of the reaction was confirmed by HPLC. After cooling the reaction mixture to room temperature, activated carbon (Sirasagi A) (1.0 g) was added. After stirring, the mixture was filtered using powder cellulose (KC FLOCK). The reaction container and the filter were washed with isopropanol (5 mL)/water (5 mL) solution, and combined with the filtrate. Water (20 mL) and hexane (20 mL) were added to the obtained filtrate and, after stirring, the organic layer was removed. The aqueous layer was washed again with hexane (20 mL). The aqueous layer was ice-cooled, methylisopropylketone (50 mL) was added while adding 2 mol/L hydrochloric acid solution (10 mL) dropwise at 10° C. After the addition, the mixture was stirred at room temperature and the aqueous layer was discarded. The organic layer was washed twice with 10% brine (20 mL). After washing, the solvent was evaporated under reduced pressure to give 5-(3-chloro-2-fluorobenzyl)-2,4-dimethoxybenzoic acid (4.8 g, yield 81%, from methyl 5-bromo-2,4-dimethoxybenzoate obtained in Step 2).

Step 5

Synthesis of 5-(3-chloro-2-fluorobenzyl)-2,4-dimethoxybenzoic acid chloride

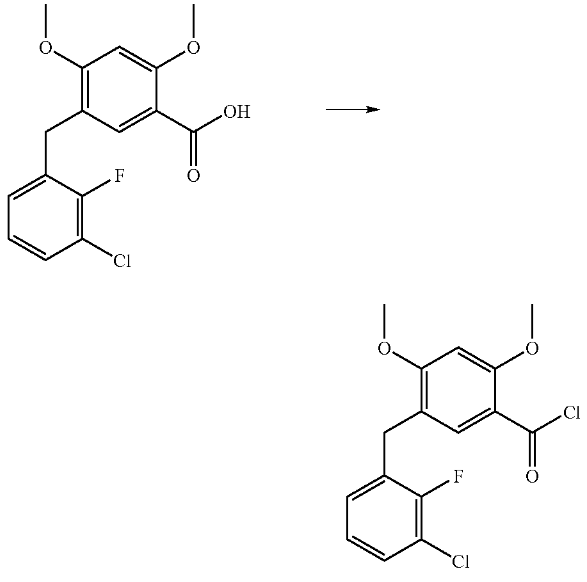

Under a nitrogen atmosphere, 5-(3-chloro-2-fluorobenzyl)-2,4-dimethoxybenzoic acid (4.7 g) was dissolved in DMF/toluene solution (25 mL) (DMF concentration: 300 ppm). Thionyl chloride (2.1 g) was added dropwise to this solution at 75° C. After stirring at 75° C. for 1 hr, completion of the reaction was confirmed by HPLC. Toluene and excess thionyl chloride were evaporated under reduced pressure. Toluene (20 mL) was added to the concentrated residue, and the mixture was concentrated again under reduced pressure to give 5-(3-chloro-2-fluorobenzyl)-2,4-dimethoxybenzoic acid chloride (5.07 g). THF (15 mL) was added thereto to give a suspension of acid chloride (5-(3-chloro-2-fluorobenzyl)-2,4-dimethoxybenzoic acid chloride) in THF, which was directly used in the next step.

Step 6

Synthesis of ethyl 3-(5-(3-chloro-2-fluorobenzyl)-2,4-dimethoxyphenyl)-3-oxopropionate

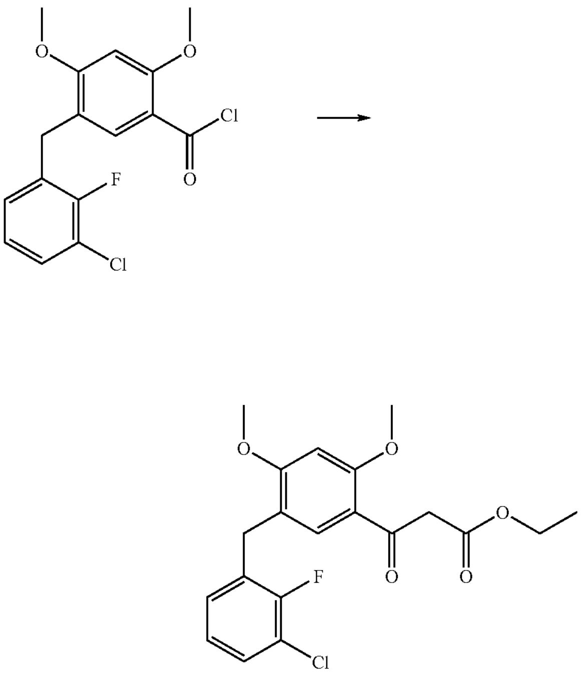

Under a nitrogen atmosphere, THF (5.23 g) was slowly added dropwise to a suspension of anhydrous magnesium chloride (3.45 g) in ethyl acetate (30 mL). After completion of the dropwise addition, the mixture was stirred at 75° C. for 2 hr to dissolve anhydrous magnesium chloride. The solution was added dropwise to an ice-cold suspension of potassium ethyl malonate (4.94 g) and triethylamine (4.40 g) in ethyl acetate (20 mL). After dropwise addition, the suspension was warmed to 70° C. To the suspension was slowly added dropwise a suspension of acid chloride obtained in the above-mentioned Step 5 in THF at 70° C. After completion of the dropwise addition, the mixture was stirred at 70° C. for 0.5 hr, and the completion of the reaction was confirmed by HPLC. 2N hydrochloric acid (30 mL) was added dropwise to the reaction mixture under ice-cooling, and the mixture was stirred at room temperature for 0.5 hr. The organic layer was separated and washed successively with water (25 mL), twice with 5% sodium hydrogencarbonate (25 mL), and water (25 mL). After the washing, the solvent was evaporated under reduced pressure, toluene (25 mL) was added to the concentrated residue and the mixture was concentrated again under reduced pressure to give ethyl 3-(5-(3-chloro-2-fluorobenzyl)-2,4-dimethoxyphenyl)-3-oxopropionate (5.52 g).

Step 7

Synthesis of ethyl 2-(5-(3-chloro-2-fluorobenzyl)-2,4-dimethoxybenzoyl)-3-dimethylminoacrylate

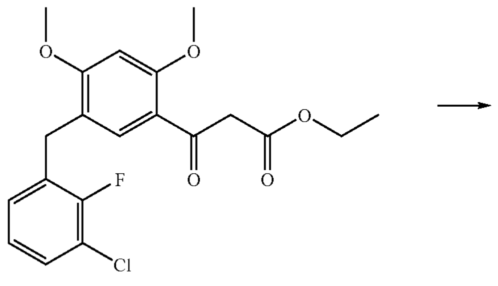

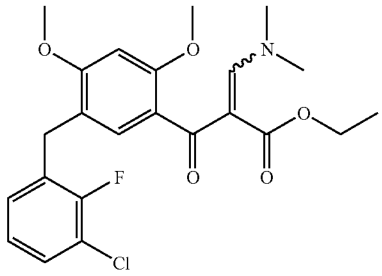

Under a nitrogen atmosphere, ethyl 3-(5-(3-chloro-2-fluorobenzyl)-2,4-dimethoxyphenyl)-3-oxopropionate (2.76 g) and N,N-dimethylformamide dimethyl acetal (1.36 g) were dissolved in toluene. This solution was stirred at 95° C. for 10 hr, and the completion of the reaction was confirmed by HPLC. The reaction mixture was cooled to room temperature to give a solution of ethyl 2-(5-(3-chloro-2-fluorobenzyl)-2,4-dimethoxybenzoyl)-3-dimethylaminoacrylate in toluene. The reaction mixture was directly used in the next step.

Step 8

Synthesis of ethyl 2-(5-(3-chloro-2-fluorobenzyl)-2,4-dimethoxybenzoyl)-3-((S)-1-hydroxymethyl-2-methylpropylamino)acrylate

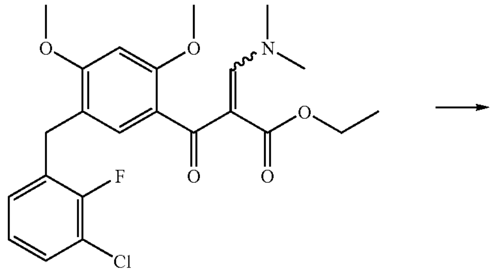

-continued

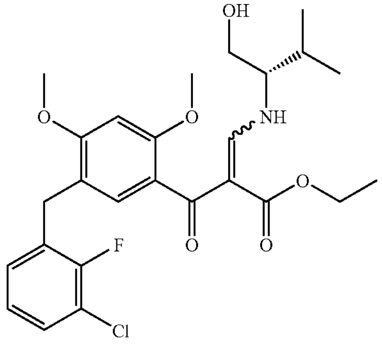

Under a nitrogen atmosphere, L-valinol (1.05 g) was added to the reaction mixture obtained in the above-mentioned Step 7. After stirring at room temperature for 3 hr, the completion of the reaction was confirmed by HPLC. 1 mol/L hydrochloric acid (15 mL) was added to the reaction mixture and, after stirring, the toluene layer was separated. The toluene layer was further washed successively with 1 mol/L hydrochloric acid (15 mL), water (15 mL), 5% aqueous sodium hydrogencarbonate solution (15 mL) and water (15 mL). After the washing, toluene was evaporated under reduced pressure, toluene (10 mL) was added to the concentrated residue, and the mixture was concentrated again under reduced pressure to give ethyl 2-(5-(3-chloro-2-fluorobenzyl)-2,4-dimethoxybenzoyl)-3-((S)-1-hydroxymethyl-2-methylpropylamino) acrylate (3.48 g). This was directly used in the next step.

Step 9

Synthesis of ethyl 2-(5-(3-chloro-2-fluorobenzyl)-2,4-dimethoxybenzoyl)-3-((S)-1-(tert-butyldimethylsilanyloxymethyl)-2-methylpropylamino)acrylate

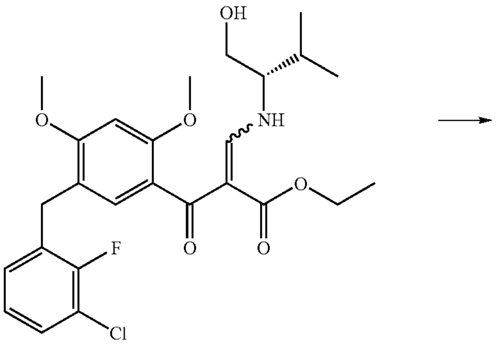

-continued

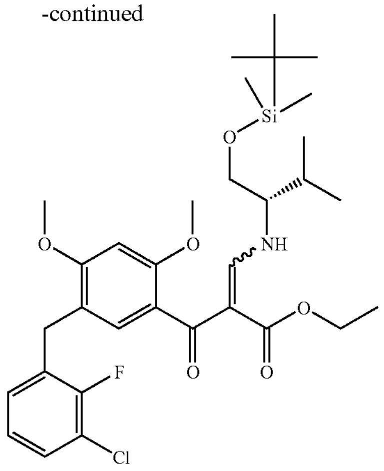

Under a nitrogen atmosphere, ethyl 2-(5-(3-chloro-2-fluorobenzyl)-2,4-dimethoxybenzoyl)-3-((S)-1-hydroxymethyl-2-methylpropylamino)acrylate obtained in the above-mentioned Step 8 and imidazole (646 mg) were added to THF (9.4 mL). A solution (2.39 g) of tert-butyldimethylsilyl chloride in 50% toluene was added dropwise to the solution at 50-70° C. After completion of the dropwise addition, the mixture was stirred at 50-70° C. for 3 hr, and the completion of the reaction was confirmed by HPLC. The reaction mixture was cooled, THF (19 mL) and 10% brine (24 mL) were added and, after stirring, the mixture was partitioned. The organic layer was washed twice with 10% brine (24 mL). After washing, THF was evaporated under reduced pressure, toluene (21 mL) was added to the concentrated residue, and the mixture was concentrated again under reduced pressure to give a crude product. This was purified by column chromatography (ethyl acetate/hexane (1 v/2 v)) to give ethyl 2-(5-(3-chloro-2-fluorobenzyl)-2,4-dimethoxybenzoyl)-3-((S)-1-(tert-butyldimethylsilanyloxymethyl)-2-methylpropylamino)acrylate (3.62 g, yield 79.7%, from 5-(3-chloro-2-fluorobenzyl)-2,4-dimethoxybenzoic acid obtained in Step 4) as a yellow oil.

Step 10

Synthesis of 1-[(S)-1-(tert-butyldimethylsilanyloxymethyl)-2-methylpropyl]-6-(3-chloro-2-fluorobenzyl)-7-methoxy-4-oxo-1,4-dihydroquinoline-3-carboxylic acid ethyl ester

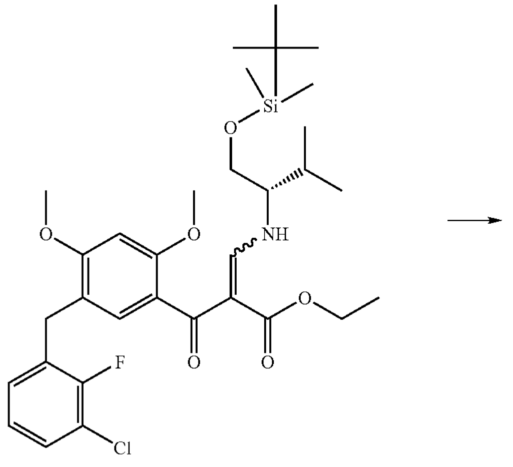

-continued

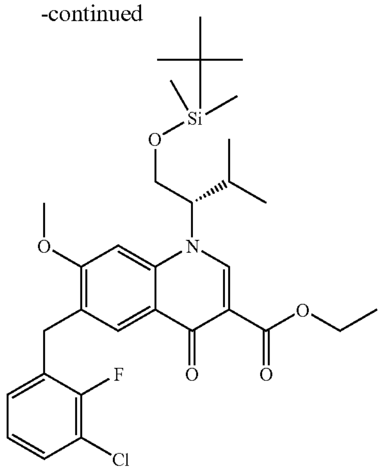

Under a nitrogen atmosphere, ethyl 2-(5-(3-chloro-2-fluorobenzyl)-2,4-dimethoxybenzoyl)-3-((S)-1-(tert-butyldimethylsilanyloxymethyl)-2-methylpropylamino)acrylate (2.0 g) was added to toluene (12 mL), and potassium carbonate (444 mg) and tetra-n-butylphosphonium bromide (1.09 g) were added. After stirring at 110° C. for 22 hr, tetra-n-butylphosphonium bromide (0.55 g), and then potassium carbonate (44 mg) were added, and termination of the reaction was confirmed by HPLC. The reaction mixture was cooled, then allowed to cool to room temperature, and THF (16 mL) and 10% brine (16 mL) were added. The mixture was stirred and partitioned. The organic layer was washed twice with 10% brine (16 mL). After the washing, THF was evaporated under reduced pressure to give crude 1-[(S)-1-(tert-butyldimethyl-silanyloxymethyl)-2-methylpropyl]-6-(3-chloro-2-fluorobenzyl)-7-methoxy-4-oxo-1,4-dihydroquinoline-3-carboxylic acid ethyl ester as a solid. This was purified by column chromatography (ethyl acetate/hexane (2 v/3 v)) to give 1-[(S)-1-(tert-butyldimethyl-silanyloxymethyl)-2-methylpropyl]-6-(3-chloro-2-fluorobenzyl)-7-methoxy-4-oxo-1,4-dihydroquinoline-3-carboxylic acid ethyl ester (937 mg, yield 49.6%) as a yellow-white solid.

Step 11

Synthesis of 6-(3-chloro-2-fluorobenzyl)-1-[(S)-1-hydroxymethyl-2-methylpropyl]-7-methoxy-4-oxo-1,4-dihydroquinoline-3-carboxylic acid

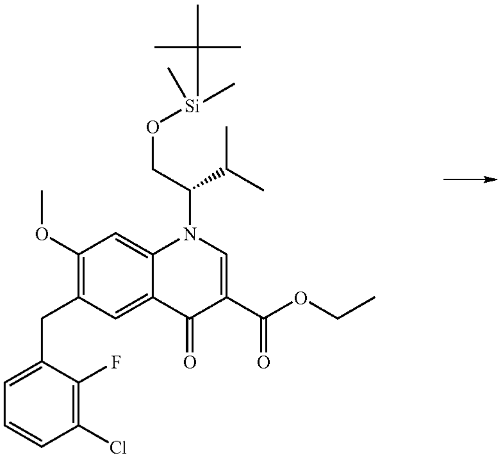

-continued

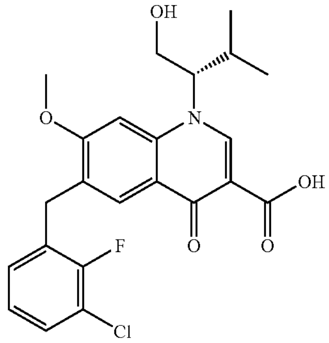

1-[(S)-1-(tert-butyldimethyl-silanyloxymethyl)-2-methylpropyl]-6-(3-chloro-2-fluorobenzyl)-7-methoxy-4-oxo-1,4-dihydroquinoline-3-carboxylic acid ethyl ester (900 mg) was added to isopropyl alcohol (3.6 mL), and 1N sodium hydroxide (3.6 mL) was added. After stirring at 70° C. for 3 hr, the completion of the reaction was confirmed by HPLC. The reaction mixture was cooled, and allowed to cool to room temperature. n-Heptane (5 mL) was added and, after stirring, the mixture was partitioned. The aqueous layer was washed with n-heptane (5 mL). 35% Hydrochloric acid (400 mg) was added to the aqueous layer, methylisopropylketone (10 mL) was added and, after stirring, the mixture was partitioned. The organic layer was washed successively with 8.5% aqueous sodium hydrogencarbonate solution (5 mL) (3 times), 0.5N hydrochloric acid (5 mL) containing sodium chloride (250 mg), and 10% brine (5 mL). After the washing, methylisopropylketone was evaporated under reduced pressure to give 6-(3-chloro-2-fluorobenzyl)-1-[(S)-1-hydroxymethyl-2-methylpropyl]-7-methoxy-4-oxo-1,4-dihydroquinoline-3-carboxylic acid (680 mg, yield 99.3%) as a yellow-white solid.

The compound obtained in Example 1, Step 11 was identified as compound (10).

The property data of the title compound in each step is as follows.

TABLE 1

| Structural formula | $^1$H-NMR | MS(ESI) M+ |
|---|---|---|
| 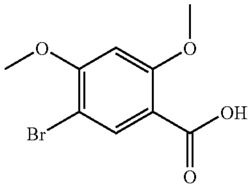 (Step 1) | (DMSO-$d_6$, 300 MHz) δ (ppm): 3.91 (s, 3H), 3.95 (s, 3H), 6.78 (s, 1H), 7.85 (s, 1H), 12.47 (s, 1H). | 261 |
| 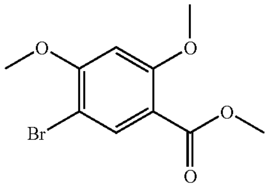 (Step 2) | (DMSO-$d_6$, 300 MHz) δ (ppm): 3.75 (s, 3H), 3.89 (s, 3H), 3.96 (s, 3H), 6.80 (s, 1H), 7.86 (s, 1H). | 275 |
| 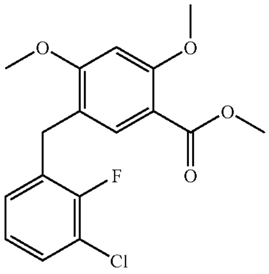 (Step 3) | (DMSO-$d_6$, 300 MHz) δ (ppm): 3.71 (s, 3H), 3.86 (s, 3H), 3.87 (s, 3H), 3.89 (s, 2H), 6.71 (s, 1H), 7.06-7.16 (m, 2H), 7.34-7.48 (m, 1H), 7.51 (s, 1H). | 339 |

TABLE 1-continued
| Structural formula | $^1$H-NMR | MS(ESI) M+ |
|---|---|---|
| 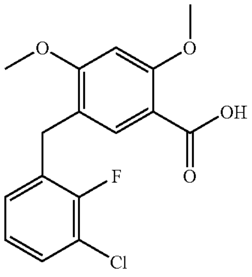 (Step 4) | (DMSO-$d_6$, 300 MHz) δ (ppm): 3.86 (s, 3H), 3.87 (s, 3H), 3.89 (s, 2H), 6.69 (s, 1H), 7.09-7.16 (m, 2H), 7.39-7.46 (m, 1H), 7.69 (s, 1H). | 325 |
| 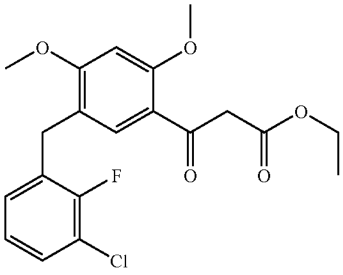 (Step 6) | (DMSO-$d_6$, 400 MHz) δ (ppm): 1.21 (t, 3H, J = 14.4 Hz), 3.83 (s, 2H), 3.85-3.90 (m, 8H), 4.07 (q, 2H, J = 14.4 Hz), 6.72 (s, 1H), 7.10-7.15 (m, 2H), 7.42-7.45 (m, 1H), 7.52 (s, 1H). | 395 |
TABLE 2
| Structural formula | $^1$H-NMR | MS(ESI) M+ |
|---|---|---|
| 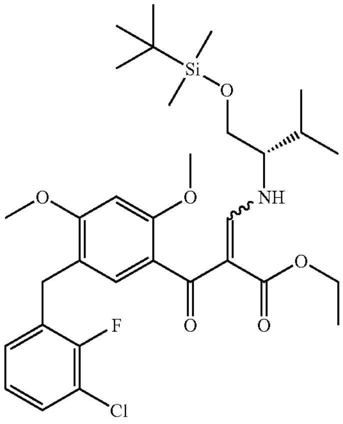 (Step 9) | (DMSO-$d_6$, 400 MHz) δ (ppm): 0.00-0.01 (m, 6H), 0.79-1.00 (m, 10H), 0.85 (s, 9H), 1.88-1.94 (m, 1H), 3.30-3.34 (m, 1H), 3.60-3.90 (m, 6H), 3.62 (s, 3H), 3.84 (s, 3H), 6.58 (s, 1H), 6.87 (s, 1H), 7.10-7.15 (m, 2H), 7.38-7.42 (m, 1H), 7.91 (d, 1H, J = 10.5 Hz). | 622 |

TABLE 2-continued

| Structural formula | $^1$H-NMR | MS(ESI) M+ |
|---|---|---|
| 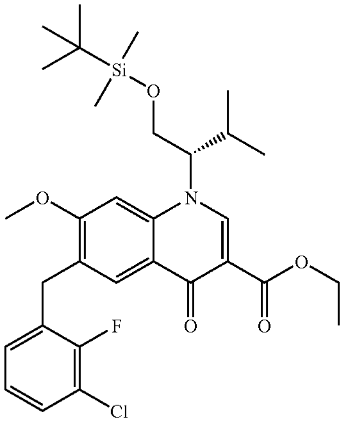 (Step 10) | (DMSO-$d_6$, 300 MHz) δ (ppm): 0.00 (d, 6H, J = 3.4 Hz), 0.81 (s, 9H), 0.85 (d, 3H, J = 6.7 Hz), 1.25 (d, 3H, J = 6.7 Hz), 1.33 (t, 3H, J = 7.1 Hz), 2.40-2.48 (m, 1H), 3.93-3.97 (m, 1H), 4.06 (s, 3H), 4.09-4.15 (m, 3H), 4.20-4.33 (m, 2H), 4.80-4.82 (m, 1H), 7.23-7.36 (m, 2H), 7.37 (s, 1H), 7.53-7.57 (m, 1H), 7.97 (s, 1H), 8.66 (s, 1H). | 590 |
| 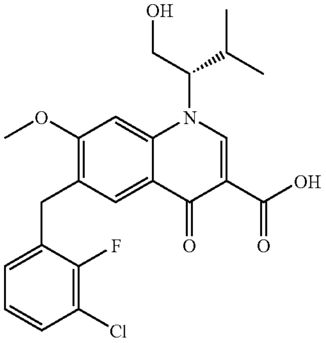 (Step 11) | (DMSO-$d_6$, 300 MHz) δ (ppm): 0.73 (d, 3H, J = 6.7 Hz), 1.16 (d, 3H, J = 6.4 Hz), 2.30-2.55 (m, 1H), 3.75-3.85 (m, 1H), 3.95-4.10 (m, 1H), 4.04 (s, 3H), 4.12 (s, 2H), 4.80-4.95 (m, 1H), 5.15-5.25 (m, 1H), 7.10-7.20 (m, 1H), 7.20-7.25 (m, 1H), 7.40-7.55 (m, 2H), 8.05 (s, 1H), 8.89 (s, 1H), 15.4 (s, 1H). | 448 |

The analysis conditions of HPLC used in the above-mentioned Example 1 are described in the following.

HPLC Analysis Conditions

Analysis Method 1 (Example 1, Step 1-Step 3)

Analysis Conditions column: AM-302 5 μm (150 mm×4.6 mm i.d.) (YMC)

column temperature: 40° C.

mobile phase: mobile phase A: 0.01% aqueous TFA (trifluoroacetic acid) solution mobile phase B: 0.01% TFA acetonitrile solution gradient program

TABLE 3

| time (min) | 0 | 5 | 15 | 20 | 35 | 45 | 55 | 56 | 65 |
|---|---|---|---|---|---|---|---|---|---|
| mobile phase A | 70 | 70 | 50 | 50 | 30 | 20 | 20 | 70 | stopped |
| mobile phase B | 30 | 30 | 50 | 50 | 70 | 80 | 80 | 30 | |

flow rate: 1.0 mL/min detection: UV 220 nm analysis time: 55 min

Analysis Method 2 (Example 1, Step 4-Step 8)

Analysis Conditions column: Inertsil ODS-80A 5 μm (150 mm×4.6 mm i.d.) (GL Sciences Inc)

column temperature: 40° C.

mobile phase: mobile phase A: 0.01% TFA aqueous solution mobile phase B: 0.01% TFA acetonitrile solution gradient program

TABLE 4

| time (min) | 0 | 5 | 15 | 20 | 35 | 45 | 55 | 56 | 65 |
|---|---|---|---|---|---|---|---|---|---|
| mobile phase A | 70 | 70 | 50 | 50 | 30 | 20 | 20 | 70 | stopped |
| mobile phase B | 30 | 30 | 50 | 50 | 70 | 80 | 80 | 30 | |

flow rate: 1.0 mL/min detection: UV 220 nm analysis time: 55 min

Analysis Method 3 (Example 1, Step 9-Step 11)

Analysis Conditions column: Inertsil ODS-80A 5 μm (150 mm×4.6 mm i.d.) (GL Sciences Inc)

column temperature: 40° C.

mobile phase: mobile phase A: 0.01% aqueous TFA solution mobile phase B: 0.01% TFA acetonitrile solution gradient Program

TABLE 5

| time (min) | 0 | 5 | 15 | 20 | 35 | 45 | 65 | 66 | 75 |
|---|---|---|---|---|---|---|---|---|---|
| mobile phase A | 70 | 70 | 50 | 50 | 30 | 20 | 20 | 70 | stopped |
| mobile phase B | 30 | 30 | 50 | 50 | 70 | 80 | 80 | 30 | |

flow rate: 1.0 mL/min
detection: UV 220 nm
analysis time: 65 min

Next, the compound of the present invention represented by the formula [I], which is useful as a synthetic intermediate for an anti-HIV agent having an integrase inhibitory activity and a production method thereof, and a production method of the anti-HIV agent using the synthetic intermediate are specifically explained. However, the present invention is not limited by these Examples.

Example 2

Step I

Synthesis of 3-chloro-2-fluorobenzylzinc bromide

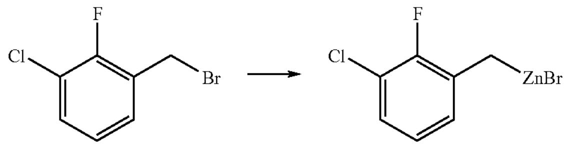

Under an argon atmosphere, a zinc powder (3.18 g) was suspended in tetrahydrofuran (8 ml), 1,2-dibromoethane (0.061 g, 0.32 mmol) and trimethylsilyl chloride (0.071 g, 0.65 mmol) were successively added at 60° C., and the mixture was stirred for 30 min. A solution of 3-chloro-2-fluorobenzylbromide (7.48 g, 32.5 mmol) in tetrahydrofuran (20 ml) was added dropwise at 60° C. to the solution prepared above. The mixture was further stirred under heating for 1 hr to give a solution of 3-chloro-2-fluorobenzylzinc bromide in tetrahydrofuran.

Step II

Synthesis of 5-bromo-2-fluoro-4-methoxybenzoic acid methyl ester

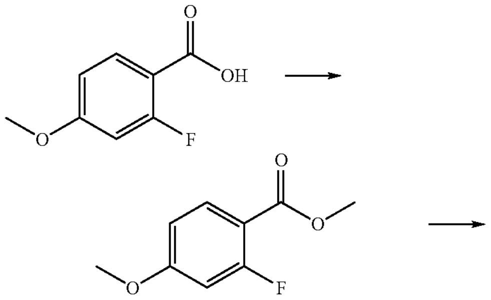

-continued

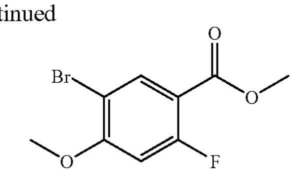

While stirring under ice-cooling, con. sulfuric acid (14 ml) was added dropwise to methanol (840 ml). Then, 2-fluoro-4-methoxybenzoic acid (70.0 g) was added and the mixture was stirred at 65° C. for 14 hr. After cooling the reaction mixture, bromine (152 g) was added dropwise thereto with stirring under ice-cooling. After dropwise addition, the mixture was allowed to warm to room temperature and stirred for 20 hr. Water (840 ml) and sodium sulfite (71.9 g) were successively added. After the addition, the mixture was further stirred for 2 hr, and the precipitated crystals were collected by filtration. The filtrated crystals were washed twice with water (210 ml), and dissolved in toluene (560 ml). The toluene solution was washed successively with 5% aqueous sodium hydrogencarbonate solution (280 ml) and water (280 ml, twice). The organic layer was concentrated under reduced pressure and 1-methyl-2-pyrrolidinone (700 ml) was added to the residue to allow dissolution to give 5-bromo-2-fluoro-4-methoxybenzoic acid methyl ester solution.

The compound was identified as the title compound by HPLC.

HPLC Conditions:

column: Inertsil ODS-80A (4.6×150 mm) (GL Sciences, Inc.)
mobile phase A: 0.01% aqueous TFA solution
mobile phase B: 0.01% TFA-MeCN solution
flow rate: 1 ml/min
column temperature: 40° C.
analysis time: 35 min

| gradient | | | | | | |
|---|---|---|---|---|---|---|
| time (min): | 0 | 10 | 20 | 35 | 36 | 45 |
| mobile phase A: | 70 | 50 | 20 | 20 | 70 | Stop |
| mobile phase B: | 30 | 50 | 80 | 80 | 30 | Stop |

Step III

Synthesis of 5-(3-chloro-2-fluorobenzyl)-2-fluoro-4-methoxybenzoic acid methyl ester

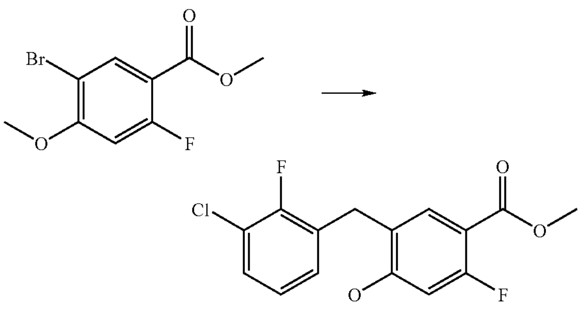

Under a nitrogen atmosphere, tris(dibenzylideneacetone) dipalladium(0) (6.63 g) and triphenylphosphine (5.98 g) were successively added to 1-methyl-2-pyrrolidinone (350 ml) with stirring at room temperature, and the mixture was stirred for 1 hr. A solution of 5-bromo-2-fluoro-4-methoxybenzoic acid methyl ester prepared in Example 2, Step II, in 1-methyl-2-pyrrolidinone and a solution of 3-chloro-2-fluorobenzylzinc bromide prepared in Example 2, Step I, in tetrahydrofuran were successively added dropwise. After the dropwise addition, the mixture was stirred at 85° C. for 2 hr and cooled. To the reaction mixture were added toluene (560 ml) and 12.5% aqueous ammonium chloride solution (980 ml) and the mixture was stirred. The organic layer was washed successively with 25% aqueous ammonium chloride solution (490 ml), 2% aqueous ethylenediamine solution (490 ml, twice) and 10% brine (490 ml, twice). After the washing, the solvent was concentrated under reduced pressure. Ethyl acetate (105 ml) and heptane (420 ml) were added to the residue to allow recrystallization to give 5-(3-chloro-2-fluorobenzyl)-2-fluoro-4-methoxybenzoic acid methyl ester (106.8 g, yield 79.4%).

$^1$H-NMR (DMSO-$d_6$, 300 MHz) (δ) ppm: 3.79 (s, 3H), 3.86 (s, 3H), 3.96 (s, 2H), 7.03 (d, 1H, J=12.8 Hz), 7.14 (m, 2H), 7.45 (m, 1H), 7.64 (d, 1H, J=8.1 Hz).

MS (ESI): $M^+$327

Example 3

Synthesis of 6-(3-chloro-2-fluorobenzyl)-1-((S)-1-hydroxymethyl-2-methylpropyl)-7-methoxy-4-oxo-1,4-dihydroquinoline)-3-carboxylic acid Step IV Synthesis of 5-(3-chloro-2-fluorobenzyl)-2-fluoro-4-methoxybenzoic acid

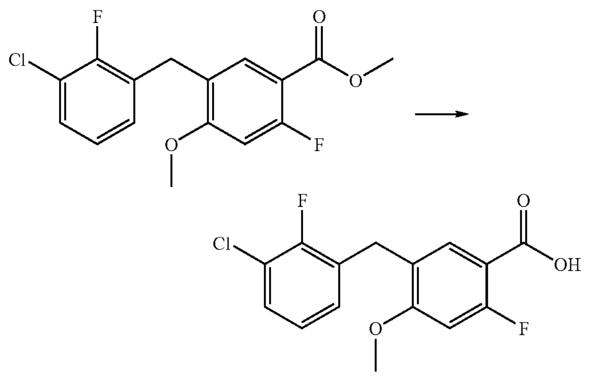

5-(3-Chloro-2-fluorobenzyl)-2-fluoro-4-methoxybenzoic acid methyl ester (100 g) obtained in Example 2, Step III was dissolved in 1-methyl-2-pyrrolidinone (500 ml), and 2.5% V/W aqueous alkali solution prepared from 8N-aqueous sodium hydroxide solution (54.7 ml) and water (192.6 ml) was added dropwise with stirring at room temperature. After the dropwise addition, the mixture was stirred for 3.5 hr, and acidified by dropwise addition of 2N-hydrochloric acid (240 ml) with stirring at room temperature. The precipitated crystals were stirred for 2 hr and collected by filtration. The filtrate was washed with 50% methanol aqueous solution (100 ml) and dried at an outer temperature of 70° C. to give 5-(3-chloro-2-fluorobenzyl)-2-fluoro-4-methoxybenzoic acid (89.4 g, yield 93.4%).

$^1$H-NMR (DMSO-$d_6$, 300 MHz) (δ) ppm: 3.85 (s, 3H), 3.94 (s, 2H), 6.98 (d, 1H, J=12.8 Hz), 7.15 (m, 2H), 7.44 (m, 1H), 7.60 (d, 1H, J=8.8 Hz), 12.8 (s, 1H).

MS (ESI): $M^+$313

Step V

Synthesis of 5-(3-chloro-2-fluorobenzyl)-2-fluoro-4-methoxybenzoyl chloride

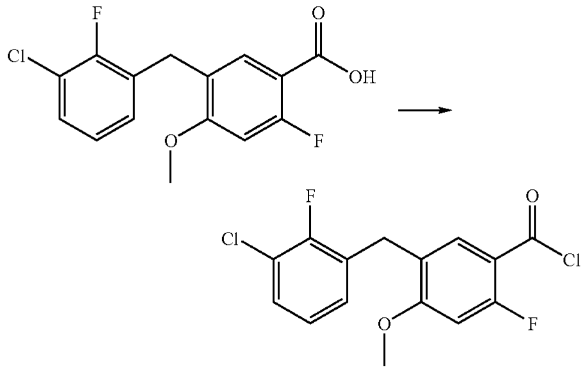

5-(3-Chloro-2-fluorobenzyl)-2-fluoro-4-methoxybenzoic acid (10 g) obtained in Step IV was suspended in toluene (50 ml), and thionyl chloride (4.56 g) was added dropwise at 65-75° C. After the dropwise addition, the mixture was stirred for 1 hr and concentrated under reduced pressure. Toluene (30 ml) was added to the residue, and the mixture was concentrated again under reduced pressure. The residue was dissolved in toluene (30 ml) to give a solution of 5-(3-chloro-2-fluorobenzyl)-2-fluoro-4-methoxybenzoyl chloride in toluene. This was identified as the title compound by HPLC.

HPLC conditions: Same as the HPLC conditions in the above-mentioned Example 2, Step II, except that 10% diethylamine-MeCN solution was used as mobile phase B. Accordingly, a diethylamide form of the title compound was detected.

Step VI-2

Synthesis of 3-(5-(3-chloro-2-fluorobenzyl)-2-fluoro-4-methoxyphenyl)-3-oxopropionic acid ethyl ester

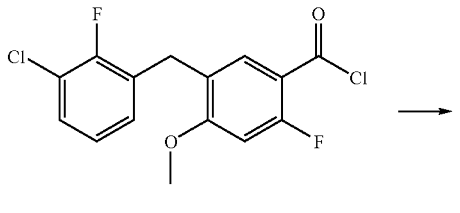

-continued

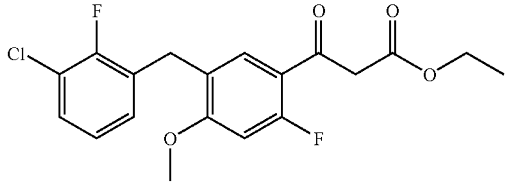

Triethylamine (9.71 g) and magnesium chloride (7.61 g) were successively added to a suspension of potassium ethyl malonate (10.8 g) in tetrahydrofuran with stirring at room temperature. After stirring at 60-70° C. for 1.5 hr, a solution of 5-(3-chloro-2-fluorobenzyl)-2-fluoro-4-methoxybenzoyl chloride prepared in Step V in toluene was added dropwise, and the mixture was further stirred for 30 min. After cooling, toluene (50 ml) and 2N hydrochloric acid (60 ml) were added to the reaction mixture, and the mixture was stirred for 1 hr. The organic layer was washed successively with water (50 ml), 5% sodium hydrogencarbonate (50 ml, twice), and water (50 ml) again, and the organic layer was concentrated under reduced pressure. Toluene (50 ml) was added to the residue, and the mixture was concentrated under reduced pressure. The residue was dissolved in toluene (50 ml) to give a solution of 3-(5-(3-chloro-2-fluorobenzyl)-2-fluoro-4-methoxyphenyl)-3-oxopropionic acid ethyl ester in toluene. This was identified as the title compound by HPLC.

HPLC conditions: Same as the HPLC conditions in the above-mentioned Example 2, Step II, except that 10% diethylamine-MeCN solution was used as mobile phase B. Accordingly, a diethylamide form of the title compound was detected.

Step VIII

Synthesis of 2-(5-(3-chloro-2-fluorobenzyl)-2-fluoro-4-methoxybenzoyl)-3-dimethylaminoacrylic acid ethyl ester

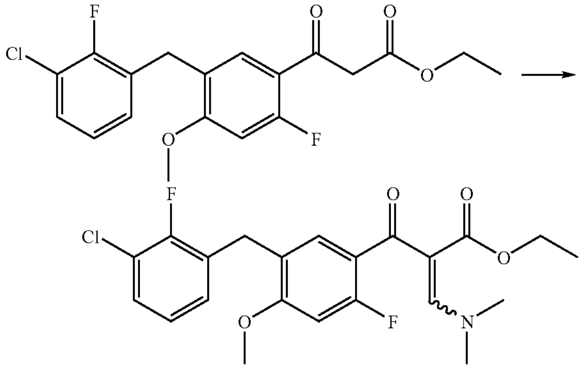

To a solution of 3-(5-(3-chloro-2-fluorobenzyl)-2-fluoro-4-methoxyphenyl)-3-oxopropionic acid ethyl ester prepared in Step VI-2 in toluene was added dropwise at 75-85° C., N,N-dimethylformamide dimethyl acetal (5.08 g) with stirring, and the mixture was stirred for 3 hr. After cooling, a solution of 2-(5-(3-chloro-2-fluorobenzyl)-2-fluoro-4-methoxybenzoyl)-3-dimethylaminoacrylic acid ethyl ester in toluene was obtained. This was identified as the title compound by HPLC.

HPLC conditions: Same as the HPLC conditions in the above-mentioned Example 2, Step II.

Step IX

Synthesis of 2-(5-(3-chloro-2-fluorobenzyl)-2-fluoro-4-methoxybenzoyl)-3-((S)-1-hydroxymethyl-2-methylpropylamino)acrylic acid ethyl ester

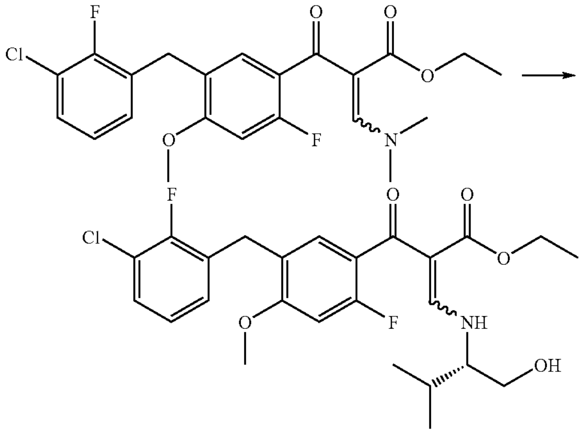

To a solution of 2-(5-(3-chloro-2-fluorobenzyl)-2-fluoro-4-methoxybenzoyl)-3-dimethylaminoacrylic acid ethyl ester prepared in Step VIII in toluene was added (S)-2-amino-3-methylbutan-1-ol (3.96 g) with stirring at room temperature. After stirring for 30 min, 1N hydrochloric acid (60 ml) was added, and the mixture was further stirred for 1 hr. The organic layer was separated and washed successively with water (60 ml), 5% sodium hydrogencarbonate (60 ml) and water (60 ml). The organic layer was concentrated under reduced pressure, N,N-dimethylformamide (40 ml) was added to the residue, and the mixture was concentrated again under reduced pressure. The residue was dissolved in N,N-dimethylformamide (50 ml) to give a solution of 2-(5-(3-chloro-2-fluorobenzyl)-2-fluoro-4-methoxybenzoyl)-3-((S)-1-hydroxymethyl-2-methylpropylamino)acrylic acid ethyl ester in N,N-dimethylformamide. This was identified as the title compound by HPLC.

HPLC conditions: Same as the HPLC conditions in the above-mentioned Example 2, Step II.

Step X

Synthesis of 6-(3-chloro-2-fluorobenzyl)-1-((S)-1-hydroxymethyl-2-methylpropyl)-7-methoxy-4-oxo-1,4-dihydroquinoline)-3-carboxylic acid ethyl ester

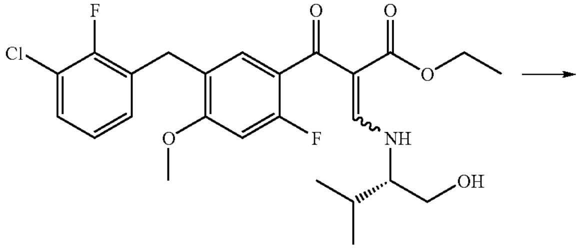

-continued

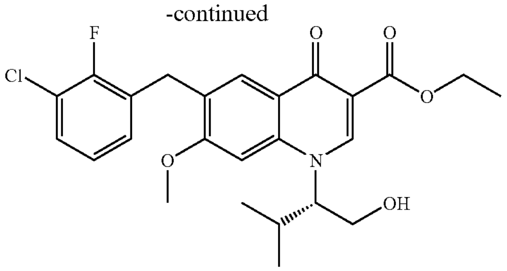

To a solution of 2-(5-(3-chloro-2-fluorobenzyl)-2-fluoro-4-methoxybenzoyl)-3-((S)-1-hydroxymethyl-2-methylpropylamino)acrylic acid ethyl ester prepared in Step IX in N,N-dimethylformamide was added anhydrous potassium carbonate (4.86 g) with stirring at room temperature. After stirring at 95-105° C. for 6 hr, N,N-dimethylformamide (10 ml) and water (50 ml) were successively added dropwise at 65-75° C. to allow crystallization. After stirring for 1 hr, the mixture was cooled to room temperature, and further stirred for 1 hr. Water (20 ml) was further added and, after stirring for 1 hr, and the mixture was filtrated, and the residue was successively washed with 50% aqueous N,N-dimethylformamide solution (20 ml) and water (20 ml), and vacuum dried to give 6-(3-chloro-2-fluorobenzyl)-1-((S)-1-hydroxymethyl-2-methylpropyl)-7-methoxy-4-oxo-1,4-dihydroquinoline)-3-carboxylic acid ethyl ester (13.5 g).

$^1$H-NMR (DMSO-$d_6$, 300 MHz) (δ) ppm: 0.74 (d, 2H, J=6.6 Hz), 1.14 (d, 2H, J=6.6 Hz), 1.26 (t, 3H, J=7.2 Hz), 2.29 (m, 1H), 3.78 (m, 1H), 3.94 (m, 1H), 3.98 (s, 3H), 4.04 (s, 2H), 4.20 (q, 2H, J=7.0 Hz), 4.63 (m, 1H), 5.11 (s, 1H), 7.21 (m, 3H), 7.47 (m, 1H), 7.88 (s, 1H), 8.62 (s, 1H).

MS (ESI): $M^+$476

Step XI

Synthesis of 6-(3-chloro-2-fluorobenzyl)-1-((S)-1-hydroxymethyl-2-methylpropyl)-7-methoxy-4-oxo-1,4-dihydroquinoline)-3-carboxylic acid

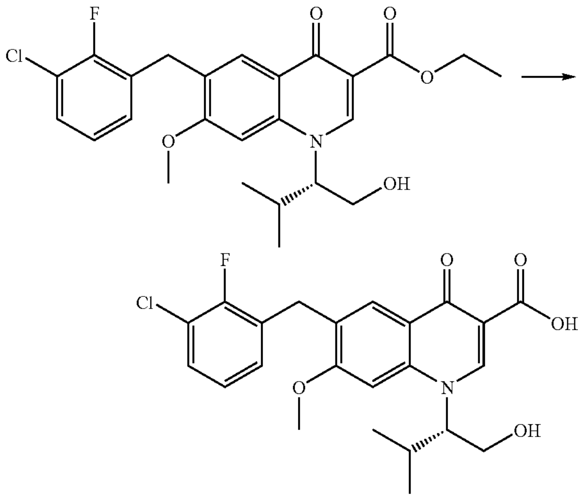

6-(3-Chloro-2-fluorobenzyl)-1-((S)-1-hydroxymethyl-2-methylpropyl)-7-methoxy-4-oxo-1,4-dihydroquinoline)-3-carboxylic acid ethyl ester (5.0 g) was suspended in ethanol (30 ml), and 1.5% V/W aqueous alkali solution prepared from 8N-aqueous sodium hydroxide solution (30 ml) and water (5.53 ml) was added dropwise with stirring at room temperature. After stirring at 45-55° C. for 30 min, the mixture was cooled, and 2N hydrochloric acid (7.88 ml) was added dropwise with stirring at room temperature. Then, a seed crystal (5 mg) of the title compound was added, and the mixture was further stirred for 1 hr. After filtration, the residue was washed with 60% ethanol (10 ml) and vacuum dried to give 6-(3-chloro-2-fluorobenzyl)-1-((S)-1-hydroxymethyl-2-methylpropyl)-7-methoxy-4-oxo-1,4-dihydroquinoline)-3-carboxylic acid (4.34 g, yield 92.9%) having a melting point of 166° C.

$^1$H-NMR (DMSO-$d_6$, 300 MHz) (δ) ppm: 0.73 (d, 2H, J=6.6 Hz), 1.16 (d, 2H, J=6.2 Hz), 2.48 (m, 1H), 3.78 (m, 1H), 3.98 (m, 1H), 4.03 (s, 3H), 4.11 (s, 2H), 4.87 (m, 1H), 5.19 (s, 1H), 7.22 (m, 2H), 7.48 (m, 2H), 8.04 (s, 1H), 8.88 (s, 1H).

MS (ESI): $M^+$448

Synthesis of 6-(3-chloro-2-fluorobenzyl)-1-((S)-1-hydroxymethyl-2-methylpropyl)-7-methoxy-4-oxo-1,4-dihydroquinoline)-3-carboxylic acid

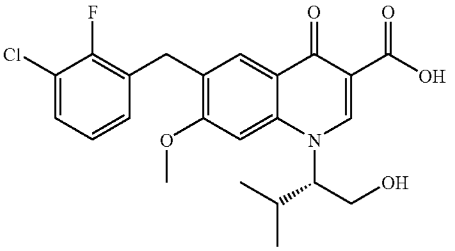

6-(3-Chloro-2-fluorobenzyl)-1-((S)-1-hydroxymethyl-2-methylpropyl)-7-methoxy-4-oxo-1,4-dihydroquinoline)-3-carboxylic acid (8 g) obtained in Step XI was dissolved in acetic acid isobutyl ester (40 ml) at 110-120° C. and, after cooling to room temperature, a seed crystal (8 mg) of the title compound was added. After stirring at room temperature for 5 hr, the precipitated crystals were collected by filtration, washed with acetic acid isobutyl ester (8 ml) and vacuum dried to give 6-(3-chloro-2-fluorobenzyl)-1-((S)-1-hydroxymethyl-2-methylpropyl)-7-methoxy-4-oxo-1,4-dihydroquinoline)-3-carboxylic acid (6.99 g, recovery rate 87.4%).

Example 4

Step V

Synthesis of 5-(3-chloro-2-fluorobenzyl)-2-fluoro-4-methoxybenzoyl chloride

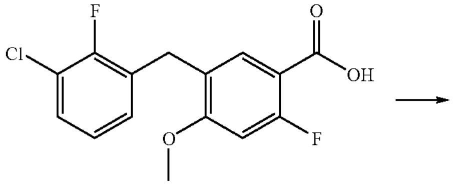

-continued

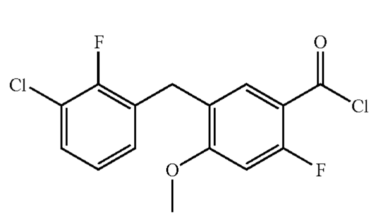

5-(3-Chloro-2-fluorobenzyl)-2-fluoro-4-methoxybenzoic acid (10 g) was suspended in toluene (50 ml) with stirring at room temperature, thionyl chloride (4.57 g) was added dropwise at 65-75° C., and the mixture was stirred for 1.5 hr. After cooling, the solvent was concentrated under reduced pressure, toluene (50 ml) was added to the residue, and the mixture was concentrated again under reduced pressure. The residue was dissolved in toluene (20 ml) to give a solution of 5-(3-chloro-2-fluorobenzyl)-2-fluoro-4-methoxybenzoyl chloride in toluene. This was identified as the title compound by HPLC.

HPLC conditions: Same as the HPLC conditions in the above-mentioned Example 2, Step II, except that 10% diethylamine-MeCN solution was used as mobile phase B. Accordingly, a diethylamide form of the title compound was detected.

Step VI-1

Synthesis of 2-(5-(3-chloro-2-fluorobenzyl)-2-fluoro-4-methoxybenzoyl)-3-oxobutyric acid ethyl ester

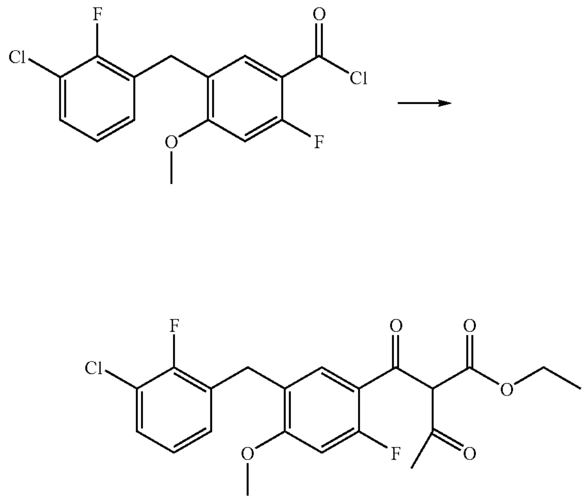

Barium oxide (6.54 g) was added to a mixed solution of water (0.69 g) and toluene (100 ml) with stirring under water-cooling, and the mixture was stirred for 2 hr. Then, a solution of acetoacetic acid ethyl ester (4.99 g) in toluene (5 ml) was added under water-cooling, and the mixture was stirred for 2 hr. A solution (20 ml) of 5-(3-chloro-2-fluorobenzyl)-2-fluoro-4-methoxybenzoyl chloride obtained in the same manner as in Example 3 or 4, Step V, in toluene was added again with stirring under ice-cooling. After stirring for 1 hr, 0.5N hydrochloric acid (100 ml) was added dropwise, and the mixture was further stirred for 2 hr. The organic layer was separated, washed 3 times with 20% brine (50 ml), and concentrated under reduced pressure. Ethanol (100 ml) was added to the residue, and the mixture was concentrated again under reduced pressure. The residue was dissolved in ethanol (100 ml) to give a solution of 2-(5-(3-chloro-2-fluorobenzyl)-2-fluoro-4-methoxybenzoyl)-3-oxobutyric acid ethyl ester in ethanol. This was identified as the title compound by HPLC.

HPLC conditions: Same as the HPLC conditions in the above-mentioned Example 2, Step II, except that 10% diethylamine-MeCN solution was used as mobile phase B. Accordingly, a diethylamide form of the title compound was detected.

Step VII

Synthesis of 3-(5-(3-chloro-2-fluorobenzyl)-2-fluoro-4-methoxyphenyl)-3-oxopropionic acid ethyl ester

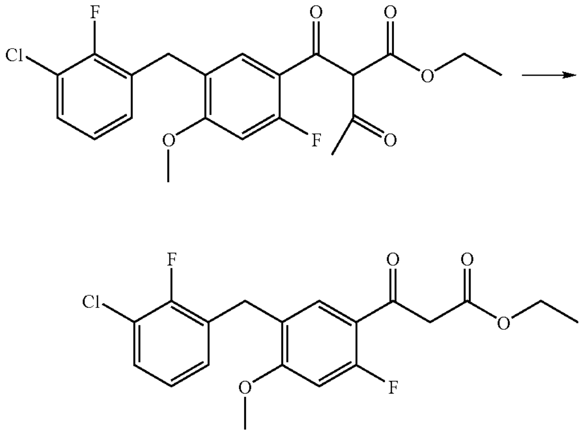

To a solution of 2-(5-(3-chloro-2-fluorobenzyl)-2-fluoro-4-methoxybenzoyl)-3-oxobutyric acid ethyl ester prepared in Step VI-1 in ethanol were successively added water (5 ml) and sodium acetate (7.87 g) with stirring at room temperature, and the mixture was stirred for 4 days. Water (20 ml) was added to the reaction suspension at 70° C. and, after confirmation of dissolution, the mixture was cooled to room temperature. A seed crystal (10 mg) of the title compound was added and, after stirring for 1 hr, water (75 ml) was added again, and the mixture was stirred for 4 hr. The precipitated crystals were collected by filtration, washed with 50% ethanol (20 ml) and vacuum dried to give 3-(5-(3-chloro-2-fluorobenzyl)-2-fluoro-4-methoxyphenyl)-3-oxopropionic acid ethyl ester (10.3 g, yield 84.5%). This was identified as the title compound by HPLC.

HPLC conditions: Same as the HPLC conditions in the above-mentioned Example 2, Step II.

Example 5

Step XII

Synthesis of 2-(5-(3-chloro-2-fluorobenzyl)-2-fluoro-4-methoxybenzoyl)-3-dimethylaminoacrylic acid ethyl ester

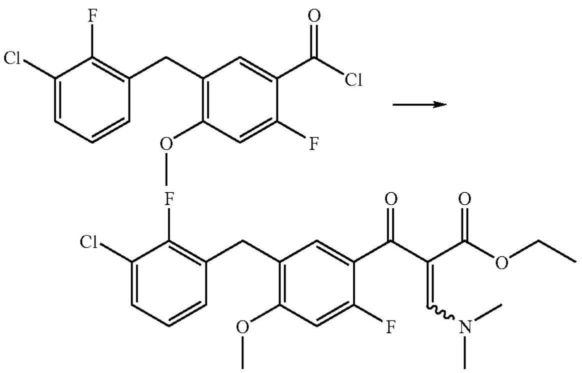

Under a nitrogen atmosphere, 3-dimethylaminoacrylic acid ethyl ester (1.0 g) and N,N-diisopropylamine (1.07 g) were dissolved in toluene (6.0 ml), and a solution of 5-(3-chloro-2-fluorobenzyl)-2-fluoro-4-methoxybenzoyl chloride obtained in the same manner as in Example 3 or 4, Step V, in toluene was added dropwise at 75° C. After dropwise addition, the mixture was stirred for 6 hr, and further heated under reflux for 5 hr. After cooling, a solution of 2-(5-(3-chloro-2-fluorobenzyl)-2-fluoro-4-methoxybenzoyl)-3-dimethylaminoacrylic acid ethyl ester in toluene was obtained. This was identified as the title compound by HPLC.

HPLC conditions: Same as the HPLC conditions in the above-mentioned Example 2, Step II.

Step XIII

Synthesis of 2-(5-(3-chloro-2-fluorobenzyl)-2-fluoro-4-methoxybenzoyl)-3-((S)-1-hydroxymethyl-2-methylpropylamino)acrylic acid ethyl ester

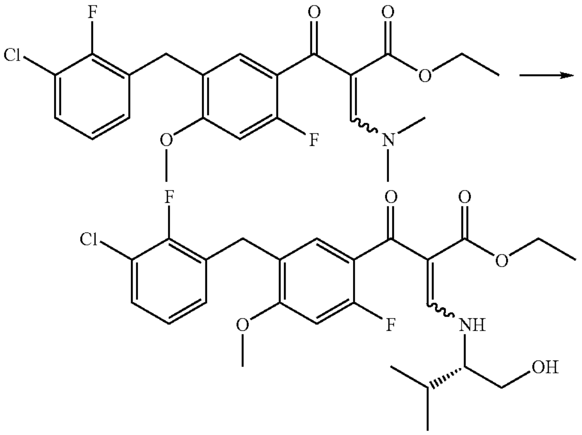

To a solution of 2-(5-(3-chloro-2-fluorobenzyl)-2-fluoro-4-methoxybenzoyl)-3-dimethylaminoacrylic acid ethyl ester prepared in Step XII in toluene was added (S)-2-amino-3-methylbutan-1-ol (3.96 g) with stirring at room temperature. After stirring for 30 min, 1N hydrochloric acid (60 ml) was added, and the mixture was further stirred for 1 hr. The organic layer was separated, and washed successively with water (60 ml), 5% sodium hydrogencarbonate (60 ml) and water (60 ml). The organic layer was concentrated under reduced pressure. N,N-dimethylformamide (40 ml) was added to the residue, and the mixture was concentrated again under reduced pressure. The residue was dissolved in N,N-dimethylformamide (60 ml) to give a solution of 2-(5-(3-chloro-2-fluorobenzyl)-2-fluoro-4-methoxybenzoyl)-3-((S)-1-hydroxymethyl-2-methylpropylamino)acrylic acid ethyl ester in N,N-dimethylformamide. This was identified as the title compound by HPLC.

HPLC conditions: Same as the HPLC conditions in the above-mentioned Example 2, Step II.

Step XIV

Synthesis of 6-(3-chloro-2-fluorobenzyl)-1-((S)-1-hydroxymethyl-2-methylpropyl)-7-methoxy-4-oxo-1,4-dihydroquinoline)-3-carboxylic acid ethyl ester

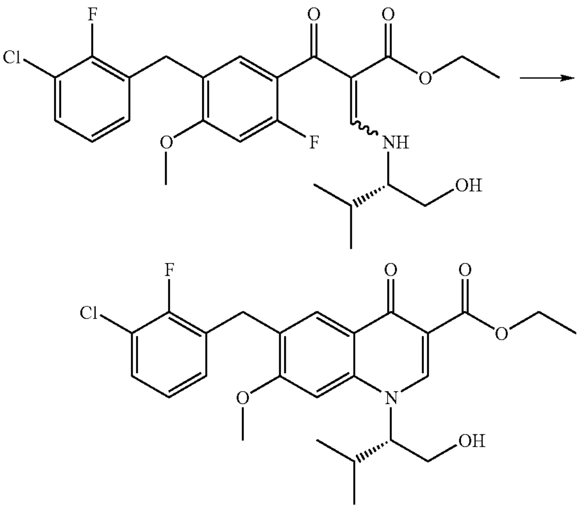

To a solution of 2-(5-(3-chloro-2-fluorobenzyl)-2-fluoro-4-methoxybenzoyl)-3-((S)-1-hydroxymethyl-2-methylpropylamino)acrylic acid ethyl ester prepared in Step IX or Step III in N,N-dimethylformamide was added anhydrous potassium carbonate (4.86 g) with stirring at room temperature. After stirring at 95-105° C. for 6 hr, N,N-dimethylformamide (10 ml) and water (50 ml) were successively added dropwise at 65-75° C. to allow crystallization. After stirring for 1 hr, the mixture was cooled to room temperature and further stirred for 1 hr. Water (20 ml) was further added and, after stirring for 1 hr, the mixture was filtered, and the residue was washed successively with 50% aqueous N,N-dimethylformamide solution (20 ml) and water (20 ml), and vacuum dried to give 6-(3-chloro-2-fluorobenzyl)-1-((S)-1-hydroxymethyl-2-methylpropyl)-7-methoxy-4-oxo-1,4-dihydroquinoline)-3-carboxylic acid ethyl ester (13.5 g)).

Step XV

Synthesis of 6-(3-chloro-2-fluorobenzyl)-1-((S)-1-hydroxymethyl-2-methylpropyl)-7-methoxy-4-oxo-1,4-dihydroquinoline)-3-carboxylic acid

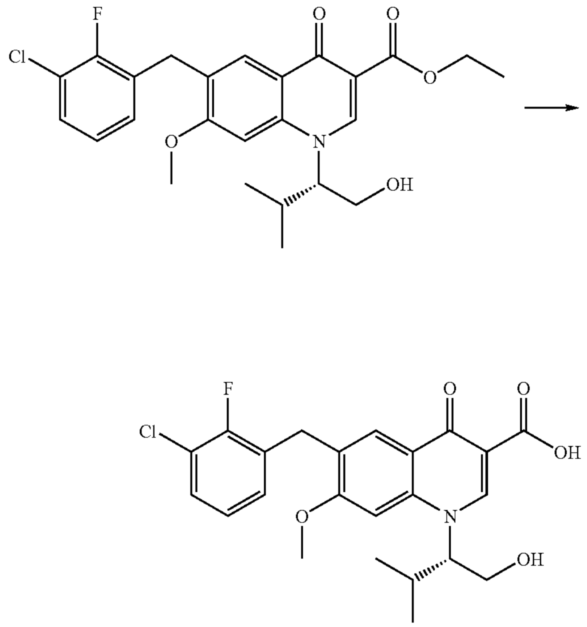 [SMILES: CCOC(=O)c1cn([C@H](CO)C(C)C)c2cc(OC)c(Cc3cccc(Cl)c3F)cc2c1=O ; COc1cc2c(cc1Cc1cccc(Cl)c1F)c(=O)c(C(=O)O)cn2[C@H](CO)C(C)C]

6-(3-Chloro-2-fluorobenzyl)-1-((S)-1-hydroxymethyl-2-methylpropyl)-7-methoxy-4-oxo-1,4-dihydroquinoline)-3-carboxylic acid ethyl ester (5.0 g) was dissolved in ethanol (30 ml), and 1.5% V/W aqueous alkali solution prepared from 8N-aqueous sodium hydroxide solution (30 ml) and water (5.53 ml) was added dropwise with stirring at room temperature. After stirring at 45-50° C. for 30 min, the mixture was cooled, and 2N hydrochloric acid (7.88 ml) was added dropwise with stirring at room temperature. Then, a seed crystal was added, and the mixture was further stirred for 1 hr. The mixture was filtered and the residue was washed with 60% ethanol (10 ml) and vacuum dried to give 6-(3-chloro-2-fluorobenzyl)-1-((S)-1-hydroxymethyl-2-methylpropyl)-7-methoxy-4-oxo-1,4-dihydroquinoline)-3-carboxylic acid (4.23 g, yield 89.8%).

This application is based on a patent application Nos. 2006-60277 and 2006-60298 filed in Japan, the contents of which are incorporated in full herein by this reference.

[Industrial Applicability]

The compound (2') of the present invention is particularly useful as a synthetic intermediate for a compound having an extremely high HIV integrase inhibitory activity (see, for example, WO2004/046115).

In addition, the present invention can provide a method of producing a compound having an HIV integrase inhibitory activity in a good yield.

Moreover, the production method of the present invention is useful as a method for industrial mass synthetic because the method does not use a highly dangerous and highly toxic reagent requiring careful handling and can be performed under mild conditions.

The invention claimed is:

1. A method of producing a compound of the following formula (10):

(10)

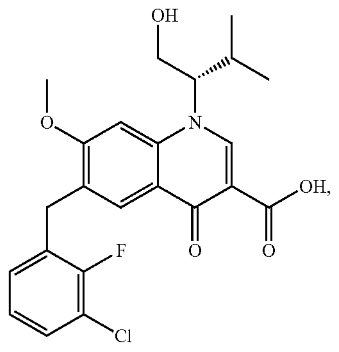

or a salt thereof, comprising reacting a compound of the following formula (8):

(8)

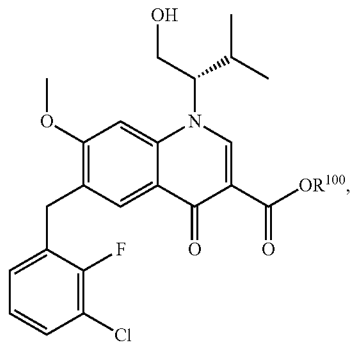

wherein $R^{100}$ is a $C_1$-$C_4$ alkyl group.

2. A method of producing a compound of the following formula (10):

(10)

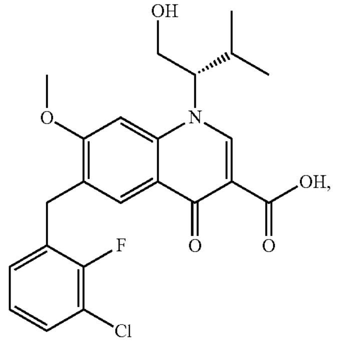

or a salt thereof, comprising reacting a compound of the following formula (2-2-B):

(2-2-B)

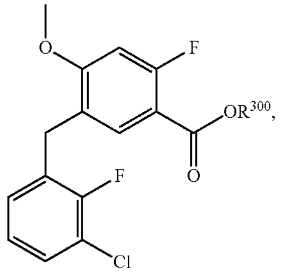

wherein $R^{300}$ is a $C_1$-$C_4$ alkyl group, to produce a compound of the following formula (2-3-B):

(2-3-B)

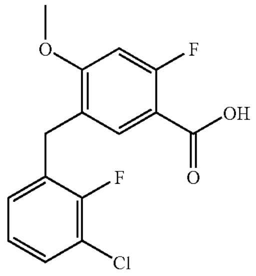

or a salt thereof;

reacting said compound of formula (2-3-B), or a salt thereof, to produce a compound of the following formula (3-B):

(3-B)

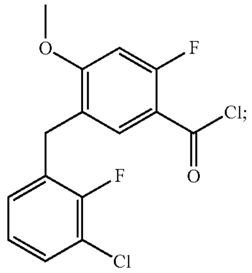

reacting said compound of the formula (3-B) to produce a compound of the following formula (4-B):

(4-B)

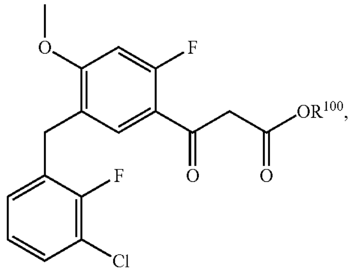

wherein $R^{100}$ is a $C_1$-$C_4$ alkyl group, or a salt thereof;

reacting said compound of the formula (4-B) to produce a compound of the following formula (5-B):

(5-B)

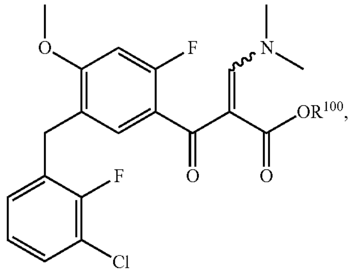

wherein $R^{100}$ is a $C_1$-$C_4$ alkyl group;

reacting said compound of the formula (5-B) to produce a compound of the following formula (6-B):

(6-B)

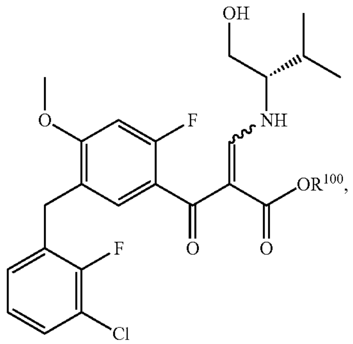

wherein $R^{100}$ is a $C_1$-$C_4$ alkyl group;

reacting said compound of the formula (6-B) to produce a compound of the following formula (8):

(8)

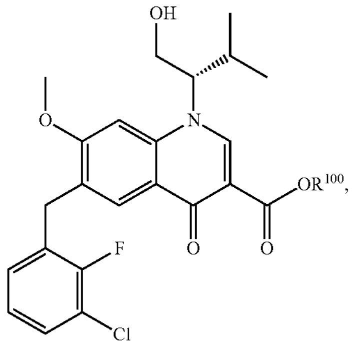

wherein $R^{100}$ is a $C_1$-$C_4$ alkyl group; and reacting said compound of the formula (8) to produce the above compound of the formula (10) or a salt thereof.

3. A compound of the following formula (8):

(8)

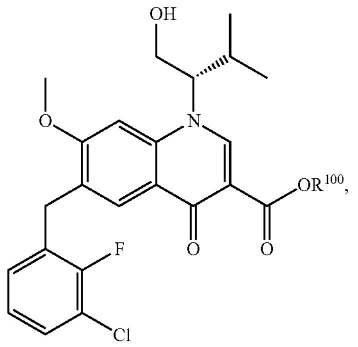

wherein $R^{100}$ is a $C_1$-$C_4$ alkyl group.

4. The compound according to claim 3, wherein $R^{100}$ is ethyl.

5. The method according to claim 1 comprising subjecting the compound of formula (8) to hydrolysis.

6. The method according to claim 5, wherein said hydrolysis occurs in the presence of a base.

7. The method according to claim 6, wherein said base is selected from sodium hydroxide, potassium hydroxide, and lithium hydroxide.

8. The method according to claim 7, wherein said base is sodium hydroxide.

9. The method according to claim 6, wherein said base is present in an amount of 1 to 10 moles per 1 mole of the compound of formula (8).

10. The method according to claim 9, wherein said base is present in an amount of 1 to 5 moles per 1 mole of the compound of formula (8).

11. The method according to claim 10, wherein said base is present in an amount of 1 to 2 moles per 1 mole of the compound of formula (8).

12. The method according to claim 5, wherein said hydrolysis occurs in the presence of an acid.

13. The method according to claim 12, wherein said acid is selected from hydrochloric acid and sulfuric acid.

14. The method according to claim 5, wherein said hydrolysis occurs in at least one solvent selected from methanol, ethanol, n-propanol, isopropanol, toluene, hexane, xylene, dichloromethane, chloroform, carbon tetrachloride, 1,2-dichloroethane, 1,4-dioxane, diethyl ether, 1,2-dimethoxyethane, tetrahydrofuran, N,N-dimethylformamide, dimethylsulfoxide, acetonitrile, and water.

15. The method according to claim 14, wherein said hydrolysis occurs in ethanol and water.

16. The method according to claim 5, wherein said hydrolysis occurs at 0° C. to 100 ° C.

17. The method according to claim 16, wherein said hydrolysis occurs at 40° C. to 60° C.

18. The method according to any one of claim 1 or 5-17, wherein $R^{100}$ is ethyl.

* * * * *

UNITED STATES PATENT AND TRADEMARK OFFICE

CERTIFICATE OF CORRECTION

PATENT NO. : 8,383,819 B2
APPLICATION NO. : 12/281889
DATED : February 26, 2013
INVENTOR(S) : Matsuda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1157 days.

Signed and Sealed this
First Day of April, 2014

Michelle K. Lee
*Deputy Director of the United States Patent and Trademark Office*